US012747269B2

(12) United States Patent
Bei

(10) Patent No.: US 12,747,269 B2
(45) **Date of Patent: *Sep. 29, 2026**

(54) METHODS AND COMPOSITIONS FOR DELIVERY OF AGENTS ACROSS THE BLOOD-BRAIN BARRIER

(71) Applicant: The Brigham and Women's Hospital, Inc., Boston, MA (US)

(72) Inventor: Fengfeng Bei, West Roxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,716

(22) Filed: Oct. 21, 2022

(65) Prior Publication Data

US 2023/0077490 A1 Mar. 16, 2023

Related U.S. Application Data

(60) Division of application No. 17/457,337, filed on Dec. 2, 2021, now Pat. No. 11,518,787, which is a continuation of application No. 17/258,846, filed as application No. PCT/US2019/041386 on Jul. 11, 2019, now Pat. No. 12,398,181.

(60) Provisional application No. 62/696,422, filed on Jul. 11, 2018.

(51) Int. Cl.

| | |
|---|---|
| ***C07K 14/005*** | (2006.01) |
| ***A61K 31/522*** | (2006.01) |
| ***A61K 35/761*** | (2015.01) |
| ***A61K 38/45*** | (2006.01) |
| ***A61K 48/00*** | (2006.01) |
| ***A61K 49/00*** | (2006.01) |
| ***A61P 35/00*** | (2006.01) |
| ***C07K 14/00*** | (2006.01) |
| *A61K 38/00* | (2006.01) |

(52) U.S. Cl.

CPC .......... *C07K 14/005* (2013.01); *A61K 31/522* (2013.01); *A61K 35/761* (2013.01); *A61K 38/45* (2013.01); *A61K 48/0008* (2013.01); *A61K 49/0045* (2013.01); *A61K 49/0097* (2013.01); *A61P 35/00* (2018.01); *C07K 14/001* (2013.01); *A61K 38/00* (2013.01); *C07K 2319/00* (2013.01); *C12N 2750/14122* (2013.01); *C12N 2750/14143* (2013.01)

(58) Field of Classification Search

CPC C07K 14/001; C07K 14/005; C07K 2319/00; C12N 2750/14122; C12N 2750/14143; C12N 15/86; C12N 2710/20041; C12N 2710/20034; C12N 2710/16734; A61K 38/00; A61K 2039/585; A61K 2039/627; A61P 35/00

See application file for complete search history.

(56) References Cited

U.S. PATENT DOCUMENTS

| | | | | |
|---|---|---|---|---|
| 4,522,811 | A | 6/1985 | Eppstein et al. | |
| 8,008,449 | B2 | 8/2011 | Korman et al. | |
| 8,299,215 | B2 | 10/2012 | Davidson et al. | |
| 8,591,900 | B2 | 11/2013 | Barrett et al. | |
| 8,927,514 | B2 | 1/2015 | Chatterjee et al. | |
| 9,073,994 | B2 | 7/2015 | Honjo et al. | |
| 9,102,949 | B2 | 8/2015 | Gao et al. | |
| 9,585,971 | B2 | 3/2017 | Deverman et al. | |
| 10,370,432 | B2 | 8/2019 | Esteves et al. | |
| 10,577,627 | B2 | 3/2020 | Kotin et al. | |
| 11,518,787 | B2 | 12/2022 | Bei | |
| 11,981,705 | B2 * | 5/2024 | Bei | C12N 15/86 |
| 2003/0082143 | A1 | 5/2003 | Larocca et al. | |
| 2003/0165499 | A1 | 9/2003 | Chu et al. | |
| 2004/0120948 | A1 | 6/2004 | Mikayama et al. | |
| 2007/0148163 | A1 | 6/2007 | Takahashi et al. | |
| 2011/0271358 | A1 | 11/2011 | Freeman et al. | |
| 2011/0294218 | A1 | 12/2011 | Chatterjee et al. | |
| 2012/0066783 | A1 | 3/2012 | Kay et al. | |
| 2013/0011405 | A1 | 1/2013 | Long et al. | |
| 2014/0142160 | A1 | 5/2014 | Lee et al. | |
| 2015/0079038 | A1 | 3/2015 | Deverman et al. | |
| 2015/0297742 | A1 | 10/2015 | Strieker et al. | |
| 2016/0280748 | A1 | 9/2016 | Liu et al. | |
| 2016/0376325 | A1 | 12/2016 | McFadden et al. | |
| 2017/0058033 | A1 | 3/2017 | Ludwig et al. | |
| 2017/0130245 | A1 | 5/2017 | Kotin et al. | |
| 2017/0166926 | A1 | 6/2017 | Deverman et al. | |
| 2018/0030429 | A1 | 2/2018 | King et al. | |
| 2018/0141998 | A1 | 5/2018 | Nguyen et al. | |
| 2019/0367562 | A1 | 12/2019 | Asokan et al. | |
| 2020/0325456 | A1 | 10/2020 | Li et al. | |
| 2021/0163985 | A1 | 6/2021 | Sah et al. | |

(Continued)

FOREIGN PATENT DOCUMENTS

| | | | |
|---|---|---|---|
| CA | 3049237 | A1 | 10/2011 |
| CA | 3011939 | A1 | 8/2017 |

(Continued)

OTHER PUBLICATIONS

Kniesel et al. Cell Mol. Neurobiology. Feb. 20, 2000, (1), pp. 57-76.*

Banks Peptides. Oct. 2015 ; 72: 16-19. doi: 10.1016/j.peptides.2015.03.010.*

Tanaka et al. Sci Rep Apr. 8, 2019;9:5769. pp. 1-10.*

JP Office Action in Japanese Appln. No. 2021-500538, mailed on Feb. 6, 2024, 19 pages (with English translation).

Chao et al., "Gene therapy for human lung adenocarcinoma using a suicide gene driven by a lung-specific promoter delivered by JC virus-like particles," PLoS One, Jun. 2016, 11(6):e0157865, 12 pages.

(Continued)

*Primary Examiner* — Bao Q Li

(74) *Attorney, Agent, or Firm* — Fish & Richardson P.C.

(57) ABSTRACT

Sequences that enhance permeation of agents into cells and/or across the blood brain barrier, compositions comprising the sequences, and methods of use thereof.

36 Claims, 33 Drawing Sheets

Specification includes a Sequence Listing.

(56) References Cited

U.S. PATENT DOCUMENTS

| | | | |
|---|---|---|---|
| 2021/0277066 | A1 | 9/2021 | Bei et al. |
| 2021/0301024 | A1 | 9/2021 | Yu et al. |
| 2022/0089650 | A1 | 3/2022 | Bei |
| 2023/0048492 | A1 | 2/2023 | Bei |
| 2023/0053817 | A1 | 2/2023 | Bei et al. |
| 2024/0285804 | A1 | 8/2024 | Bei |

FOREIGN PATENT DOCUMENTS

| | | | |
|---|---|---|---|
| CN | 102170900 | A | 8/2011 |
| CN | 105408486 | A | 3/2016 |
| CN | 112703198 | A | 4/2021 |
| JP | 2016145189 | | 8/2016 |
| JP | 2018510215 | A | 4/2018 |
| WO | WO 2002/088186 | | 11/2002 |
| WO | WO 2005/000220 | | 1/2005 |
| WO | WO 2007/124299 | | 11/2007 |
| WO | WO 2011/123489 | | 10/2011 |
| WO | WO 2012/087983 | | 6/2012 |
| WO | WO 2012/111762 | | 8/2012 |
| WO | WO 2012/145601 | | 10/2012 |
| WO | WO 2012/149356 | | 11/2012 |
| WO | WO 2013/079174 | | 6/2013 |
| WO | WO 2014/052789 | | 4/2014 |
| WO | WO 2014/060109 | | 4/2014 |
| WO | WO 2014/070934 | | 5/2014 |
| WO | WO 2014/086835 | | 6/2014 |
| WO | WO 2014/195852 | | 12/2014 |
| WO | WO 2015/038958 | | 3/2015 |
| WO | WO 2015/060722 | A1 | 4/2015 |
| WO | WO 2015/127094 | | 8/2015 |
| WO | WO 2015/138628 | | 9/2015 |
| WO | WO 2015/191508 | | 12/2015 |
| WO | WO 2016/007235 | | 1/2016 |
| WO | WO 2016/054554 | | 4/2016 |
| WO | WO 2016/061142 | | 4/2016 |
| WO | WO 2016/138525 | | 9/2016 |
| WO | WO 2017/008336 | | 1/2017 |
| WO | WO 2017/083368 | | 5/2017 |
| WO | WO 2017/100671 | | 6/2017 |
| WO | WO 2017/118321 | | 7/2017 |
| WO | WO 2017/136536 | | 8/2017 |
| WO | WO 2019/012176 | | 1/2019 |
| WO | WO 2019/028306 | | 2/2019 |
| WO | WO 2019126356 | | 6/2019 |
| WO | WO 2019/222329 | | 11/2019 |
| WO | WO 2019/222441 | | 11/2019 |
| WO | WO 2020/006274 | | 1/2020 |
| WO | WO 2020/014471 | | 1/2020 |
| WO | WO 2020/028751 | | 2/2020 |
| WO | WO 2020/068990 | | 4/2020 |
| WO | WO 2020/072683 | | 4/2020 |
| WO | WO 2020/077165 | | 4/2020 |
| WO | WO 2020/160337 | | 8/2020 |
| WO | WO 2020/210655 | | 10/2020 |
| WO | WO 2020/223279 | | 11/2020 |
| WO | WO 2021/025995 | | 2/2021 |

OTHER PUBLICATIONS

Doerfler et al., "Copackaged AAV9 vectors promote simultaneous immune tolerance and phenotypic correction of Pompe disease," Human Gene Therapy, Jan. 2016, 27(1):43-59.

Gam et al., "A mixed antagonistic/synergistic miRNA repression model enables accurate predictions of multi-input miRNA sensor activity," Nature Communications, Jun. 2018, 9(1):2430, 12 pages.

Nyon et al., "Engineering a stable CHO cell line for the expression of a MERS-coronavirus vaccine antigen," Vaccine, Mar. 2018, 36(14):1853-62.

snapgene.com, "GAM hsa-mi R-1-5p target sequence," Jun. 3, 22, 2018, 1 page.

snapgene.com, "GAM lsb hsa miR-200c-5p target sequence," Jun. 22, 2018, 1 page.

Trepel et al., "Treatment of multifocal breast cancer by systemic delivery of dual-targeted adeno-associated viral vectors," Gene Therapy, Oct. 2015, 22(10):840-7.

Wu et al., "AAV2/5-mediated NGF gene delivery protects septal cholinergic neurons following axotomy," Brain Research, Nov. 2005, 1061(2):107-13.

Xie et al., "MicroRNA-regulated, systemically delivered rAAV9: a step closer to CNS-restricted transgene expression," Molecular Therapy, Mar. 2011, 19(3):526-35.

Bryan et al., "Implications of protein fold switching," Current Opinion in Structural Biology, Feb. 2013, 2(23):314-6.

Bulcha et al., "Viral vector platforms within the gene therapy landscape," Signal Transduction and Targeted Therapy, Feb. 2021, 6(1):53.

Cruz et al., "Protein function prediction," Functional Genomics: Methods and Protocols, Sep. 2017:55-75.

Kotterman et al., "Engineering adeno-associated viruses for clinical gene therapy," Nature Reviews Genetics, Jul. 2014, 15(7):445-51.

Lenzi et al., "Oversight and Review of Clinical Gene Transfer Protocols: Assessing the Role of the Recombinant DNA Advisory Committee," Committee on the Independent Review and Assessment of the Activities of the NIH Recombinant DNA Advisory Committee, Mar. 2014.

Maqbool et al., "The substrate-binding protein in bacterial ABC transporters: dissecting roles in the evolution of substrate specificity," Biochemical Society Transactions, Oct. 2015, 43(5):1011-7.

Shim et al., "Nonviral delivery systems for cancer gene therapy: strategies and challenges," Current Gene Therapy, Feb. 2018, 18(1):3-20.

JP Japanese Office Action in Japanese Appln. No. 2021-500538, dated Jun. 6, 2023, 11 pages (with English translation).

CN Office Action in Chinese Appln. No. 201980059342.1, mailed on Oct. 10, 2023, 22 pages (with English translation).

Gomez et al., "Cell-penetrating penta-peptides and BAX-inhibiting peptides: Protocol for their application," Cell-Penetrating Peptides: Methods and Protocols, Jan. 2011, 683:465, 6 pages.

Zhang et al., "Blood-brain barrier shuttle peptides enhance AAV transduction in the brain after systemic administration," Biomaterials, Sep. 2018, 176:71, 27 pages.

Alexandrescu et al., "Immunotherapy for melanoma: current status and perspectives," Journal of Immunotherapy (Hagerstown, Md.: 1997), Jul. 2010, 33(6):570.

Avan et al., "Peptidomimetics via modifications of amino acids and peptide bonds, " Chemical Society Reviews, Mar. 2014, 43(10):3575, 1 page (abstract only).

Barash et al., "Human secretory signal peptide description by hidden Markov model and generation of a strong artificial signal peptide for secreted protein expression," Biochemical and Biophysical Research Communications, Jun. 21, 2002, 294(4):835, 1 page (abstract only).

Batista et al., "Ly6a differential expression in blood-brain barrier is responsible for strain specific central nervous system transduction profile of AAV-PHP. B," Human Gene Therapy, Jan. 1, 2020, 31(1-2):90-102.

Brennan et al., "The somatic genomic landscape of glioblastoma," Cell, Oct. 10, 2013, 155(2):462-77.

Chen et al., "Molecular signatures of disease brain endothelia provide new sites for CNS-directed enzyme therapy," Nature Medicine, Oct. 2009, 15(10):1215-8.

Cho et al., "Blood-brain-barrier spheroids as an in vitro screening platform for brain-penetrating agents," Nature Communications, Jun. 6, 2017, 8(1):1-4.

Deverman et al., "Cre-dependent selection yields AAV variants for widespread gene transfer to the adult brain," Nature Biotechnology, Feb. 2016, 34(2):204-9.

Deverman et al., "Gene therapy for neurological disorders: progress and prospects," Nature Reviews Drug Discovery, Sep. 2018, 17(9):641-59.

Eggermont et al., "Anti-CTLA-4 antibody adjuvant therapy in melanoma," Seminars in Oncology, Oct. 1, 2010, 37(5):455-59.

Engeland et al., "CTLA-4 and PD-LI checkpoint blockade enhances oncolytic measles virus therapy, " Molecular Therapy, Nov. 1, 2014, 22(11):1949-59.

(56) References Cited

OTHER PUBLICATIONS

EP Extended Search Report in European Appln. No. 19833958.2, dated Mar. 21, 2022, 9 pages.
Farhadi et al., "Computer-aided design of amino acid-based therapeutics: A review," Drug Design, Development and Therapy, 2018, 12:1239.
Flotte et al., "Expression of the cystic fibrosis transmembrane conductance regulator from a novel adeno-associated virus promoter," Journal of Biological Chemistry, Feb. 15, 1993, 268(5):3781-90.
Ganesan et al., "Systemic therapy for melanoma," National Medical Journal of India, Jan. 1, 2010, 23(1):21.
Geisler et al., "MicroRNA-regulated viral vectors for gene therapy," World Journal of Experimental Medicine, May 20, 2016, 6(2):37.
Golovina et al., "T cells: overcoming suppression of T-cell immunity," The Cancer Journal, Jul. 1, 2010, 16(4):342, 2 pages (abstract only).
Gomez et al., "Bax-inhibiting peptides derived from Ku70 and cell-penetrating pentapeptides," Biochemical Society Transactions, Aug. 1, 2007, 35(4):797-801.
Gomez et al., "Cell-penetrating penta-peptides (CPP5s): measurement of cell entry and protein-transduction activity," Pharmaceuticals, Dec. 2010, 3(12):3594-613.
Gomez, "Development of Cell Penetrating Bax Inhibiting Peptides (BIP), Doctoral dissertation," Case Western Reserve University, Jan. 2010, 189 pages.
Gray et al., "Vector design and considerations for CNS applications," Gene Vector Design and Application to Treat Nervous System Disorders, Jan. 2011, 1-9.
Hermonat et al., "Use of adeno-associated virus as a mammalian DNA cloning vector: transduction of neomycin resistance into mammalian tissue culture cells," Proceedings of the National Academy of Sciences, Oct. 1984, 81(20):6466-70.
Herrlinger et al., "Lomustine-temozolomide combination therapy versus standard temozolomide therapy in patients with newly diagnosed glioblastoma with methylated MGMT promoter (CeTeG/NOA-09): a randomised, open-label, phase 3 trial," The Lancet, Feb. 16, 2019, 393(10172):678-88.
Hordeaux et al., "The GPI-linked protein LY6A drives AAV-PHP. B transport across the blood-brain barrier," Molecular Therapy, May 8, 2019, 27(5):912-21.
Hordeaux et al., "The neurotropic properties of AAV-PHP. B are limited to CS7BL/6J mice," Molecular Therapy, Mar. 7, 2018, 26(3):664-8.
Huang et al., "Delivering genes across the blood-brain barrier: LY6A, a novel cellular receptor for AAV-PHP. B capsids," PloS one, Nov. 14, 2019, 14(11):e0225206.
Hudry et al., "Therapeutic AAV gene transfer to the nervous system: a clinical reality, " Neuron, Mar. 6, 2019, 101(5):839-62.
Jain et al., "Angiogenesis in brain tumours," Nature Reviews Neuroscience, Aug. 2007, 8(8):610-22.
Klinke, "A multiscale systems perspective on cancer, immunotherapy, and Interleukin-12," Molecular Cancer, Dec. 2010, 9(1):1-8.
Kober et al., "Optimized signal peptides for the development of high expressing CHO cell lines," Biotechnology and Bioengineering, Apr. 2013, 110(4):1164-73.
Krüger et al., "Immune based therapies in cancer," Histology and Histopathology, Jun. 2007, 22(6): 687-96.
Li et al., "A mini-review for cancer immunotherapy: molecular understanding of PD-1/PD-L1 pathway & translational blockade of immune checkpoints, " International Journal of Molecular Sciences, Jul. 18, 2016, 17(7):1151, 22 pages.
Lim et al., "Current state of immunotherapy for glioblastoma, " Nature Reviews Clinical Oncology, Jul. 2018, 15(7):422, 1 page (abstract only).
Matsuzaki et al., "Intravenous administration of the adeno-associated virus-PHP. B capsid fails to upregulate transduction efficiency in the marmoset brain," Neuroscience Letters, Feb. 5, 2018, 665:182-8.
Mayo et al., "Design of a partial peptide mimetic of anginex with antiangiogenic and anticancer activity," Journal of Biological Chemistry, Nov. 14, 2003, 278(46):45746-52.
Milletti, "Cell-penetrating peptides: classes, origin, and current landscape," Drug Discovery Today, Aug. 1, 2012, 17(15-16):850-60.
Moschella et al., "Combination strategies for enhancing the efficacy of immunotherapy in cancer patients," Annals of the New York Academy of Sciences, May 2010, 1194(1):169, 1 page (abstract only).
Nakashima et al., "Modeling tumor immunity of mouse glioblastoma by exhausted CD8+ T cells," Scientific Reports, Jan. 2018, 8(1):1-0.
NCBI Accession No. NP_001241.1, "tumor necrosis factor receptor superfamily member 5 isoform 1 precursor [*Homo sapiens*]," dated Oct. 11, 2019, 4 pages.
NCBI Accession No. NP_001254635.1, "programmed cell death 1 ligand 1 isoform b precursor [*Homo sapiens*]," dated Dec. 8, 2019, 3 pages.
NCBI Accession No. NP_001289682.1, "tumor necrosis factor receptor superfamily member 5 isoform 3 precursor [*Homo sapiens*]," Oct. 11, 2019, 3 pages.
NCBI Accession No. NP_001300958.1, "programmed cell death 1 ligand 1 isoform c [*Homo sapiens*]," dated Dec. 8, 2019, 3 pages.
NCBI Accession No. NP_001309350.1, "tumor necrosis factor receptor superfamily member 5 isoform 4 precursor [*Homo sapiens*]," dated Oct. 10, 2019, 4 pages.
NCBI Accession No. NP_001309351.1, "tumor necrosis factor receptor superfamily member 5 isoform 5 precursor [*Homo sapiens*]," dated Oct. 10, 2019, 3 pages.
NCBI Accession No. NP_005009.2, "programmed cell death protein 1 precursor [*Homo sapiens*]," dated Dec. 4, 2019, 4 pages.
NCBI Accession No. NP_054862.1, "programmed cell death 1 ligand 1 isoform a precursor [*Homo sapiens*]," dated Dec. 8, 2019, 4 pages.
NCBI Accession No. NP_690593.1, "tumor necrosis factor receptor superfamily member 5 isoform 2 precursor [*Homo sapiens*]," dated Oct. 10, 2019, 3 pages.
Ostrom et al., CBTRUS statistical report: primary brain and other central nervous system tumors diagnosed in the United States in 2010-2014, Neuro-oncology, Nov. 6, 2017, 19(suppl 5):v1-88.
Pathak et al., "Review on peptidomimetics: a drug designing tool," American Journal of Pharmaceutical Research, Dec. 2015, 5(12).
PCT International Preliminary Report on Patentability in International Appln. No. PCT/US2019/041386, dated Jan. 12, 2021, 7 pages.
PCT International Preliminary Report on Patentability in International Appln. No. PCT/US2021/012746, dated Jul. 12, 2022, 10 pages.
PCT International Search Report and Written Opinion in International Appln. No. PCT/US2019/041386, dated Oct. 17, 2019, 15 pages.
PCT International Search Report and Written Opinion in International Appln. No. PCT/US2021/012746, dated Jul. 1, 2021, 17 pages.
PCT International Search Report and Written Opinion in International Appln. No. PCT/US2022/073051, dated Dec. 28, 2022, 14 pages.
Perry et al., "Histologic classification of gliomas," Handbook of Clinical Neurology, Jan. 1, 2016, 134:71, 1 pages (abstract only).
Pulicherla et al., "Engineering liver-detargeted AAV9 vectors for cardiac and musculoskeletal gene transfer," Molecular Therapy, Jun. 1, 2011, 19(6):1070-8.
Qvit et al., "Peptidomimetic therapeutics: scientific approaches and opportunities," Drug Discovery Today, Feb. 2017, 22(2):454-62.
Reul et al., "Tumor-specific delivery of immune checkpoint inhibitors by engineered AAV vectors," Frontiers in Oncology, Feb. 14, 2019, 9:52.
Stupp et al., "Radiotherapy plus concomitant and adjuvant temozolomide for glioblastoma," New England Journal of Medicine, Mar. 10, 2005, 352(10):987-96.
Sun et al., "Enhanced efficacy of an AAV vector encoding chimeric, highly secreted acid α-glucosidase in glycogen storage disease type II, " Molecular Therapy, Dec. 1, 2006, 14(6):822-30.

(56) References Cited

OTHER PUBLICATIONS

Tratschin et al., “A human parvovirus, adeno-associated virus, as a eucaryotic vector: transient expression and encapsidation of the procaryotic gene for chloramphenicol acetyltransferase, ” Molecular and Cellular Biology, Oct. 1984, 4(10):2072-81.
Tratschin et al., “Adeno-associated virus vector for high-frequency integration, expression, and rescue of genes in mammalian cells,” Molecular and Cellular Biology, Nov. 1985, 5(11):3251-60.
Tratschin et al., “Genetic analysis of adeno-associated virus: properties of deletion mutants constructed in vitro and evidence for an adeno-associated virus replication function,” Journal of Virology, Sep. 1984, 51(3):611-9.
Tsuchiya et al., “Gene design of signal sequence for effective secretion of protein, ”Nucleic Acids Symposium Series, Sep. 2003, 3(1):261-62.
Von Heijne, “Signal sequences: the limits of variation,” Journal of Molecular Biology, Jul. 1985, 184(1):99, 1 page (abstract only).
Wang et al., “A rationally engineered capsid variant of AAV9 for systemic CNS-directed and peripheral tissue-detargeted gene delivery in neonates,” Molecular Therapy-Methods & Clinical Development, Jun. 15, 2018, 9:234-46.
Wen et al., “Malignant gliomas in adults,” New England Journal of Medicine, Jul. 31, 2008, 359(5):492-507.
Wolfe et al., “Machine learning to predict cell-penetrating peptides for antisense delivery,” ACS Central Science, Apr. 5, 2018, 4(4):512-20.
Wondisford et al., “Cloning of the human thyrotropin β-subunit gene and transient expression of biologically active human thyrotropin after gene transfection,” Molecular Endocrinology, Jan. 1988, 2(1):32-9.
Xu et al., “A combination of mutations enhances the neurotropism of AAV-2,” Virology, Oct. 25, 2005, 341(2):203-14.
McMahon et al., “Differences in polyadenylation site choice between somatic and male germ cells,” BMC Molecular Biology, Dec. 2006, 7:1, 11 pages.
O’Carroll et al., “AAV targeting of glial cell types in the central and peripheral nervous system and relevance to human gene therapy,” Frontiers in Molecular Neuroscience, Jan. 2021, 13:618020, 19 pages.
Wang et al., “Astrocytic expression of transgene in the rat brain mediated by baculovirus vectors containing an astrocyte-specific promoter,” Gene Therapy, Oct. 2006, 13(20):1447-56.
Zanta-Boussif et al., “Validation of a mutated PRE sequence allowing high and sustained transgene expression while abrogating WHV-X protein synthesis: application to the gene therapy of WAS,” Gene Therapy, May 2009, 16(5):605-19.
CN Office Action in Chinese Appln. No. 201980059342.1, mailed on Jul. 18, 2024, 9 pages (with English translation).
EP Office Action in European Appln. No. 19833958.2, mailed on Jun. 3, 2024, 4 pages.
CA Office Action in Canadian Appln. No. 3,105,381, mailed on Dec. 19, 2025, 7 pages.
Geisler et al., “microRNA122-regulated transgene expression increases specificity of cardiac gene transfer upon intravenous delivery of AAV9 vectors,” Gene therapy, Feb. 2011, 18(2):199-209.
Qiao et al., “Liver-specific microRNA-122 target sequences incorporated in AAV vectors efficiently inhibits transgene expression in the liver,” Gene Therapy, Apr. 2011, 18(4):403, 19 pages.
Taschenberger et al., “A microRNA124 target sequence restores astrocyte specificity of gfaABCID-driven transgene expression in AAV-mediated gene transfer,” Molecular Therapy Nucleic Acids, Sep. 2017, 8:13, 17 pages.
Ma et al., “Biodistribution of adeno-associated virus 9-mediated gene expression with a CAR promoter in mice,” Chinese Journal of Virology, May 2019, 35(3), 8 pages (with English Abstract).

* cited by examiner

C57BL/6J, 4 × $10^{12}$ vg

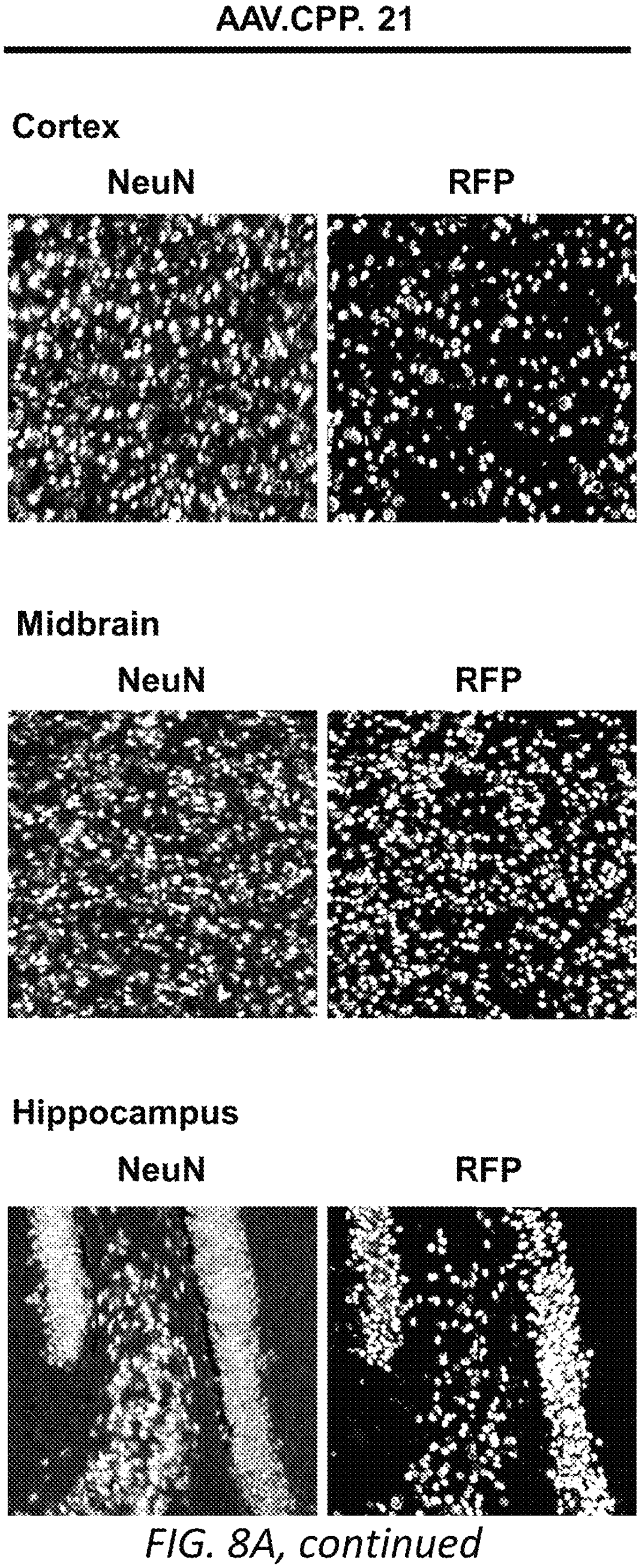
*FIG. 8A, continued*

AAV9

AAV.CPP.21

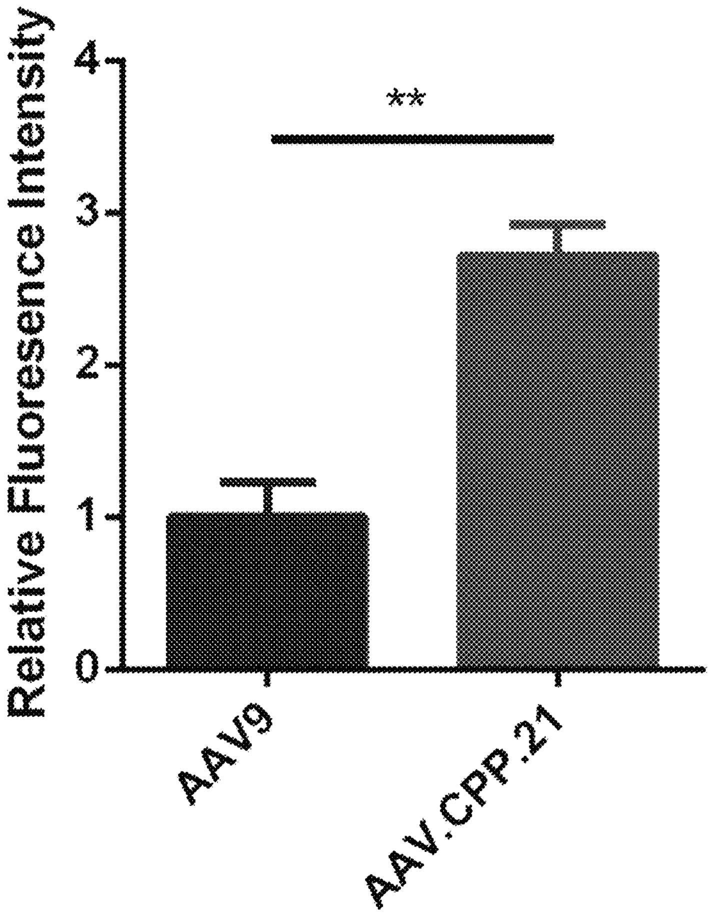
*FIG. 13, continued*

METHODS AND COMPOSITIONS FOR DELIVERY OF AGENTS ACROSS THE BLOOD-BRAIN BARRIER

CLAIM OF PRIORITY

This application is a divisional of U.S. patent application Ser. No. 17/457,337, filed Dec. 2, 2021, which is a continuation of U.S. patent application Ser. No. 17/258,846, filed on Jan. 8, 2021, which is a National Stage application under 35 U.S.C. § 371 of International Application No. PCT/US2019/041386, filed on Jul. 11, 2019, which claims the benefit of U.S. Provisional Application Ser. No. 62/696,422, filed on Jul. 11, 2018. The entire contents of the foregoing are incorporated herein by reference.

SEQUENCE LISTING

The instant application contains a Sequence Listing which has been submitted electronically in .xml format and is hereby incorporated by reference in its entirety. Said ASCII copy, created on Oct. 21, 2022, is named "40175-0034003_SL_ST26" and is 127,955 bytes in size.

TECHNICAL FIELD

Described herein are sequences that enhance permeation of agents across the blood brain barrier, compositions comprising the sequences, and methods of use thereof.

BACKGROUND

Delivery of therapeutic agents, including gene therapy reagents, is an impediment to development of treatments for a number of conditions. The blood-brain barrier (BBB) is a key obstacle for drug delivery to the mammalian central nervous system (CNS), particularly for delivery to the human brain, to treat conditions including neurodegenerative diseases such as Parkinson's disease; Alzheimer's disease; Huntington's disease; Amyotrophic lateral sclerosis; and Multiple sclerosis.

SUMMARY

The present invention is based on the development of artificial targeting sequences that enhance permeation of agents into cells and across the blood brain barrier.

Thus provided herein is an AAV capsid protein, e.g., an engineered AAV capsid protein, comprising a targeting sequence that comprises at least four contiguous amino acids from the sequence TVSALFK (SEQ ID NO:8); TVSALK (SEQ ID NO:4); KLASVT (SEQ ID NO:83); or KFLASVT (SEQ ID NO:84). In some embodiments, the AAV capsid protein comprises a targeting sequence that comprises at least five contiguous amino acids from the sequence TVSALK (SEQ ID NO:4); TVSALFK (SEQ ID NO:8); KLASVT (SEQ ID NO:83); or KFLASVT (SEQ ID NO:84). In some embodiments, the AAV capsid protein comprises a targeting sequence that comprises at least six contiguous amino acids from the sequence TVSALK (SEQ ID NO:4); TVSALFK (SEQ ID NO:8); KLASVT (SEQ ID NO:83); or KFLASVT (SEQ ID NO:84).

In some embodiments, the AAV is AAV9; other AAV as known in the art (e.g., AAV1, 2, 3, 4, 5, 6, 7, 8 and variants thereof and others as known in the art or described herein) can also be used.

In some embodiments, the AAV capsid protein comprises AAV9 VP1 (e.g., SEQ ID NO:85).

In some embodiments, the targeting sequence is inserted in the capsid protein at a position corresponding to between amino acids 588 and 589 of SEQ ID NO:85.

Also provided herein are nucleic acids encoding the AAV capsid proteins comprising a targeting sequence as described herein.

In addition, provided herein is an AAV comprising a capsid protein comprising a targeting sequence as described herein. In some embodiments, AAV further comprises a transgene, preferably a therapeutic or diagnostic transgene. Therapeutic transgenes can include, e.g., cDNAs that restore protein function, guide RNA for gene editing, RNA, or miRNA.

Also provided herein are targeting sequences comprising V[S/p][A/m/t/]L (SEQ ID NO:79), TV[S/p][A/m/t/]L (SEQ ID NO:80), TV[S/p][A/m/t/]LK (SEQ ID NO:81), or TV[S/p][A/m/t/]LFK. (SEQ ID NO:82). In some embodiments, the targeting sequence comprises VPALR (SEQ ID NO:1); VSALK (SEQ ID NO:2); TVPALR (SEQ ID NO:3); TVSALK (SEQ ID NO:4); TVPMLK (SEQ ID NO:12); TVPTLK (SEQ ID NO:13); FTVSALK (SEQ ID NO:5); LTVSALK (SEQ ID NO:6); TVSALFK (SEQ ID NO:8); TVPALFR (SEQ ID NO:9); TVPMLFK (SEQ ID NO:10) or TVPTLFK (SEQ ID NO:11). Also provided are fusion proteins comprising the targeting sequences linked to a heterologous (e.g., non-AAV VP1) sequence, and AAV capsid proteins (e.g., AAV9 VP1) comprising the targeting sequence. In some embodiments, the targeting sequence is inserted in a position corresponding to amino acids 588 and 589 of SEQ ID NO:85.

Additionally provided herein are nucleic acids encoding the targeting sequences, fusion proteins or AAV capsid proteins described herein, as well as AAV comprising the capsid proteins comprising a targeting sequence. In some embodiments, the AAV further comprises a transgene, preferably a therapeutic or diagnostic transgene. Therapeutic transgenes can include, e.g., cDNAs that restore protein function, guide RNA for gene editing, RNA, or miRNA.

Further, provided herein are methods of delivering a transgene to a cell, the method comprising contacting the cell with an AAV or fusion protein described herein. In some embodiments, the cell is in a living subject, e.g., a mammalian subject. In some embodiments, the cell is in a tissue selected from the brain, spinal cord, dorsal root ganglion, heart, or muscle, and a combination thereof. In some embodiments, the cell is a neuron (optionally a dorsal root ganglion neuron), astrocyte, cardiomyocyte, or myocyte.

In some embodiments, the subject has a neurodegenerative disease, epilepsy; stroke; spinocerebellar ataxia; Canavan's disease; Metachromatic leukodystrophy; Spinal muscular atrophy; Friedreich's ataxia; X-linked centronuclear myopathy; Lysosomal storage disease; Barth syndrome; Duchenne muscular dystrophy; Wilson's disease; or Crigler-Najjar syndrome type 1. In some embodiments, the neurodegenerative disease is Parkinson's disease; Alzheimer's disease; Huntington's disease; Amyotrophic lateral sclerosis; and Multiple sclerosis.

In some embodiments, the subject has a brain cancer, and the method includes administering an AAV encoding an anti-cancer agent. In some embodiments, the anti-cancer agent is HSV.TK1, and the method further comprises administering ganciclovir.

In some embodiments, the cell is in the brain of the subject, and the AAV is administered by parenteral delivery (e.g., via intravenous, intraarterial, subcutaneous, intraperitoneal, or intramuscular delivery); intracerebral; or intrathecal delivery (e.g., via lumbar injection, cisternal magna injection, or intraparenchymal injection).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a 3D model of an AAV9 virus. Individual CPP inserted into the capsid between amino acids 588 and 589 (VP1 numbering) will be displayed at the 3-fold axis where receptor binding presumably occurs. FIG. 1B illustrate the method of individual AAV production. Three plasmids including pRC (engineered or not), pHelper and pAAV are co-transfected into HEK 293T cells, with AAVs harvested and purified using iodixanol gradient.

In FIG. 2B, *P<0.05, vs. AAV9, ANOVA.

In FIG. 2D, *P<0.05, **P<0.01, vs. AAV9, ANOVA.

In FIG. 3C, *P<0.05, P<0.01, *P<0.001, vs. AAV9, ANOVA.

FIG. 4A illustrates the spheroid comprising human microvascular endothelial cells, which forms a barrier at the surface, and human pericyte and astrocytes inside the spheriod. Candidate AAVs were assessed for their ability to penetrate from the surrounding medium into the inside of the spheroid and to transduce the cells inside. FIG. 4B-4D shows images of AAV9, AAV.CPP.16 and AAV.CPP.21 treated spheroids. FIG. 4E shows relative RFP intensity of different AAV treated spheroids. ***P<0.001, vs. AAV9, ANOVA.

In FIG. 5B, *P<0.05, ***P<0.001, ANOVA.

In FIG. 6B, ***P<0.001, ANOVA.

In FIG. 7B, *P<0.05, Student test.

6J mice (6 weeks old). Percentage of RFP-labeled cells relative to all DAPI-stained cells is presented. *P<0.05, Student test.

Figure 9A:
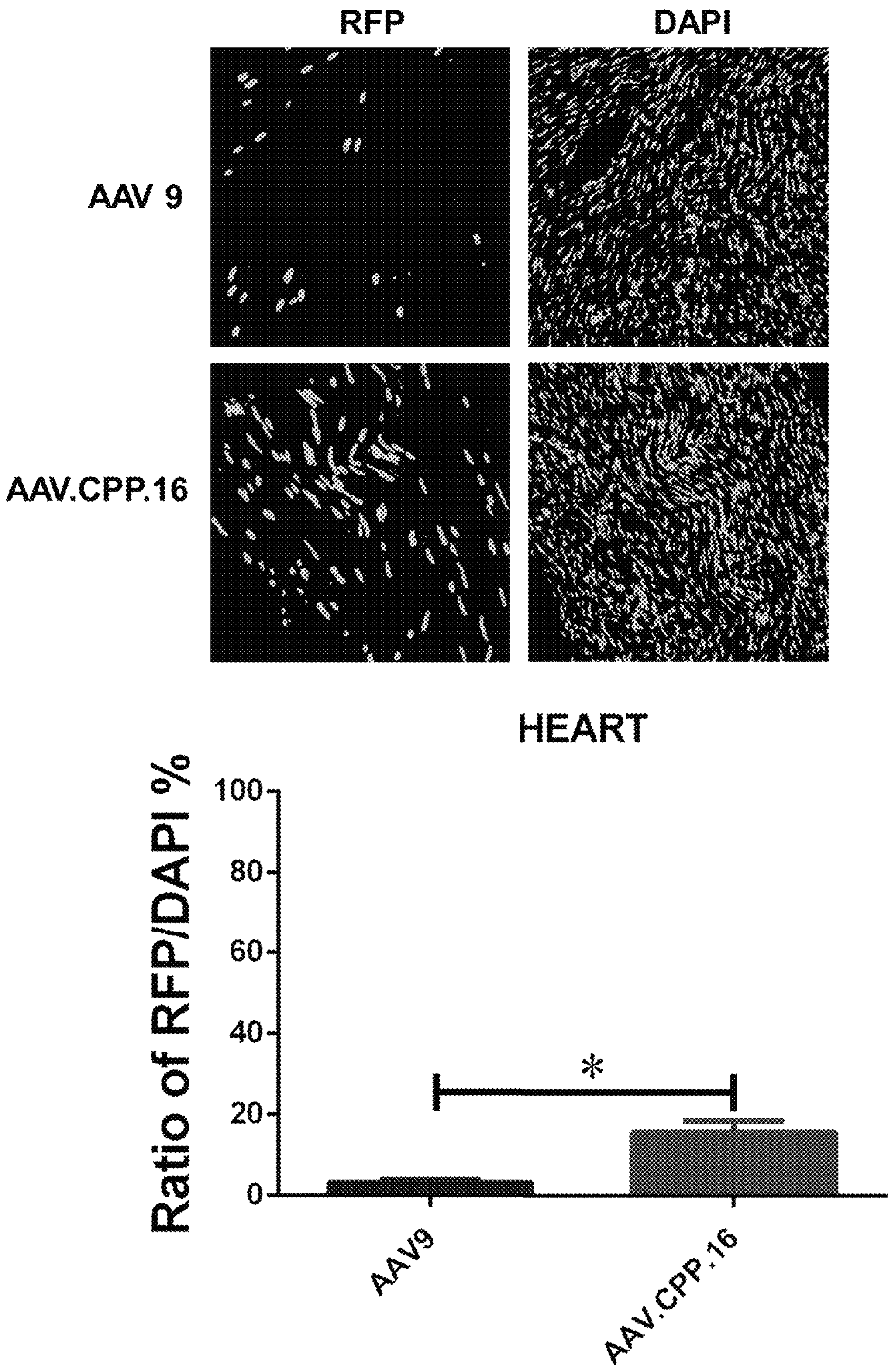
FIG. 9A depicts that AAV.CPP.16 shows enhanced ability vs. AAV9 in targeting the heart in adult mice. AAVs of $1\times10^{11}$ vg were administered intravenously in adult C57BL/
Figure 9B:
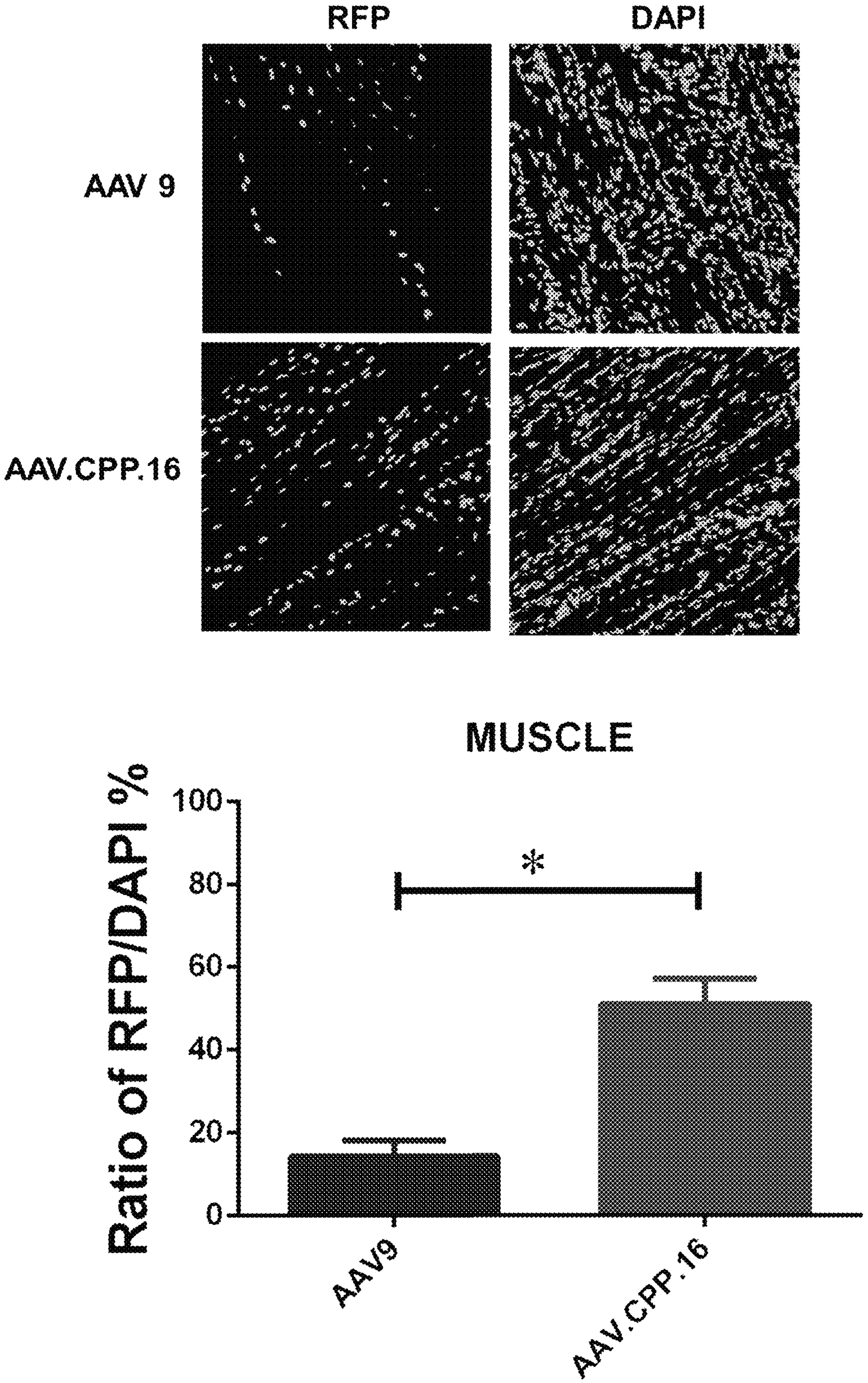

FIG. 9B depicts that AAV.CPP.16 shows enhanced ability vs. AAV9 in targeting the skeletal muscle in adult mice. AAVs of $1\times10^{11}$ vg were administered intravenously in adult C57BL/6J mice (6 weeks old). Percentage of RFP-labeled cells relative to all DAPI-stained cells is presented. *P<0.05, Student test.

Figure 9C:
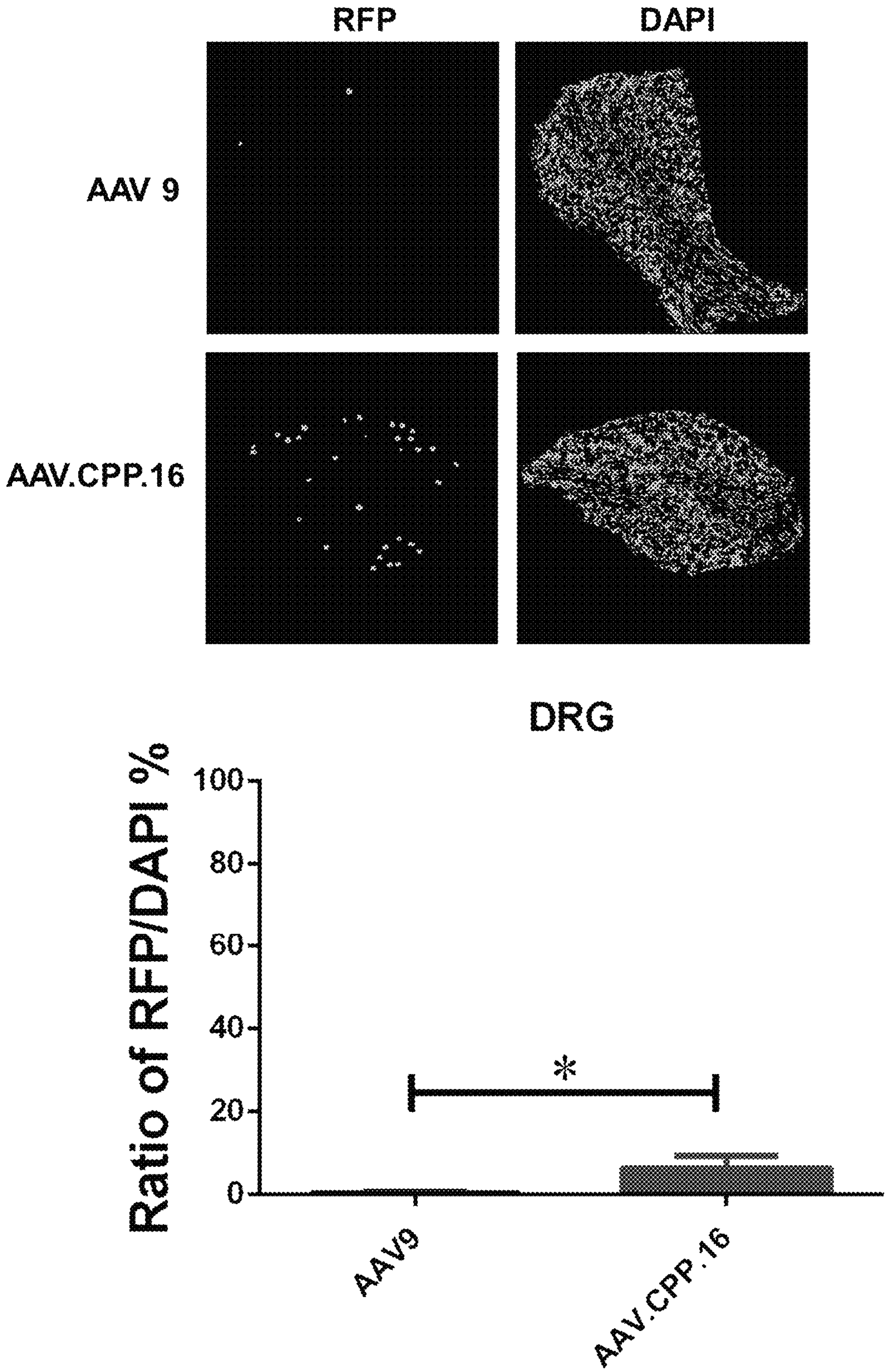

FIG. 9C depicts that AAV.CPP.16 shows enhanced ability vs. AAV9 in targeting the dorsal root ganglion (DRG) in adult mice. AAVs of $1\times10^{11}$ vg were administered intravenously in adult C57BL/6J mice (6 weeks old). Percentage of RFP-labeled cells relative to all DAPI-stained cells is presented. *P<0.05, Student test.

Figure 10A:
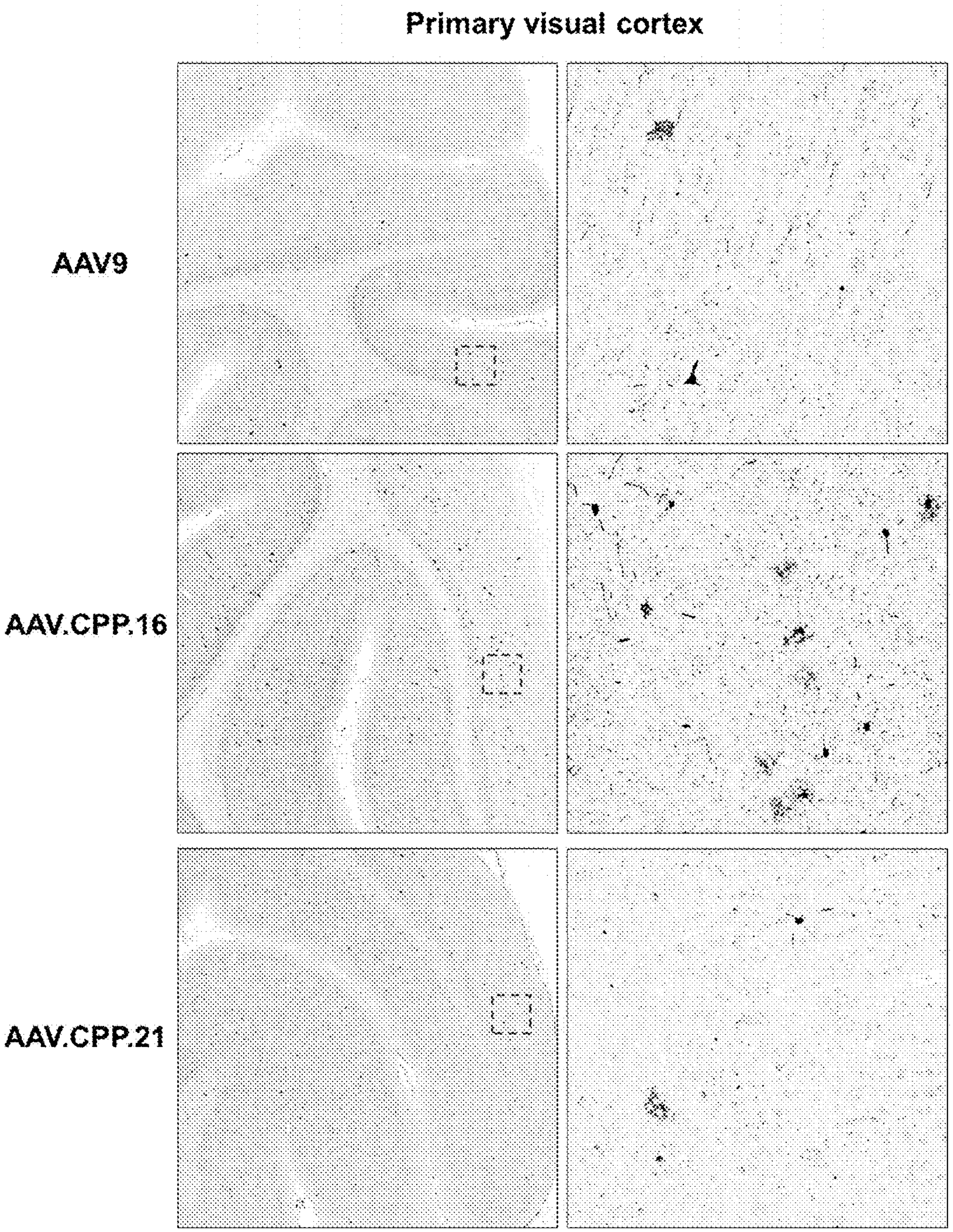

FIG. 10A depicts that AAV.CPP.16 and AAV.CPP.21 show enhanced ability vs. AAV9 to transduce brain cells in primary visual cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10B:
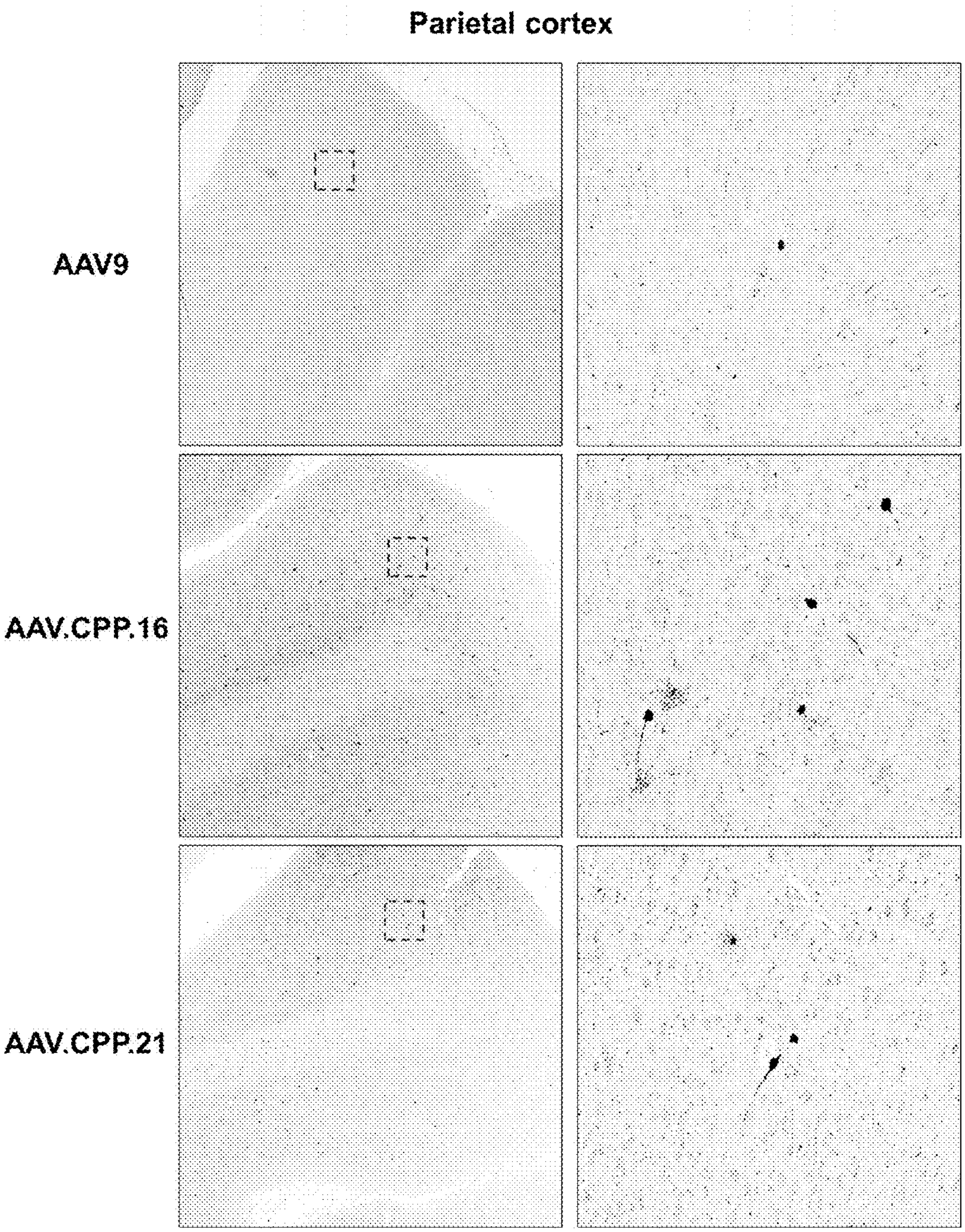

FIG. 10B depicts that AAV.CPP.16 and AAV.CPP.21 show enhanced ability vs. AAV9 to transduce brain cells in parietal cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10C:
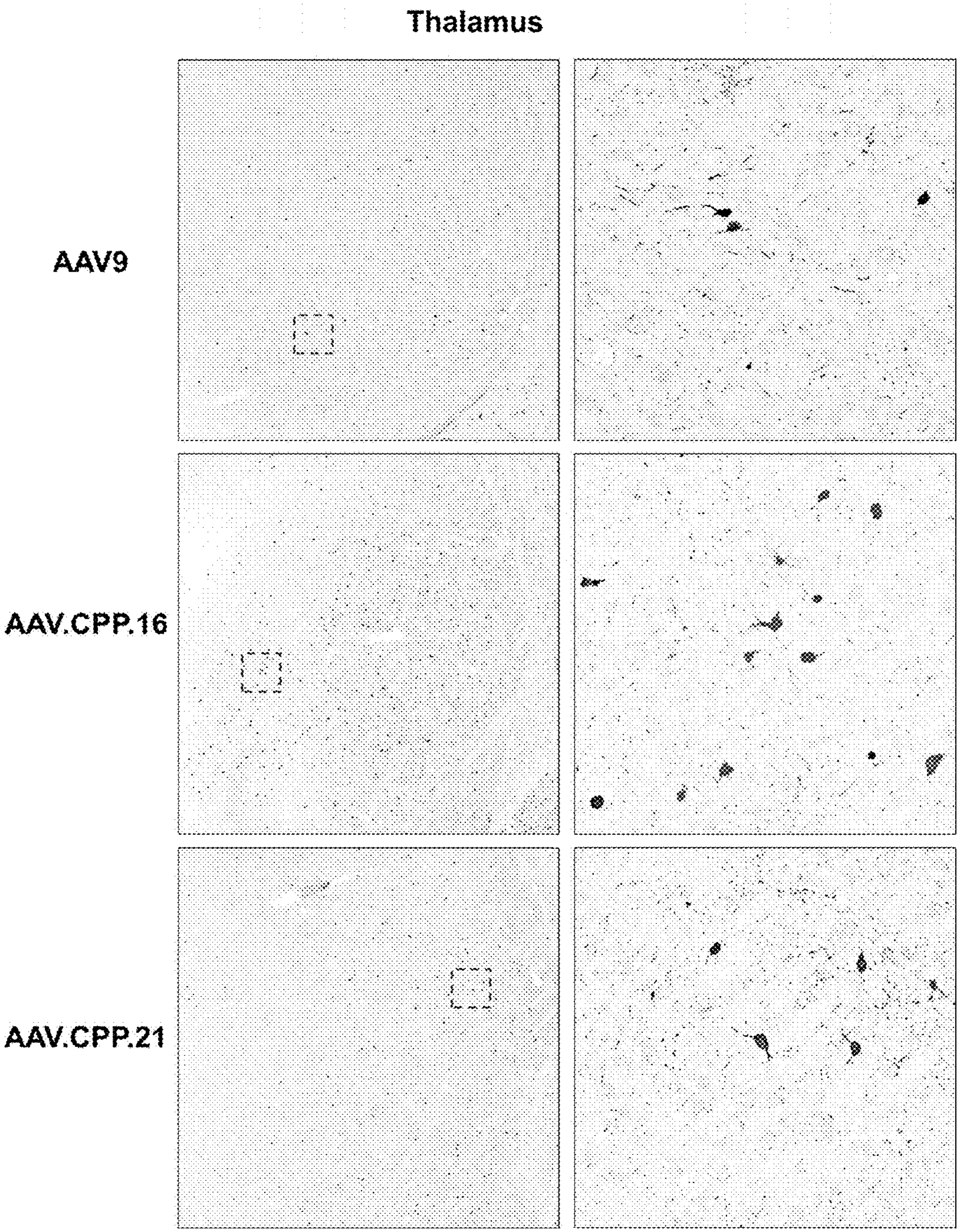

FIG. 10C depicts that AAV.CPP.16 and AAV.CPP.21 show enhanced ability vs. AAV9 to transduce brain cells in thalamus after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10D:
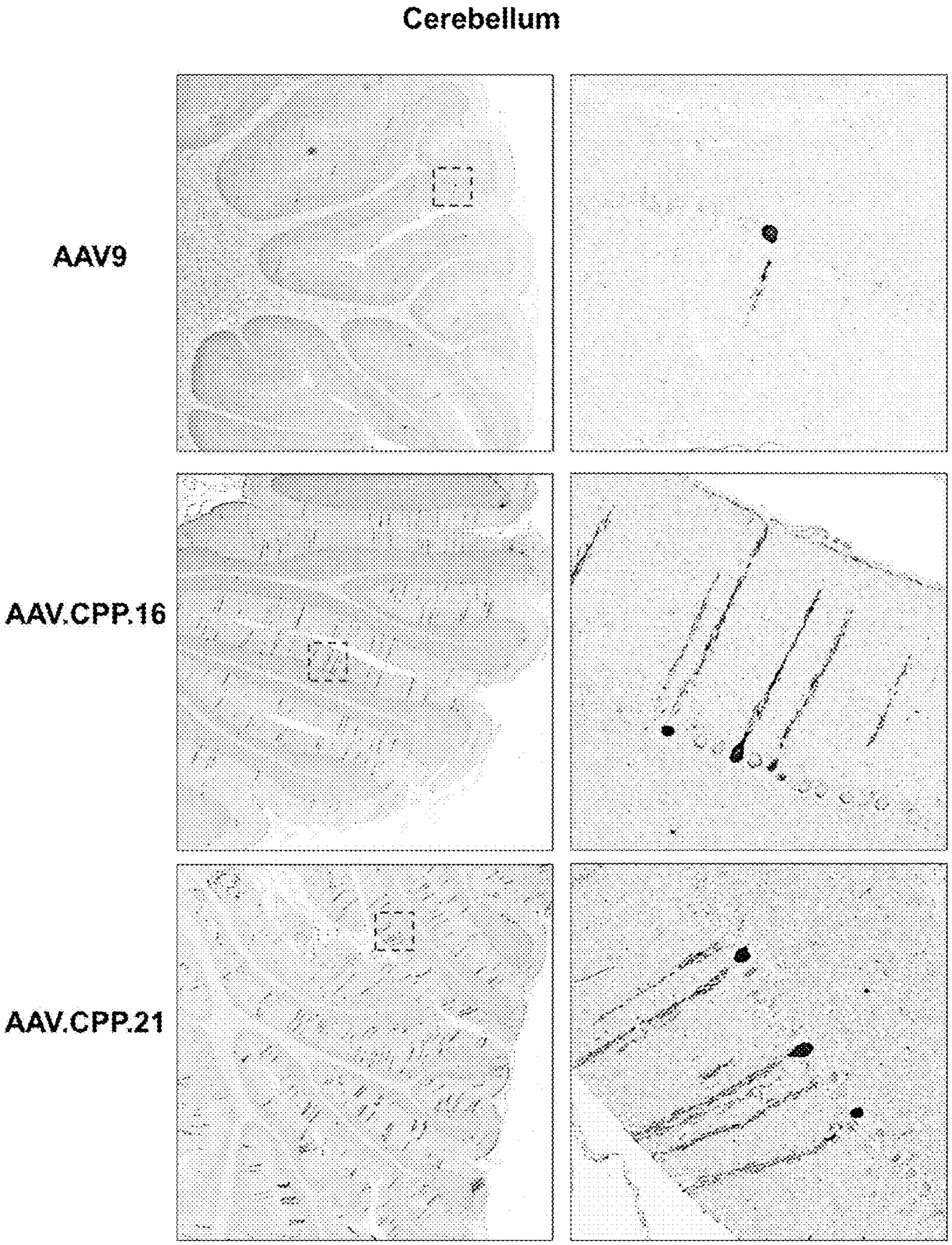

FIG. 10D depicts that AAV.CPP.16 and AAV.CPP.21 show enhanced ability vs. AAV9 to transduce brain cells in cerebellum after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. Both AAV.CPP.16 and AAV.CPP.21 transduced significantly more cells vs. AAV9.

Figure 11A:
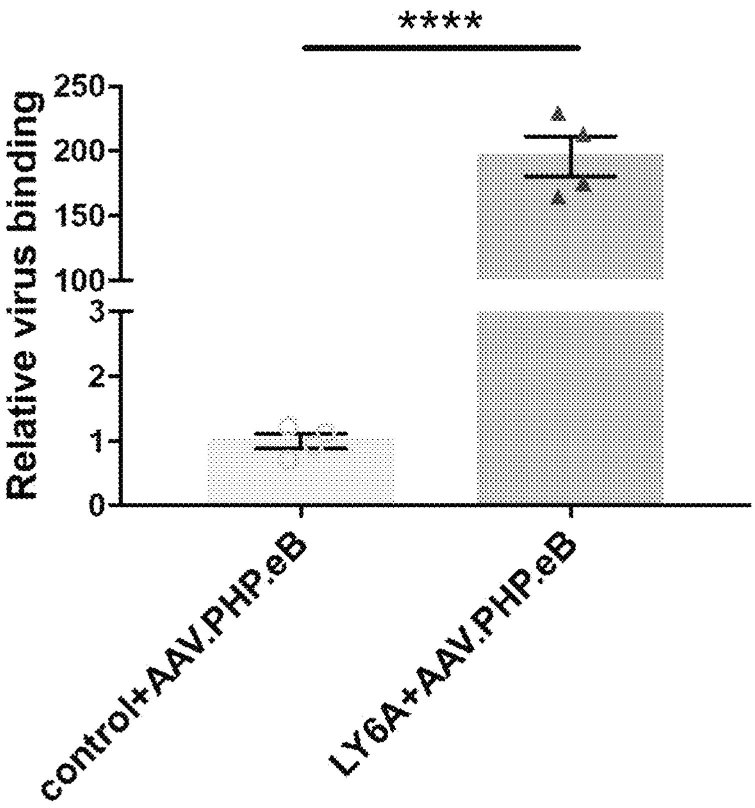
Figure 11B:
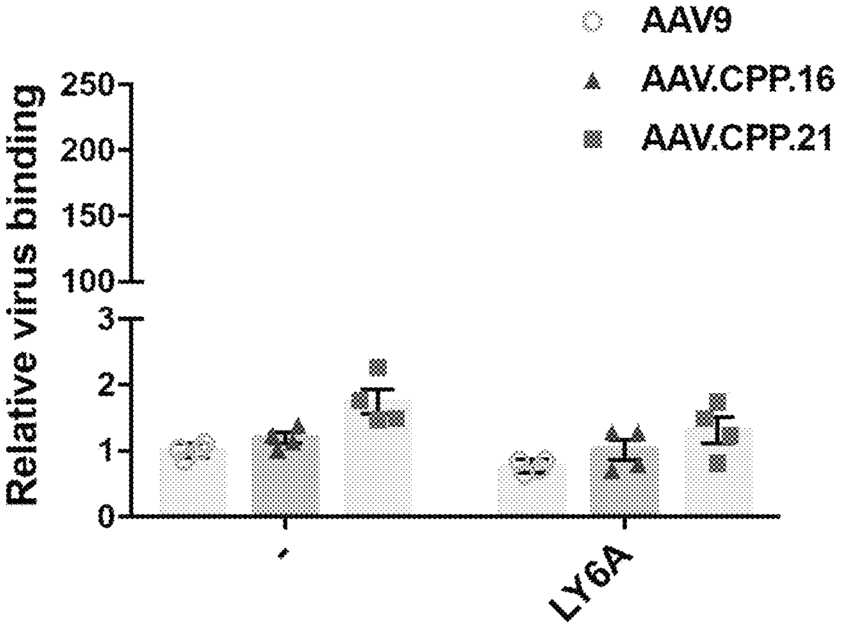

FIGS. 11A-11B depict that AAV.CPP.16 and AAV.CPP.21 do not bind to LY6A. LY6A serves as a receptor for AAV.PHP.B and its variants including AAV.PHP.eB (as in US9102949, US20170166926) and mediates AAV.PHP.eB's robust effect in crossing the BBB in certain mouse strains (Hordeaux et al. Mol Ther 2019 27(5):912-921; Huang et al. 2019, dx.doi.org/10.1101/538421). Over-expressing mouse LY6A in cultured 293 cells significantly increases binding of AAV.PHP.eB to the cell surface (FIG. 11A). On the contrary, over-expressing LY6A does not increase viral binding for AAV9, AAV.CPP.16 or AAV.CPP.21 (FIG. 11B). This suggests AAV.CPP.16 or AAV.CPP.21 does not share LY6A with AAV.PHP.eB as a receptor.

Figure 12A:
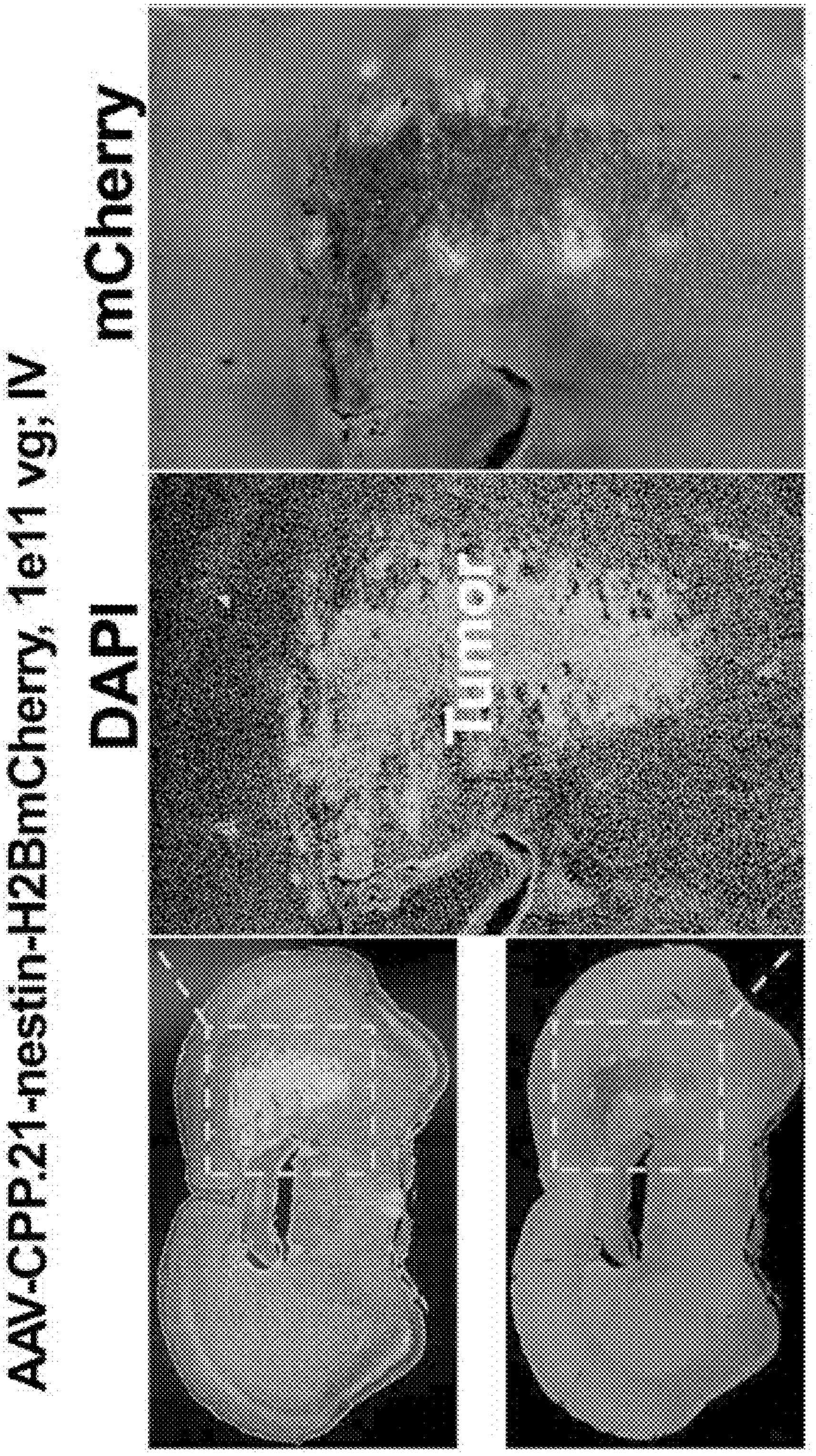
Figure 12B:
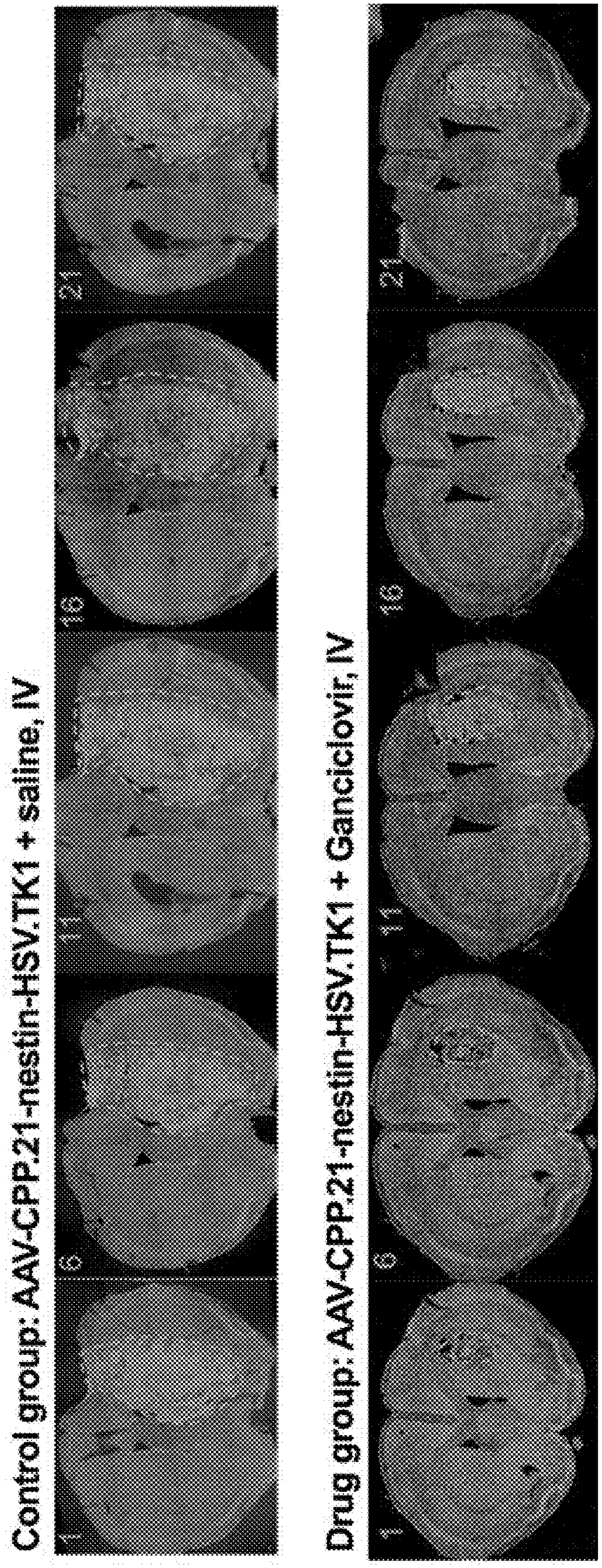
Figure 12C:
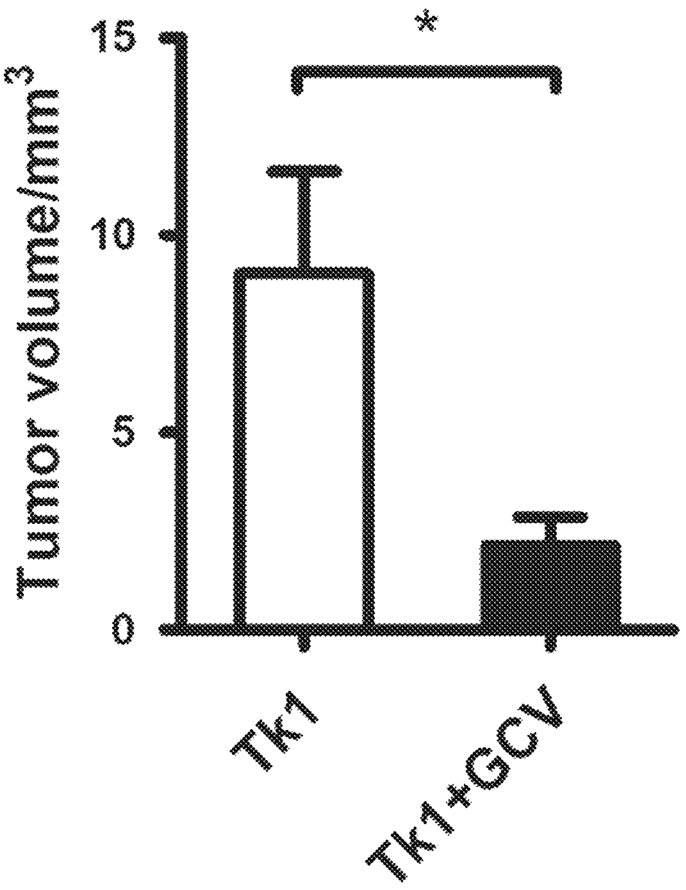

FIGS. 12A-12C depict that AAV.CPP.21 can be used to systemically deliver a therapeutic gene into brain tumor in a mouse mode of glioblastoma (GBM). In FIG. 12A, as in FIG. 11A, intravenously administered AAV.CPP.21-H2BmCherry was shown to target tumor mass, especially the tumor expanding frontier. In FIG. 12B-12C, using AAV.CPP.21 to systemically deliver the "suicide gene" HSV.TK1 results in shrinkage of brain tumor mass, when combined with the pro-drug ganciclovir. HSV.TK1 turns the otherwise "dormant" ganciclovir into a tumor-killing drug. *P<0.05, Student test.

Figure 13:
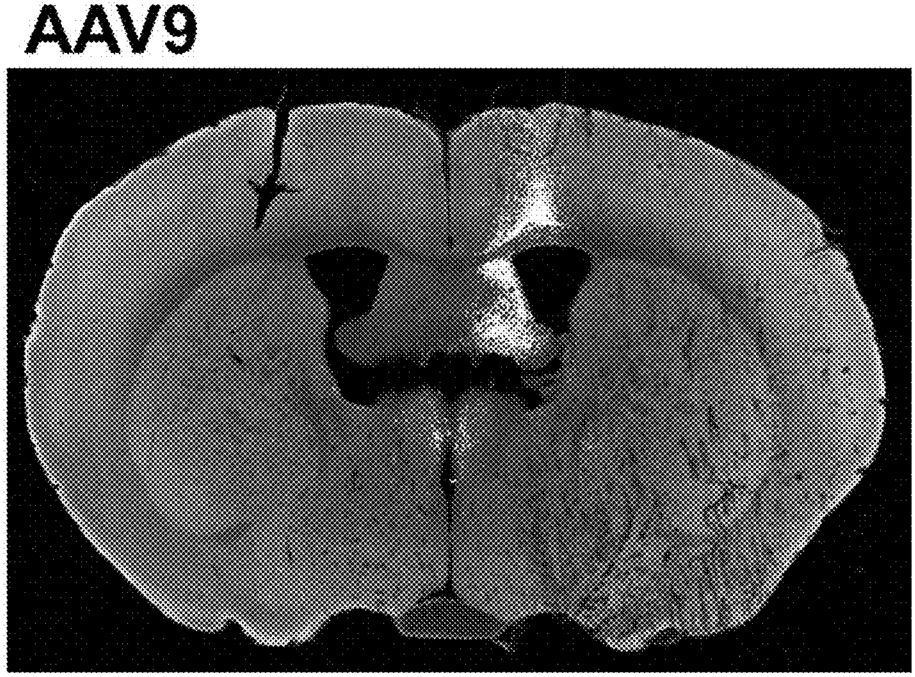
Figure 13:
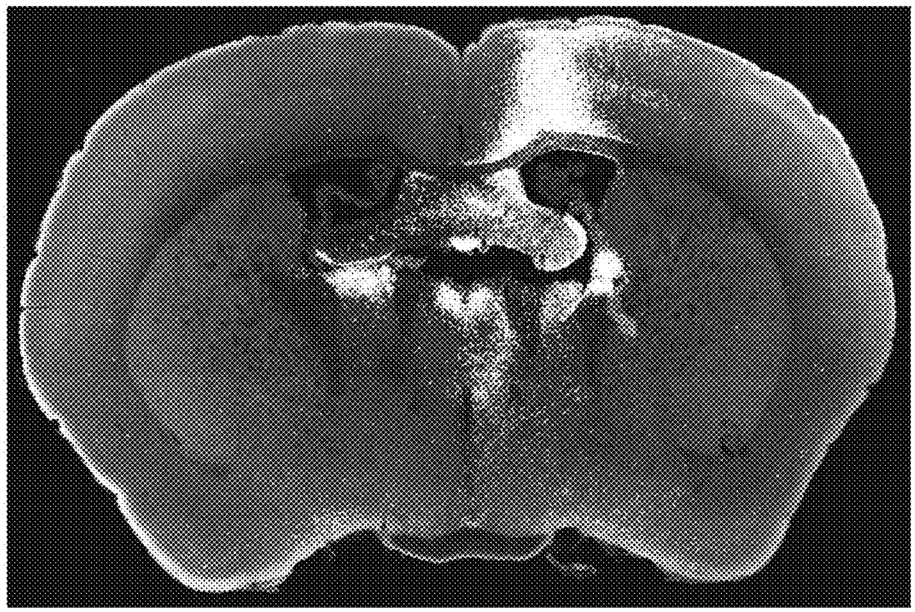

FIG. 13 depicts that when injected locally into adult mouse brain, AAV.CPP.21 resulted in more widespread and robust transduction of brain tissue in comparison with AAV9. Intracerebral injection of AAVs ($1\times10^{11}$ vg) was performed in adult mice (>6 weeks old) and brain tissues were harvested and examined 3 weeks after AAV injection. **P<0.01, Student test.

DETAILED DESCRIPTION

Difficulties associated with delivery across the BBB have hindered development of therapeutic agents to treat brain disorders including cancer and neurodegenerative disorders. Adeno-associated virus (AAV) has emerged as an important research and clinical tool for delivering therapeutic genes to the brain, spinal cord and the eye; see, e.g., U.S. Pat. Nos. 9,102,949; 9,585,971; and US20170166926. However, existing AAVs including AAV9 have either limited efficiency in crossing the BBB, or only work in some non-primate species.

Through rational design and targeted screening on the basis of known cell-penetrating peptides (CPPs) (see, e.g., Gomez et al., *Bax-inhibiting peptides derived from Ku70 and cell-penetrating pentapeptides*. Biochem. Soc. Trans. 2007; 35(Pt 4):797-801), targeting sequences have been discovered that, when engineered into the capsid of an AAV, improved the efficiency of gene delivery to the brain by up to three orders of magnitude. These methods were used to engineer one such AAV vector that dramatically reduced tumor size in an animal model of glioblastoma.

Targeting Sequences

The present methods identified a number of potential targeting peptides that enhance permeation through the BBB, e.g., when inserted into the capsid of an AAV, e.g., AAV1, AAV2, AAV8, or AAV9, or when conjugated to a biological agent, e.g., an antibody or other large biomolecule, either chemically or via expression as a fusion protein.

In some embodiments, the targeting peptides comprise sequences of at least 5 amino acids. In some embodiments, the amino acid sequence comprises at least 4, e.g., 5, contiguous amino acids of the sequences VPALR (SEQ ID NO:1) and VSALK (SEQ ID NO:2).

In some embodiments, the targeting peptides comprise a sequence of $X_1$ $X_2$ $X_3$ $X_4$ $X_5$, wherein:

(i) $X_1$, $X_2$, $X_3$, $X_4$ are any four non-identical amino acids of V, A, L, I, G, P, S, T, or M; and (ii) $X_5$ is K, R, H, D, or E (SEQ ID NO:73).

In some embodiments, the targeting peptides comprise sequences of at least 6 amino acids. In some embodiments, the amino acid sequence comprises at least 4, e.g., 5 or 6 contiguous amino acids of the sequences TVPALR (SEQ ID NO:3), TVSALK (SEQ ID NO:4), TVPMLK (SEQ ID NO:12) and TVPTLK (SEQ ID NO:13).

In some embodiments, the targeting peptides comprise a sequence of $X_1X_2$ $X_3$ $X_4$ $X_5$ $X_6$, wherein:

(i) $X_1$ is T;

(ii) $X_2$, $X_3$, $X_4$, $X_5$ are any four non-identical amino acids of V, A, L, I, G, P, S, T, or M; and (iii) $X_6$ is K, R, H, D, or E (SEQ ID NO:74).

In some embodiments, the targeting peptides comprise a sequence of $X_1X_2$ $X_3$ $X_4$ $X_5$ $X_6$, wherein:

(i) $X_1$, $X_2$, $X_3$, $X_4$ are any four non-identical amino acids from V, A, L, I, G, P, S, T, or M;

(ii) $X_5$ is K, R, H, D, or E; and (iii) $X_6$ is E or D (SEQ ID NO:75).

In some embodiments, the targeting peptides comprise sequences of at least 7 amino acids. In some embodiments, the amino acid sequence comprises at least 4, e.g., 5, 6, or 7 contiguous amino acids of the sequences FTVSALK (SEQ ID NO:5), LTVSALK (SEQ ID NO:6), TVSALFK (SEQ ID NO:8), TVPALFR (SEQ ID NO:9), TVPMLFK (SEQ ID NO:10) and TVPTLFK (SEQ ID NO:11). In some other embodiments, the targeting peptides comprise a sequence of $X_1$ $X_2$ $X_3$ $X_4$ $X_5$ $X_6$ $X_7$, wherein:

(i) $X_1$ is F, L, W, or Y;

(ii) $X_2$ is T;

(iii) $X_3$, $X_4$, $X_5$, $X_6$ are any four non-identical amino acids of V, A, L, I, G, P, S, T, or M; and (iv) $X_7$ is K, R, H, D, or E (SEQ ID NO:76).

In some embodiments, the targeting peptides comprise a sequence of $X_1X_2$ $X_3$ $X_4$ $X_5$ $X_6$ $X_7$, wherein:

(i) $X_1$ is T;

(ii) $X_2$, $X_3$, $X_4$, $X_5$ are any four non-identical amino acids of V, A, L, I, G, P, S, T, or M;

(iii) $X_6$ is K, R, H, D, or E; and (iv) $X_7$ is E or D (SEQ ID NO:77).

In some embodiments, the targeting peptides comprise a sequence of $X_1$ $X_2$ $X_3$ $X_4$ $X_5$ $X_6$ $X_7$, wherein:

(i) $X_1$, $X_2$, $X_3$, $X_4$ are any four non-identical amino acids of V, A, L, I, G, P, S, T, or M;

(ii) $X_5$ is K, R, H, D, or E;

(iii) $X_6$ is E or D; and (iv) $X_7$ is A or I (SEQ ID NO:78).

In some embodiments, the targeting peptides comprise a sequence of V[S/p][A/m/t/]L (SEQ ID NO:79), wherein the upper case letters are preferred at that position. In some embodiments, the targeting peptides comprise a sequence of TV[S/p][A/m/t/]L (SEQ ID NO:80). In some embodiments, the targeting peptides comprise a sequence of TV[S/p][A/m/t/]LK (SEQ ID NO:81). In some embodiments, the targeting peptides comprise a sequence of TV[S/p][A/m/t/]LFK. (SEQ ID NO:82).

In some embodiments, the targeting peptide does not consist of VPALR (SEQ ID NO:1) or VSALK (SEQ ID NO:2).

Specific exemplary amino acid sequences that include the above mentioned 5, 6, or 7-amino acid sequences are listed in Table 1.

TABLE 1

Targeting Sequences

| SEQ ID NO: | Targeting Peptide Sequence |
|---|---|
| 1. | VPALR |
| 2. | VSALK |
| 3. | TVPALR |
| 4. | **TVSALK** |
| 5. | FTVSALK |
| 6. | LTVSALK |
| 7. | TFVSALK |
| 8. | **TVSALFK** |
| 9. | TVPALFR |
| 10. | **TVPMLFK** |
| 11. | TVPTLFK |
| 12. | **TVPMLK** |
| 13. | TVPTLK |
| 14. | VPMLK |
| 15. | VPTLK |
| 16. | **VPMLKE** |
| 17. | VPTLKD |
| 18. | VPALRD |
| 19. | **VSALKE** |
| 20. | **VSALKD** |
| 21. | TAVSLK |
| 22. | TALVSK |
| 23. | TVLSAK |
| 24. | TLVSAK |
| 25. | TMVPLK |
| 26. | TMLVPK |
| 27. | TVLPMK |
| 28. | TLVPMK |
| 29. | TTVPLK |
| 30. | TTLVPK |
| 31. | TVLPTK |
| 32. | TLVPTK |
| 33. | TAVPLR |
| 34. | TALVPR |
| 35. | TVLPAR |
| 36. | TLVPAR |
| 37. | TAVSLKE |
| 38. | TALVSKE |

TABLE 1-continued

Targeting Sequences

| SEQ ID NO: | Targeting Peptide Sequence |
|---|---|
| 39. | TVLSAKE |
| 40. | TLVSAKE |
| 41. | TMVPLKE |
| 42. | TMLVPKE |
| 43. | TVLPMKE |
| 44. | TLVPMKE |
| 45. | TTVPLKD |
| 46. | TTLVPKD |
| 47. | TVLPTKD |
| 48. | TLVPTKD |
| 49. | TAVPLRD |
| 50. | TALVPRD |
| 51. | TVLPARD |
| 52. | TLVPARD |
| 53. | TAVSLFK |
| 54. | TALVSFK |
| 55. | TVLSAFK |
| 56. | TLVSAFK |
| 57. | TMVPLFK |
| 58. | TMLVPFK |
| 59. | TVLPMFK |
| 60. | TLVPMFK |
| 61. | TTVPLFK |
| 62. | TTLVPFK |
| 63. | TVLPTFK |
| 64. | TLVPTFK |
| 65. | TAVPLFR |
| 66. | TALVPFR |
| 67. | TVLPAFR |
| 68. | TLVPAFR |

Targeting peptides including reversed sequences can also be used, e.g., KLASVT (SEQ ID NO:83) and KFLASVT (SEQ ID NO:84).

Targeting peptides disclosed herein can be modified according to the methods known in the art for producing peptidomimetics. See, e.g., Qvit et al., Drug Discov Today. 2017 February; 22(2): 454-462; Farhadi and Hashemian, Drug Des Devel Ther. 2018; 12: 1239-1254; Avan et al., Chem. Soc. Rev., 2014, 43, 3575-3594; Pathak, et al., Indo American Journal of Pharmaceutical Research, 2015. 8; Kazmierski, W. M., ed., Peptidomimetics Protocols, Human Press (Totowa NJ 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include β-amino acids, β-substituted β-amino acids ("$\beta^3$-amino acids"), phosphorous analogs of amino acids, such as ∀-amino phosphonic acids and ∀-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. Exemplary retro-inverso targeting peptidomimetics include KLASVT and KFLASVT, wherein the sequences include all D-amino acids. These sequences can be modified, e.g., by biotinylation of the amino terminus and amidation of the carboxy terminus.

AAVs

Viral vectors for use in the present methods and compositions include recombinant retroviruses, adenovirus, adeno-associated virus, alphavirus, and lentivirus, comprising the targeting peptides described herein and optionally a transgene for expression in a target tissue.

A preferred viral vector system useful for delivery of nucleic acids in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

There are numerous alternative AAV variants (over 100 have been cloned), and AAV variants have been identified based on desirable characteristics. In some embodiments, the AAV is AAV1, AAV2, AAV4, AAV5, AAV6, AV6.2, AAV7, AAV8, AAV9, rh.10, rh.39, rh.43 or CSp3; for CNS use, in some embodiments the AAV is AAV1, AAV2, AAV4, AAV5, AAV6, AAV8, or AAV9. As one example, AAV9 has been shown to somewhat efficiently cross the blood-brain barrier. Using the present methods, the AAV capsid can be genetically engineered to increase permeation across the BBB, or into a specific tissue, by insertion of a targeting sequence as described herein into the capsid protein, e.g., into the AAV9 capsid protein VP1 between amino acids 588 and 589.

An exemplary wild type AAV9 capsid protein VP1 (Q6JC40-1) sequence is as follows:

```
                                    (SEQ ID NO: 85)
        10         20         30         40
MAADGYLPDW LEDNLSEGIR EWWALKPGAP QPKANQQHQD

        50         60         70         80
NARGLVLPGY KYLGPGNGLD KGEPVNAADA AALEHDKAYD

        90        100        110        120
QQLKAGDNPY LKYNHADAEF QERLKEDTSF GGNLGRAVFQ

       130        140        150        160
AKKRLLEPLG LVEEAAKTAP GKKRPVEQSP QEPDSSAGIG

       170        180        190        200
KSGAQPAKKR LNFGQTGDTE SVPDPQPIGE PPAAPSGVGS

       210        220        230        240
LTMASGGGAP VADNNEGADG VGSSSGNWHC DSQWLGDRVI

       250        260        270        280
TTSTRTWALP TYNNHLYKQI SNSTSGGSSN DNAYFGYSTP

       290        300        310        320
WGYFDFNRFH CHFSPRDWQR LINNNWGFRP KRLNFKLFNI

       330        340        350        360
QVKEVTDNNG VKTIANNLTS TVQVFTDSDY QLPYVLGSAH

       370        380        390        400
EGCLPPFPAD VFMIPQYGYL TLNDGSQAVG RSSFYCLEYF

       410        420        430        440
PSQMLRTGNN FQFSYEFENV PFHSSYAHSQ SLDRLMNPLI

       450        460        470        480
DQYLYYLSKT INGSGQNQQT LKFSVAGPSN MAVQGRNYIP

       490        500        510        520
GPSYRQQRVS TTVTQNNNSE FAWPGASSWA LNGRNSLMNP

       530        540        550        560
GPAMASHKEG EDRFFPLSGS LIFGKQGTGR DNVDADKVMI

       570        580        590        600
TNEEEIKTTN PVATESYGQV ATNHQSAQAQ AQTGWVQNQG

       610        620        630        640
ILPGMVWQDR DVYLQGPIWA KIPHTDGNFH PSPLMGGFGM

       650        660        670        680
KHPPPQILIK NTPVPADPPT AFNKDKLNSF ITQYSTGQVS

       690        700        710        720
VEIEWELQKE NSKRWNPEIQ YTSNYYKSNN VEFAVNTEGV

       730
YSEPRPIGTR YLTRNL
```

Thus provided herein are AAV that include one or more of the targeting peptide sequences described herein, e.g., an AAV comprising a capsid protein comprising a targeting sequence described herein, e.g., a capsid protein comprising SEQ ID NO:1 wherein a targeting peptide sequence has been inserted into the sequence, e.g., between amino acids 588 and 589.

In some embodiments, the AAV also includes a transgene sequence (i.e., a heterologous sequence), e.g., a transgene encoding a therapeutic agent, e.g., as described herein or as known in the art, or a reporter protein, e.g., a fluorescent protein, an enzyme that catalyzes a reaction yielding a detectable product, or a cell surface antigen. The transgene is preferably linked to sequences that promote/drive expression of the transgene in the target tissue.

Exemplary transgenes for use as therapeutics include neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), amino acid decorboxylase (AADC), aspartoacylase (ASPA), blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble VEGF receptors, soluble interleukin receptors (e.g., soluble IL-1 receptors and soluble type II IL-1 receptors), soluble gamma/delta T cell receptors, ligand-binding fragments of a soluble receptor, and the like; enzymes, such as α-glucosidase, imiglucarase, β-glucocerebrosidase, and alglucerase; enzyme activators, such as tissue plasminogen activator; chemokines, such as IP-10, monokine induced by interferon-gamma (Mig), Groa/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitryp sin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other examples of protein of interest include ciliary neurotrophic factor (CNTF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

The transgene can also encode an antibody, e.g., an immune checkpoint inhibitory antibody, e.g., to PD-L1, PD-1, CTLA-4 (Cytotoxic T-Lymphocyte-Associated Protein-4; CD152); LAG-3 (Lymphocyte Activation Gene 3; CD223); TIM-3 (T-cell Immunoglobulin domain and Mucin domain 3; HAVCR2); TIGIT (T-cell Immunoreceptor with Ig and ITIM domains); B7-H3 (CD276); VSIR (V-set immunoregulatory receptor, aka VISTA, B7H5, C10orf54); BTLA 30 (B- and T-Lymphocyte Attenuator, CD272); GARP (Glycoprotein A Repetitions; Predominant; PVRIG (PVR related immunoglobulin domain containing); or VTCN1 (Vset domain containing T cell activation inhibitor 1, aka B7-H4).

Other transgenes can include small or inhibitory nucleic acids that alter/reduce expression of a target gene, e.g., siRNA, shRNA, miRNA, antisense oligos, or long non-coding RNAs that alter gene expression (see, e.g., WO2012087983 and US20140142160), or CRISPR Cas9/cas12a and guide RNAs.

The virus can also include one or more sequences that promote expression of a transgene, e.g., one or more promoter sequences; enhancer sequences, e.g., 5' untranslated region (UTR) or a 3' UTR; a polyadenylation site; and/or insulator sequences. In some embodiments, the promoter is a brain tissue specific promoter, e.g.,a neuron-specific or glia-specific promoter. In certain embodiments, the promoter is a promoter of a gene selected to from: neuronal nuclei (NeuN), glial fibrillary acidic protein (GFAP), MeCP2, adenomatous polyposis coli (APC), ionized calcium-binding adapter molecule 1 (Iba-1), synapsin I (SYN), calcium/calmodulin-dependent protein kinase II, tubulin alpha I, neuron-specific enolase and platelet-derived growth factor beta chain. In some embodiments, the promoter is a pan-cell type promoter, e.g., cytomegalovirus (CMV), beta glucuronidase, (GUSB), ubiquitin C (UBC), or rous sarcoma virus (RSV) promoter. The woodchuck hepatitis virus post-transcriptional response element (WPRE) can also be used.

In some embodiments, the AAV also has one or more additional mutations that increase delivery to the target tissue, e.g., the CNS, or that reduce off-tissue targeting, e.g., mutations that decrease liver delivery when CNS, heart, or muscle delivery is intended (e.g., as described in Pulicherla et al. (2011) Mol Ther 19:1070-1078); or the addition of other targeting peptides, e.g., as described in Chen et al. (2008) Nat Med 15:1215-1218 or Xu et al., (2005) Virology 341:203-214 or U.S. Pat. Nos. 9,102,949; 9,585,971; and US20170166926. See also Gray and Samulski (2011) "Vector design and considerations for CNS applications," in Gene Vector Design and Application to Treat Nervous System Disorders ed. Glorioso J., editor. (Washington, DC: Society for Neuroscience;) 1-9, available at sfn.org/~/media/SfN/Documents/Short%20Courses/2011%20Short%20Course%20I/2 011_SC1_Gray.ashx.

Targeting Peptides as Tags/Fusions

The targeting peptides described herein can also be used to increase permeation of other (heterologous) molecules across the BBB, e.g., by conjugation to the molecule, or by expression as part of a fusion protein, e.g., with an antibody or other large biomolecule. These can include genome editing proteins or complexes (e.g., TALEs, ZFNs, Base editors, and CRISPR RNPs comprising a gene editing protein such as Cas9 or Cas12a, fused to a peptide described herein (e.g., at the N terminus, C terminus, or internally) and a guide RNA), in addition to therapeutic agents or reporters as described herein as well as those listed in Table 2. The fusions/complexes do not comprise any other sequences from Ku70, e.g., comprise heterologous non-Ku70 sequences, and are not present in nature.

In some embodiments, targeting sequences used as part of a non-AAV fusion protein do not comprise or consist of VPALR (SEQ ID NO:1) or VSALK (SEQ ID NO:2).

Methods of Use

The methods and compositions described herein can be used to deliver any composition, e.g., a sequence of interest to a tissue, e.g., to the central nervous system (brain), heart, muscle, or dorsal root ganglion or spinal cord (peripheral nervous system). In some embodiments, the methods include delivery to specific brain regions, e.g., cortex, cerebellum, hippocampus, substantia nigra, amygdala. In some embodiments, the methods include delivery to neurons, astrocytes, glial cells, or cardiomyocytes.

In some embodiments, the methods and compositions, e.g., AAVs, are used to deliver a nucleic acid sequence to a subject who has a disease, e.g., a disease of the CNS; see, e.g., U.S. Pat. Nos. 9,102,949; 9,585,971; and US20170166926. In some embodiments, the subject has a condition listed in Table 2; in some embodiments, the vectors are used to deliver a therapeutic agent listed in Table 2 for treating the corresponding disease listed in Table 2. The therapeutic agent can be delivered as a nucleic acid, e.g. via a viral vector, wherein the nucleic acid encodes a therapeutic protein or other nucleic acid such as an antisense oligo, siRNA, shRNA, and so on; or as a fusion protein/complex with a targeting peptide as described herein.

TABLE 2

| Diseases | | |
|---|---|---|
| Examples of diseases | Tissue targeted | Therapeutic agent |
| Parkinson's disease | CNS | GDNF, AADC |
| Alzheimer's disease | CNS | Tau antibody, APP antibody |
| Huntington's disease | CNS | miRNA targeting HTT |
| Amyotrophic lateral sclerosis | CNS | shRNA targeting SOD |
| Multiple sclerosis | CNS | IFN-beta |
| Epilepsy | CNS | Neuropeptide Y |
| Stroke | CNS | IGF-1, osteopontin |
| Brain cancer | CNS | HSV.TK1, PD-1/PD-L1 antibody |
| Spinocerebellar ataxia | CNS | RNAi targeting ataxin |
| Canavan disease | CNS | ASPA |
| Metachromatic leukodystrophy | Nervous systems | ARSA, PSAP |
| Spinal muscular atrophy | Neuromuscular system | SMN1 |
| Friedreich's ataxia | Nervous systems, heart | Frataxin |
| X-linked myotubular myopathy | Neuromuscular system | MTM1 |
| Pompe disease | Lysosome (global including CNS) | GAA |
| Barth syndrome | Heart, muscle | TAZ |
| Duchenne muscular dystrophy | Muscle | dystrophin |
| Wilson's disease | Brain, liver | ATP7B |
| Crigler-Najjar syndrome type 1 | Liver | UGT1A1 |

In some embodiments, the compositions and methods are used to treat brain cancer. Brain cancers include gliomas (e.g., glioblastoma multiforme (GBM)), metastases (e.g., from lung, breast, melanoma, or colon cancer), meningiomas, pituitary adenomas, and acoustic neuromas. The compositions include a targeting peptide linked to an anticancer agent, e.g., a "suicide gene" that induces apoptosis in a target cell (e.g., HSV.TK1, Cytosine Deaminase (CD) from Herpes simplex virus or *Escherichia coli*, or *Escherichia coli* purine nucleoside phosphorylase (PNP)/fludarabine; see Krohne et al., Hepatology. 2001 September; 34(3):511-8; Dey and Evans, "Suicide Gene Therapy by Herpes Simplex Virus-1 Thymidine Kinase (HSV-TK)" (2011) DOI: 10.5772/18544) an immune checkpoint inhibitory antibody as known in the art or described herein. For example, an AAV vector comprising a targeting peptide as described herein can be used to deliver the "suicide gene" HSV.TK1 to a brain tumor. HSV.TK1 turns the otherwise "dormant" ganciclovir into a tumor-killing drug. Thus the methods can include systemically, e.g., intravenously, administering an AAV (e.g., AAV9) comprising a targeting peptide as described herein and encoding HSV.TK1, and the pro-drug ganciclovir, to a subject who has been diagnosed with brain cancer.

Pharmaceutical Compositions and Methods of Administration

The methods described herein include the use of pharmaceutical compositions comprising the targeting peptides as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intraarterial, subcutaneous, intraperitoneal intramuscular or injection or infusion administration. Delivery can thus be systemic or localized.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY.). For example, solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a kit, container, pack, or dispenser together with instructions for administration. For example, the compositions comprising an AAV comprising a targeting peptide as described herein and a nucleic acid encoding HSV.TK1 can be provided in a kit with ganciclovir.

EXAMPLES

The invention is further described in the following examples, which do not limit the scope of the invention described in the claims.

Materials and Methods

The following materials and methods were used in the Examples below.

1. Generation of Capsid Variants

To generate the capsid variant plasmids, DNA fragments that encode the cell-penetrating peptides (Table 3) were synthesized (GenScript), and inserted into the backbone of the AAV9 Rep-cap plasmid (pRC9) between amino acid position 588 and 589 (VP1 amino acid numbering), using CloneEZ seamless cloning technology (GenScript). CPPs BIP1 (VPALR, SEQ ID NO:1) and BIP2 (VSALK, SEQ ID NO:2), as well as their derivatives such as TVSALK (SEQ ID NO:4) in AAV.CPP.16 and TVSALFK (SEQ ID NO:8) in AAV.CPP.21, are derived from the Ku70 proteins, of which the sequences are provided as below:

```
Human Ku70  MSGWESYYKTEGDEEAEEEQEENLEASGDYKYSGRDSLIFLVDASKAMFESQSEDELTPF 60
Mouse Ku70  MSEWESYYKTEGEEEEEE--EESPDTGGEYKYSGRDSLIFLVDASRAMFESQGEDELTPE 58
Rat Ku70    MSEWESYYKTEGEEEEEE--EQSPDTNGEYKYSGRDSLIFLVDASRAMFESQGEDELTPE 58

Human Ku70  DMSIQCIQSVYISKIISSDRDLLAVVFYGTEKDKNSVNFKNIYVLQELDNPGAKRILELD 120
Mouse Ku70  DMSIQCIQSVYTSKIISSDRDLLAVVFYGTEKDKNSVNFKNIYVLQDLDNPGAKRVLELD 118
Rat Ku70    DMSIQCIQSVYTSKIISSDRDLLAVVFYGTEKDKNSVNFKSIYVLQDLDNPGAKRVLELD 118

Human Ku70  QFKGQQGQKRFQDMMGHGSDYSLSEVLWVCANLFSDVQFKMSHKRIMLFTNEDNPHGNDS 180
Mouse Ku70  QFKGQQGKKHFRDTVGHGSDYSLSEVLWVCANLFSDVQLKMSHKRIMLFTNEDDPHGRDS 178
Rat Ku70    RFKGQQGKKHFRDTIGHGSDYSLSEVLWVCANLFSDVQFKMSHKRIMLFTNEDDPHGNDS 178

Human Ku70  AKASRARTKAGDLRDTGIFLDLMHLKKPGGFDISLFYRDIISIAEDEDLRVHFEESSKLE 240
Mouse Ku70  AKASRARTKASDLRDTGIFLDLMHLKKPGGFDVSVFYRDIITTAEDEDLGVHFEESSKLE 238
Rat Ku70    AKASRARTKASDLRDTGIFLDLMHLKKRGGFDVSLFYRDIISIAEDEDLGVHFEESSKLE 238

Human Ku70  DLLRKVRAKETRKRALSRLKLKLNKDIVISVGIYNLVQKALKPPPIKLYRETNEPVKTKT 300
Mouse Ku70  DLLRKVRAKETKKRVLSRLKFKLGEDVVLMVGIYNLVQKANKPFPVRLYRETNEPVKTKT 298
Rat Ku70    DLLRKVRAKETKKRVLSRLKFKLGKDVALMVGVYNLVQKANKPFPVRLYRETNEPVKTKT 298

Human Ku70  RTFNTSTGGLLLPSDTKRSQIYGSRQIILEKEETEELKRFDDPGLMLMGFKPLVLLKKHH 360
Mouse Ku70  RTFNVNTGSLLLPSDTKRSLTYGTRQIVLEKEETEELKRFDEPGLILMGFKPTVMLKKQH 358
Rat Ku70    RTFNVNTGSLLLPSDTKRSLTFGTRQIVIEKEETEELKRFDEPGLILMGFKPMVMLKNHH 358

Human Ku70  YLRPSLFVYPEESLVIGSSTLFSALLIKCLEKEVAALCRYTPRRNIPPYFVALVPQEEEL 420
Mouse Ku70  YLRPSLFVYPEESLVSGSSTLFSALLTKCVEKEVIAVCRYTPRKNVSPYFVALVPQEEEL 418
Rat Ku70    YLRPSLFLYPEESLVNGSSTLFSALLTKCVEKEVIAVCRYTARKNVSPYFVALVPQEEEL 418

Human Ku70  DDQKIQVTPPGFQLVFLPFADDKRKMPFTEKIMATPEQVGKMKAIVEKLRFTYRSDSFEN 480
Mouse Ku70  DDQNIQVTPGGFQLVFLPYADDKRKVPFTEKVTANQEQIDKMKAIVQKLRFTYRSDSFEN 478
Rat Ku70    DDQNIQVTPAGFQLVFLPYADDKRKVPFTEKVMANPEQIDKMKAIVQKLRFTYRSDSFEN 478

Human Ku70  PVLQQHFRNLEALALDLMEPEQAVDLTLPKVEAMNKRLGSLVDEFKELVYPPDYNPEGKV 540
Mouse Ku70  PVLQQHFRNLEALALDMMESEQVVDLTLPKVEAIKKRLGSLADEFKELVYPPGYNPEGKV 538
Rat Ku70    PVLQQHFRNLEALALDMMESEQVVDLTLPKVEAIKKRLGSLADEFKELVYPPGYNPEGKI 538

Human Ku70  TKRKHDNEGSGSKRPKVEYSEEELKTHISKGTLGKFTVPMLKEACRAYGLKSGLKKQELL 600
Mouse Ku70  AKRKQDDEGSTSKKPKVELSEEELKAHFRKGTLGKLTVPTLKDICKAHGLKSGPKKQELL 598
Rat Ku70    AKRKADNEGSASKKPKVELSEEELKDLFAKGTLGKLTVPALRDICKAYGLKSGPKKQELL 598

Human Ku70  EALTKHFQD- 609      (SEQ ID NO: 86)
Mouse Ku70  DALIRHLEKN 608      (SEQ ID NO: 87)
Rat Ku70    EALSRHLEKN 608      (SEQ ID NO: 88)
```

In addition, VP1 protein sequences for AAV9, AAV.CPP.16 and AAV.CPP.21 are provided as below:

```
AAV9        MAADGYLPDWLEDNLSEGIREWWALKPGAPQPKANQQHQDNARGLVLPGYKYLGPGNGLD 60
AAV.CPP16   MAADGYLPDWLEDNLSEGIREWWALKPGAPQPKANQQHQDNARGLVLPGYKYLGPGNGLD 60
AAV.CPP21   MAADGYLPDWLEDNLSEGIREWWALKPGAPQPKANQQHQDNARGLVLPGYKYLGPGNGLD 60

AAV9        KGEPVNAADAAALEHDKAYDQQLKAGDNPYLKYNHADAEFQERLKEDTSFGGNLGRAVFQ 120
AAV.CPP16   KGEPVNAADAAALEHDKAYDQQLKAGDNPYLKYNHADAEFQERLKEDTSFGGNLGRAVFQ 120
AAV.CPP21   KGEPVNAADAAALEHDKAYDQQLKAGDNPYLKYNHADAEFQERLKEDTSFGGNLGRAVFQ 120

AAV9        AKKRLLEPLGLVEEAAKTAPGKKRPVEQSPQEPDSSAGIGKSGAQPAKKRLNFGQTGDTE 180
AAV.CPP16   AKKRLLEPLGLVEEAAKTAPGKKRPVEQSPQEPDSSAGIGKSGAQPAKKRLNFGQTGDTE 180
AAV.CPP21   AKKRLLEPLGLVEEAAKTAPGKKRPVEQSPQEPDSSAGIGKSGAQPAKKRLNFGQTGDTE 180

AAV9        SVPDPQPIGEPPAAPSGVGSLTMASGGGAPVADNNEGADGVGSSSGNWHCDSQWLGDRVI
AAV.CPP16   SVPDPQPIGEPPAAPSGVGSLTMASGGGAPVADNNEGADGVGSSSGNWHCDSQWLGDRVI 240
AAV.CPP21   SVPDPQPIGEPPAAPSGVGSLTMASGGGAPVADNNEGADGVGSSSGNWHCDSQWLGDRVI 240

AAV9        TTSTRTWALPTYNNHLYKQISNSTSGGSSNDNAYFGYSTPWGYFDFNRFHCHFSPRDWQR 300
AAV.CPP16   TTSTRTWALPTYNNHLYKQISNSTSGGSSNDNAYFGYSTPWGYFDFNRFHCHFSPRDWQR 300
AAV.CPP21   TTSTRTWALPTYNNHLYKQISNSTSGGSSNDNAYFGYSTPWGYFDFNRFHCHFSPRDWQR 300

AAV9        LINNNWGFRPKRLNFKLFNIQVKEVTDNNGVKTIANNLTSTVQVFTDSDYQLPYVLGSAH 360
AAV.CPP16   LINNNWGFRPKRLNFKLFNIQVKEVTDNNGVKTIANNLTSTVQVETDSDYQLPYVLGSAH 360
AAV.CPP21   LINNNWGFRPKRLNFKLFNIQVKEVTDNNGVKTIANNLTSTVQVFTDSDYQLPYVLGSAH 360

AAV9        EGCLPPFPADVFMIPQYGYLTLNDGSQAVGRSSFYCLEYFPSQMLRTGNNFQFSYEFENV 420
AAV.CPP16   EGCLPPFPADVFMIPQYGYLTLNDGSQAVGRSSFYCLEYFPSQMLRTGNNFQFSYEFENV 420
AAV.CPP21   EGCLPPFPADVFMIPQYGYLTLNDGSQAVGRSSFYCLEYFPSQMLRTGNNFQFSYEFENV 420

AAV9        PEHSSYAHSQSLDRLMNPLlDQYLYYLSKTTNGSGQNQQTLKESVAGPSNMAVOGRNYTP 480
AAV.CPP16   PFHSSYAHSQSLDRLMNPLIDQYLYYLSKTINGSGQNQQTLKFSVAGPSNMAVQGRNYIP 480
AAV.CPP21   PFHSSYAHSQSLDRLMNPLIDQYLYYLSKTINGSGQNQQTLKFSVAGPSNMAVQGRNYIP 480
```

-continued

```
AAV9        GPSYRQQRVSTTVTQNNNSEFAWPGASSWALNGRNSLMNPGPAMASHKEGEDRFFPLSGS 540
AAV.CPP16   GPSYRQQRVSTTVTQNNNSEFAWPGASSWALNGRNSLMNPGPAMASHKEGEDRFFPLSGS 540
AAV.CPP21   GPSYRQQRVSTTVTQNNNSEFAWPGASSWALNGRNSLMNPGPAMASHKEGEDRFFPLSGS 540

AAV9        LIFGKQGTGRDNVDADKVMITNEEEIKTTNPVATESYGQVATNHQSAQ-------AQAQT 593
AAV.CPP16   LIFGKQGTGRDNVDADKVMITNEEEIKTTNPVATESYGQVATNHQSAQTVSAL-KAQAQT 599
AAV.CPP21   LIFGKQGTGRDNVDADKVMITNEEEIKTTNPVATESYGQVATNHQSAQTVSALFKAQAQT 600

AAV9        GWVQNQGILPGMVWQDRDVYLQGPIWAKIPHTDGNFHPSPLMGGFGMKHPPPQILIKNTP 653
AAV.CPP16   GWVQNQGILPGMVWQDRDVYLQGPIWAKIPHTDGNFHPSPLMGGFGMKHPPPQILIKNTP 659
AAV.CPP21   GWVQNQGILPGMVWQDRDVYLQGPIWAKIPHTDGNFHPSPLMGGFGMKHPPPQILIKNTP 660

AAV9        VPADPPTAFNKDKLNSFITQYSTGQVSVEIEWELQKENSKRWNPEIQYTSNYYKSNNVEE 713
AAV.CPP16   VPADPPTAFNKDKLNSFITQYSTGQVSVEIEWELQKENSKRWNPEIQYTSNYYKSNNVEF 719
AAV.CPP21   VPADPPTAFNKDKLNSFITQYSTGQVSVEIEWELQKENSKRWNPEIQYTSNYYKSNNVEF 720

AAV9        AVNTEGVYSEPRPIGTRYLTRNL 736        (SEQ ID NO: 85)
AAV.CPP16   AVNTEGVYSEPRPIGTRYLTRNL 742        (SEQ ID NO: 89)
AAV.CPP21   AVNTEGVYSEPRPIGTRYLTRNL 743        (SEQ ID NO: 90)
```

2. Recombinant AAV Production

Recombinant AAVs were packaged using standard three-plasmid co-transfection protocol (pRC plasmid, pHelper plasmid and pAAV plasmid). pRC9 (or its variant), pHelper and pAAV carrying a transgene (e.g. nucleus-directed RFP H2B-mCherry driven by an ubiquitous EF1a promoter) were co-transfected into HEK 293T cells using polyethylenimine (PEI, Polysciences). rAAVs vectors were collected from serum-free medium 72 h and 120 h post transfection and from cell at 120 h post transfection. AAV particles in the medium were concentrated using a PEG-precipitation method with 8% PEG-8000 (wt/vol). Cell pellets containing viral particles were resuspended and lysed through sonication. Combined viral vectors from PEG-precipitation and cell lysates were treated with DNase and RNase at 37° C. for 30 mins and then purified by iodixanol gradient (15%, 25%, 40% and 60%) with ultracentrifugation (VTi 50 rotor, 40,000 r.p.m, 18° C., 1 h). rAAVs were then concentrated using Millipore Amicon filter unit (UFC910008, 100K MWCO) and formulated in Dulbecco's phosphate buffered saline (PBS) containing 0.001% Pluronic F68 (Gibco).

3. AAV Titering

Virus titer was determined by measuring DNase-resistant genome copies using quantitative PCR. pAAV-CAG-GFP was digested with PVUII(NEB) to generate free ends for the plasmid ITRs, and was used for generating a standard curve. Virus samples were incubated with DNase I to eliminate contaminating DNA, followed by sodium hydroxide treatment to dissolve the viral capsid and to release the viral genome. Quantitative PCR was performed using an ITR Forward primer 5'-GGAACCCCTAGTGATGGAGTT (SEQ ID NO:91) and an ITR Reverse primer 5'-CGGCCTCAGTGAGCGA (SEQ ID NO:92). Vector titers were normalized to the rAAV-2 reference standard materials (RSMs, ATCC, cat No:VR-1616, Manassas, VA).

4. Administration of AAV in Mice

For intravenous administration, AAV diluted in sterile saline (0.2 ml) was administered through tail vein injection in adult mice (over 6 weeks of age). Animals then survived for three weeks before being euthanized for tissue harvesting. For intracerebral injection, AAV diluted in PBS (10 ul) was injected using a Hamilton syringe with coordinates from bregma: 1.0 mm right, 0.3 backward, 2.6 mm deep. All animal studies were performed in an AAALAC-accredited facility with IACUC approval.

5. Mouse Tissue Processing

Anesthetized animals were transcardially perfused with cold phosphate buffered saline (PBS) followed by 4% paraformaldehyde (PFA). Tissues were post-fixed in 4% PFA overnight, and then immersed in 30% sucrose solutions for two days prior to embedding and snap-freezing in OCT. Typically, 80 um thick brain sections were cut for imaging of native fluorescence, 40 um thick brain sections for IHC.

6. In Vitro Human BBB Spheroid Model

Hot 1% agarose (w/v, 50 ul) was added in a 96-well plate to cool/solidify. Primary human astrocytes (Lonza Bioscience), human brain microvascular pericytes (HBVP, ScienCell Research Laboratories) and human cerebral microvascular endothelial cells (hCMEC/D3; Cedarlane) were then seeded onto the agarose gel in a 1:1:1 ratio (1500 cells of each type). Cells were cultured at 37° C. in a 5% CO2 incubator for 48-72 hours to allow for spontaneous assembly of multicellular BBB spheroids. A multicellular barrier was reported to form at the periphery of the spheroid, mimicking the BBB. AAVs-H2B-mCherry were added to the culture medium, and 4 days later all spheroids were fixed using 4% PFA, transferred into a Nunc Lab-Tek II thin-glass 8-well chambered coverglass (Thermo Scientific), and imaged using a Zeiss LSM710 confocal microscope. The intensity of RFP signal inside the spheroids was examined and used as a "read-out".

7. AAV Administration in Non-Human Primate (NHP)

All NHP studies were performed by a CRO in an AAALAC-accredited facility with IACUC approval. Cynomolgus monkeys were pre-screened for little or no pre-existing neutralizing antibody against AAV9 (titer of <1:5). AAV diluted in PBS/0.001% F68 was injected intravenously (via cephalic vein or femoral vein) using a peristaltic pump. 3 weeks later, animals were subject to transcardial perfusion with PBS, followed by 4% PFA. Tissues were then collected and processed for paraffin embedding and sectioning.

8. Immunohistochemistry

Floating staining was performed for mouse tissue sections with primary antibodies diluted in PBS containing 10% donkey serum and 2% Triton X-100. Primary antibodies used include: chicken anti-GFP (1:1000); rabbit anti-RFP (1:1000); mouse anti-NeuN (1:500); rat anti-GFAP (1:500); Goat anti-GFAP (1:500); mouse anti-CD31(1:500). Secondary antibodies conjugated to fluorophores of Alexa Fluor 488, Alexa Fluor 555 or Alexa Fluor 647 were applied against the primary antibody's host species at a dilution of 1:200.

For paraffin sections of NHP tissue, DAB staining was performed to visualize cells transduced by AAV-AADC. Rabbit anti-AADC antibody (1:500, Millipore) was used as primary antibody.

9. AAV Binding Assay

HEK293T cells were cultured at 37° C. in a 5% CO2 incubator. One day after seeding of HEK293T cells in a 24-well plate at a density of 250,000 cells per well, a cDNA plasmid of LY6A was transiently transfected into the cells using a transfection mixture of 200 ul DMEM (31053028; Gibco), 1 ug DNA plasmid and 3 ug of PEI. 48 hours post transfection, cells were placed on ice to chill down for 10 mins. The medium was then changed with 500 ul ice-cold serum-free DMEM medium containing rAAVs-mCherry at MOI of 10000. After incubating on ice for one hour, cells with presumably AAVs bound to their surface were washed with cold PBS for three times and were then subject to genomic DNA isolation. Cell-binding viral particles were quantified by using qPCR with primers specific to mCherry and normalized to HEK293T genomes using human GCG as reference.

10. Mouse Model of Glioblastoma

All experiments were performed in compliance with protocols approved by the Animal Care and Use Committees (IACUC) at the Brigham and Women's Hospital and Harvard Medical School. Syngeneic immuno-competent C57BL/6 female mice weighing 20+/−1 g (Envigo) were used. GL261-Luc (100,000 mouse glioblastoma cells) resuspended in 2 μL phosphate buffered saline (PBS) was injected intracranially using 10 μl syringe with a 26-gauge needle (80075; Hamilton). A stereotactic frame was used to locate the implantation site (coordinates from bregma in mm: 2 right, 0.5 forward, at a depth of 3.5 into cortex). 7 days later, 200 ul AAV-HSV-TK1 (1E+12 viral genomes, IV) was administered once and ganciclovir (50 mg/kg) was administered daily for 10 days.

Example 1. Modification of AAV9 Capsid

Figure 1A:
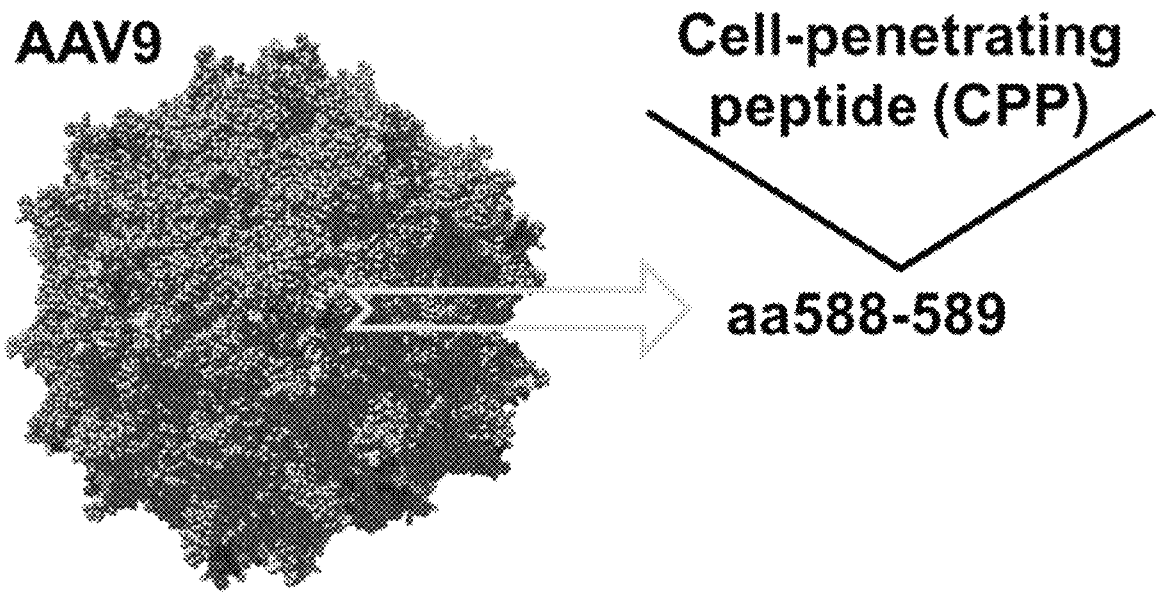
FIGS. 1A-1B depict an exemplary strategy of engineering AAV9 by inserting cell-penetrating peptides (CPPs) into its capsid.
Figure 1B:
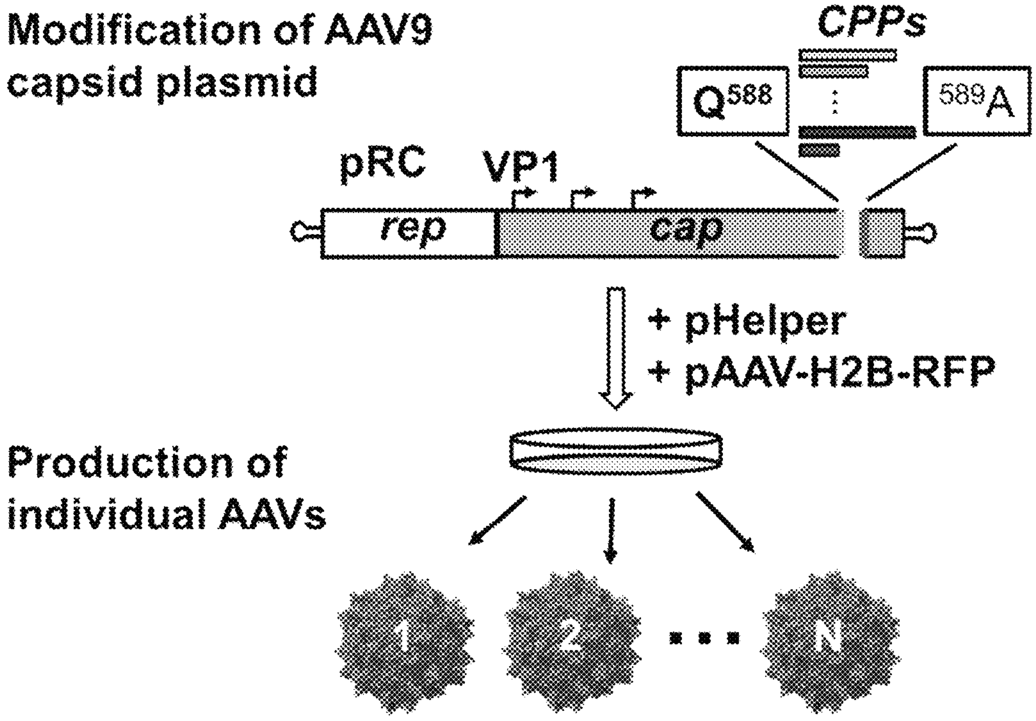

To identify peptide sequences that would enhance permeation of a biomolecule or virus across the blood brain barrier an AAV peptide display technique was used. Individual cell-penetrating peptides, as listed in Table 3, were inserted into the AAV9 capsid between amino acids 588 and 589 (VP1 numbering) as illustrated in FIG. 1A. The insertion was carried out by modifying the RC plasmid, one of the three plasmids co-transfected for AAV packaging; FIG. 1B shows an exemplary schematic of the experiments. Individual AAV variants were produced and screened separately. See Materials and Methods #1-3 for more details.

TABLE 3

| | AAV | Name of CPP insert | Amino acid sequence of CPP | # | No. of CPP residues | Viral titer |
|---|---|---|---|---|---|---|
| Initial screening | AAV9 | N/A | N/A | | N/A | Normal |
| | AAV.CPP.1 | SynB1 | RGGRLSYSRRRFSTSTGR | 93 | 18 | Low |
| | AAV.CPP.2 | L-2 | HARIKPTFRRLKWKYKGKFW | 94 | 20 | Low |
| | AAV.CPP.3 | PreS2-TLM | PLSSIFSRIGDP | 95 | 12 | Low |
| | AAV.CPP.4 | Transportan 10 | AGYLLGKINLKALAALAKKIL | 96 | 21 | Low |
| | AAV.CPP.5 | SAP | VRLPPPVRLPPPVRLPPP | 97 | 18 | Normal |
| | AAV.CPP.6 | SAP(E) | VELPPPVELPPPVELPPP | 98 | 18 | Normal |
| | AAV.CPP.7 | SVM3 | KGTYKKKLMRIPLKGT | 99 | 16 | Low |
| | AAV.CPP.8 | (PPR)3 | PPRPPRPPR | 100 | 9 | Normal |
| | AAV.CPP.9 | (PPR)5 | PPRPPRPPRPPRPPR | 101 | 15 | Low |
| | AAV.CPP.10 | Polyarginine | RRRRRRRR | 102 | 8 | Low |
| | AAV.CPP.11 | Bip1 | VPALR | 1 | 5 | Normal |
| | AAV.CPP.12 | Bip2 | VSALK | 2 | 5 | Normal |
| | AAV.CPP.13 | DPV15 | LRRERQSRLRRERQSR | 103 | 16 | NA |
| | AAV.CPP.14 | HIV-1 Tat | RKKRRQRRR | 104 | 9 | NA |
| Follow-up screening | AAV.CPP.15 | Bip1.1 | TVPALR (Rat) | 3 | 6 | Normal |
| | AAV.CPP.16 | Bip2.1 | TVSALK (Syn) | 4 | 6 | Normal |
| | AAV.CPP.17 | Bip2.2 | FTVSALK (Syn) | 5 | 7 | Normal |
| | AAV.CPP.18 | Bip2.3 | LTVSALK (Syn) | 6 | 7 | Normal |
| | AAV.CPP.19 | Bip2.4 | KFTVSALK (Syn) | 72 | 8 | Normal |
| | AAV.CPP.20 | Bip2.5 | TFVSALK (Syn) | 7 | 7 | Normal |
| | AAV.CPP.21 | Bip2.6 | TVSALFK (Syn) | 8 | 7 | Normal |
| | AAV.CPP.22 | Bip2.6Rat | TVPALFR (Rat) | 9 | 7 | Normal |

#, SEQ ID NO:
Syn, synthetic

Example 2. First Round of In Vivo Screening

Figure 2A:
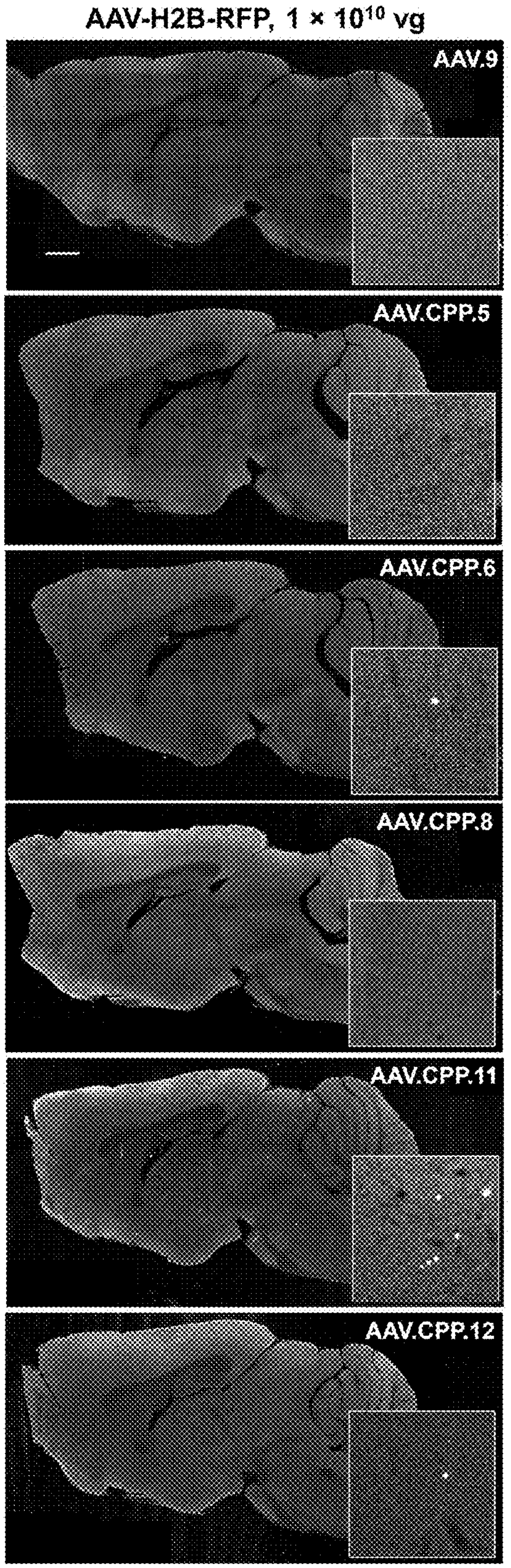
FIGS. 2A-2B depict representative images of mouse brain sections and their quantitative analysis after intravenous administration of low-dose candidate AAVs. Mice with mixed genetic background are used. Candidate AAVs differs in their inserted CPPs (see Table 3), but all express nuclear red fluorescent protein (RFP) as reporter. Candidate AAVs with low production yields are excluded for further screening. The dose of AAV is $1\times10^{10}$ vg (viral genome) per animal. Each white dot in FIG. 2A represents a RFP-labeled cell.
Figure 2B:
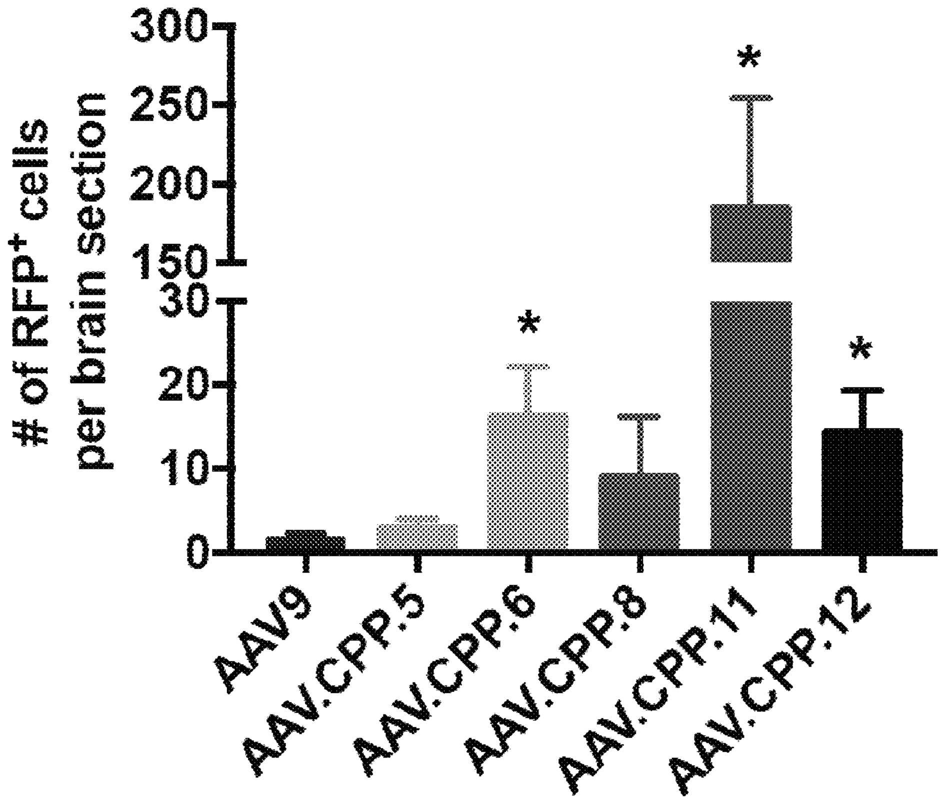
Figure 2C:
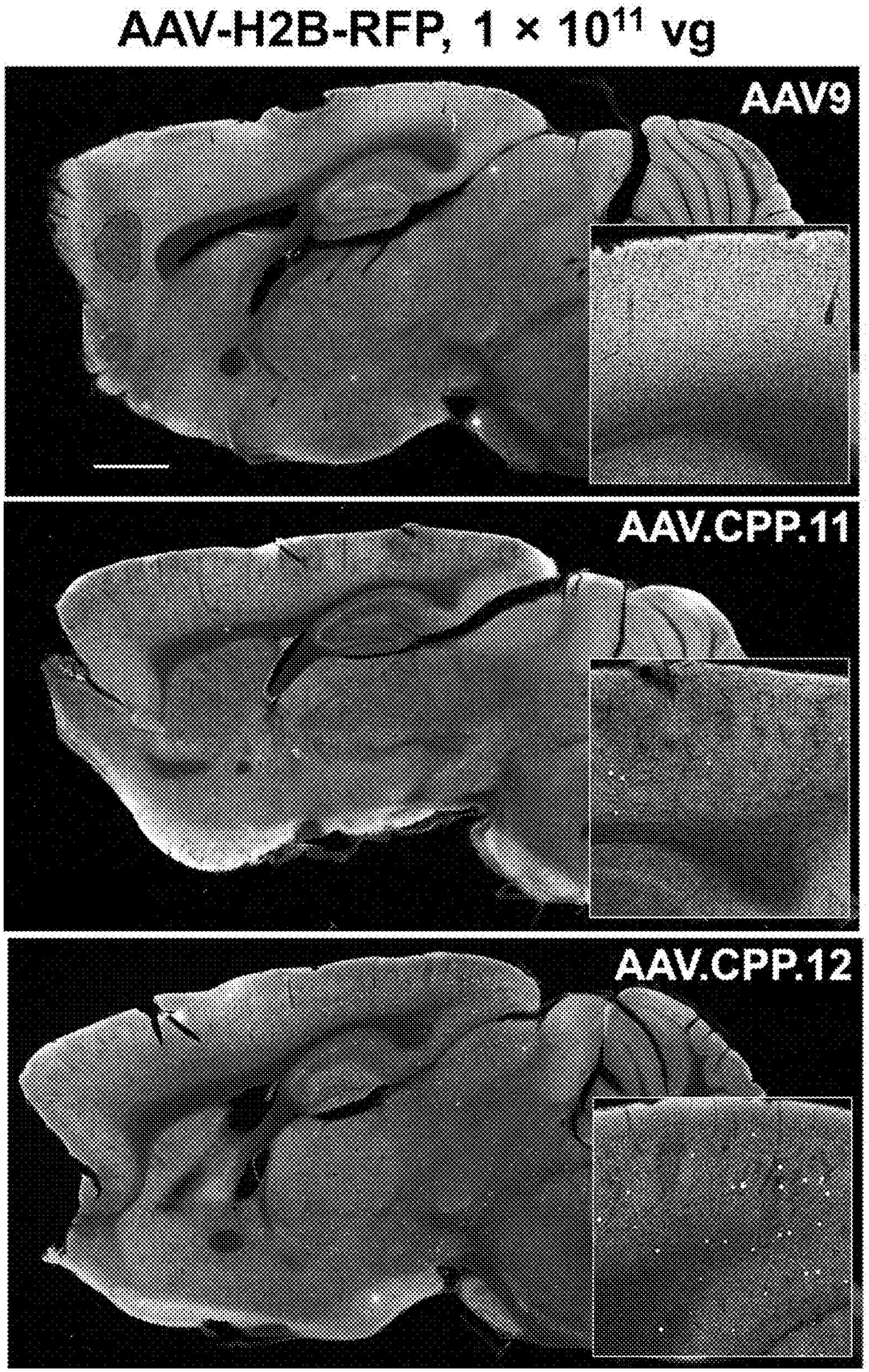
FIGS. 2C-2D depict representative images of mouse brain sections and their quantitative analysis after intravenous administration of AAV.CPP.11 and AAV.CPP.12 in a repeat experiment. AAV.CPP.11 and AAV.CPP.12 contain CPPs BIP1 and BIP2 respectively (see Table 3). The doses of the AAVs are increased to $1\times10^{11}$ vg per animal. Candidate AAVs express nuclear red fluorescent protein (RFP) as reporter. Each white dot in FIG. 2C represents a RFP-labeled cell.
Figure 2D:
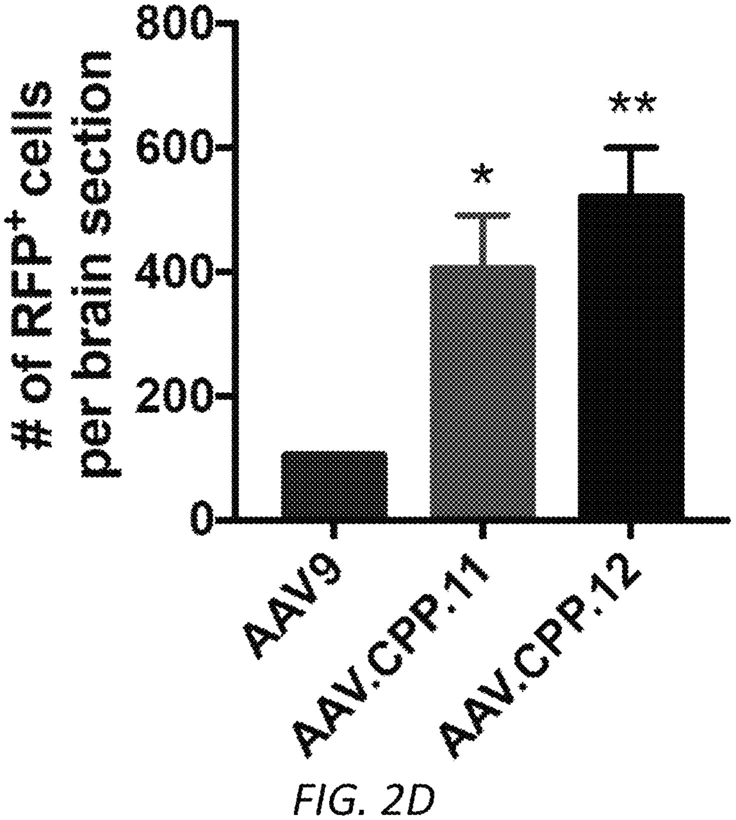

AAVs expressing nuclear RFP (H2B-RFP) were injected intravenously in adult mice with mixed C57BL/6 and BALB/c genetic background. 3 weeks later, brain tissues were harvested and sectioned to reveal RFP-labelled cells (white dots in FIGS. 2A and 2C, quantified in FIGS. 2B and 2D, respectively). CPPs BIP1 and BIP2 were inserted into the capsids of AAV.CPP.11 and AAV.CPP.12, respectively. See Materials and Methods #4-5 for more details.

Example 3. Optimization of Modified AAV9 Capsids

Figure 3A:
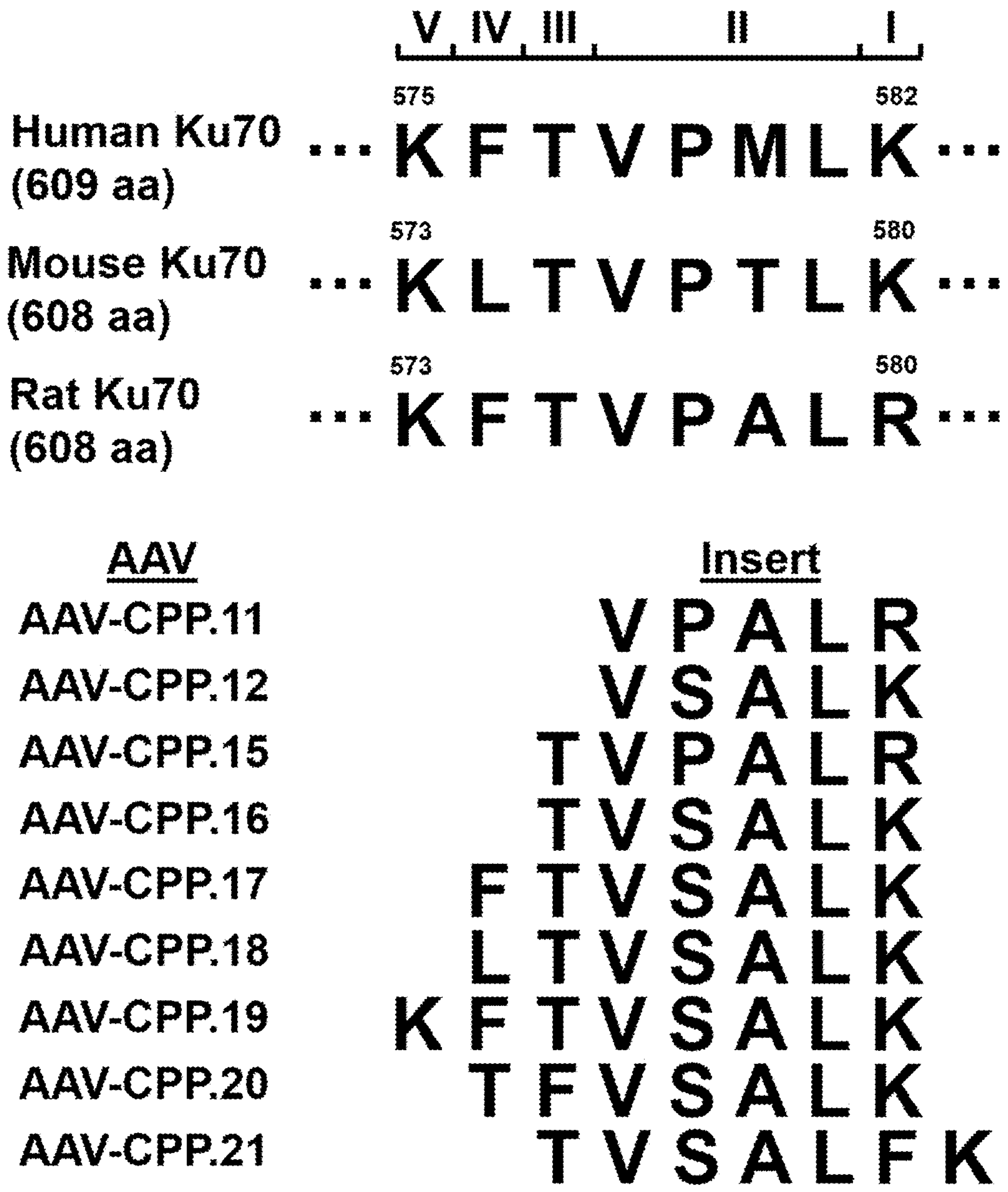
FIG. 3A depicts the optimization of the BIP targeting sequence in order to further engineer AAV9 towards better brain transduction. BIP1 (VPALR, SEQ ID NO:1), which enables AAV9 to transduce brain more efficiently (as in AAV.CPP.11), is derived from the protein Ku70 in rats. Human, mouse and rat Ku70 proteins differ in their exact amino acid sequences. BIP2 (VSALK, SEQ ID NO:2) as in AAV.CPP.12 is a "synthetic" peptide related to BIP1. Further engineering focuses on the VSALK sequence in the hope of minimizing species specificity of final engineered AAV. To generate new targeting sequence, amino acids of interest are added to the VSALK sequence, and in other cases positions of individual amino acids are switched. All new BIP2-derived sequences are again inserted into the AAV9 capsid to generate new candidate AAVs for screening. Sequences appearing in order are SEQ ID NOs: 69, 70, 71, 1-6, 72, 7, and 8.
Figure 3B:
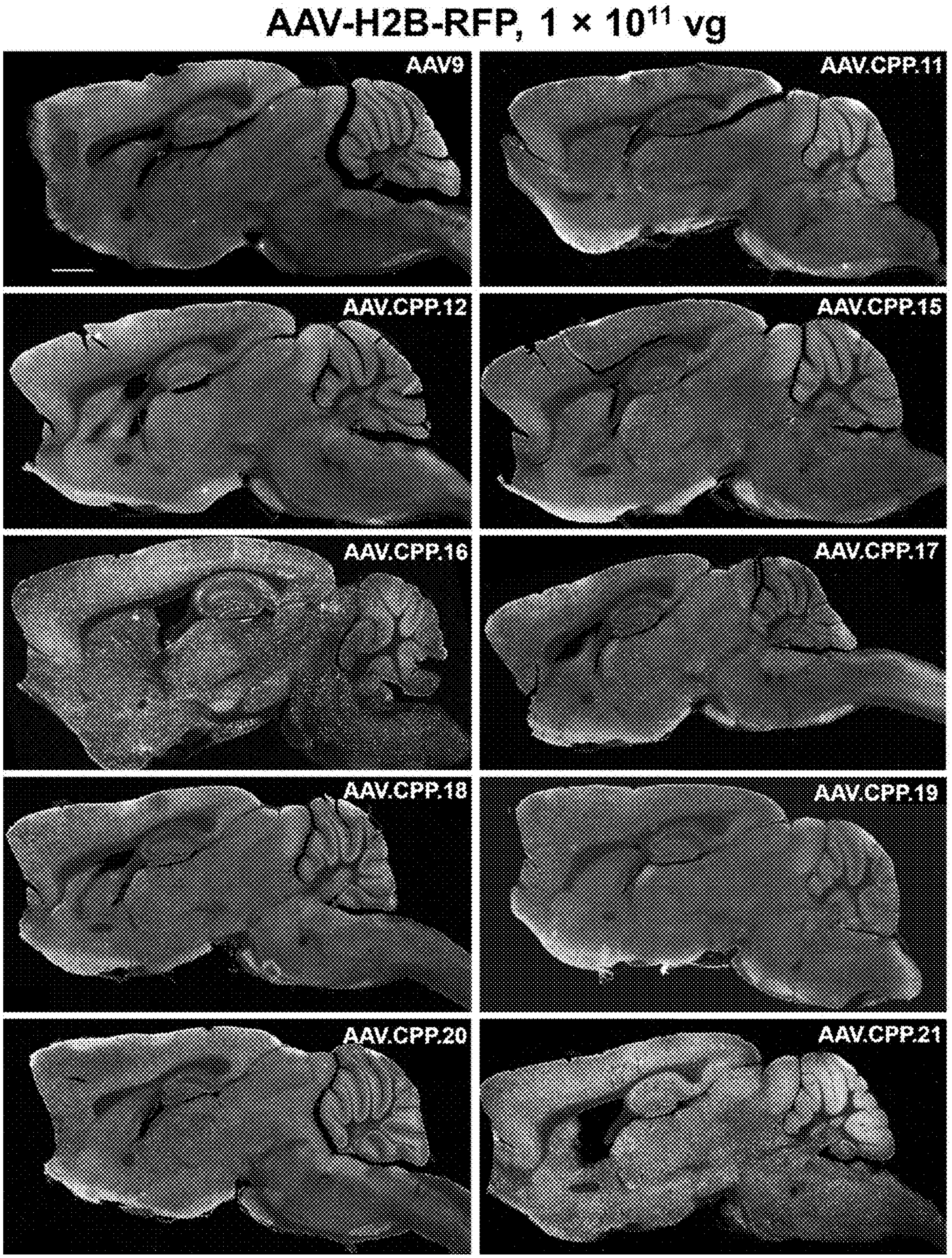
FIGS. 3B-3C depict representative images of mouse brain sections and their quantitative analysis after intravenous administration of more candidate AAVs. All candidate AAVs express nuclear red fluorescent protein (RFP) as reporter. The dose of AAV is $1\times10^{11}$ vg per animal. Each white dot in FIG. 3B represents a RFP-labeled cell. AAV.CPP.16 and AAV.CPP.21 were identified as top hits with their robust and widespread brain transduction.
Figure 3C:
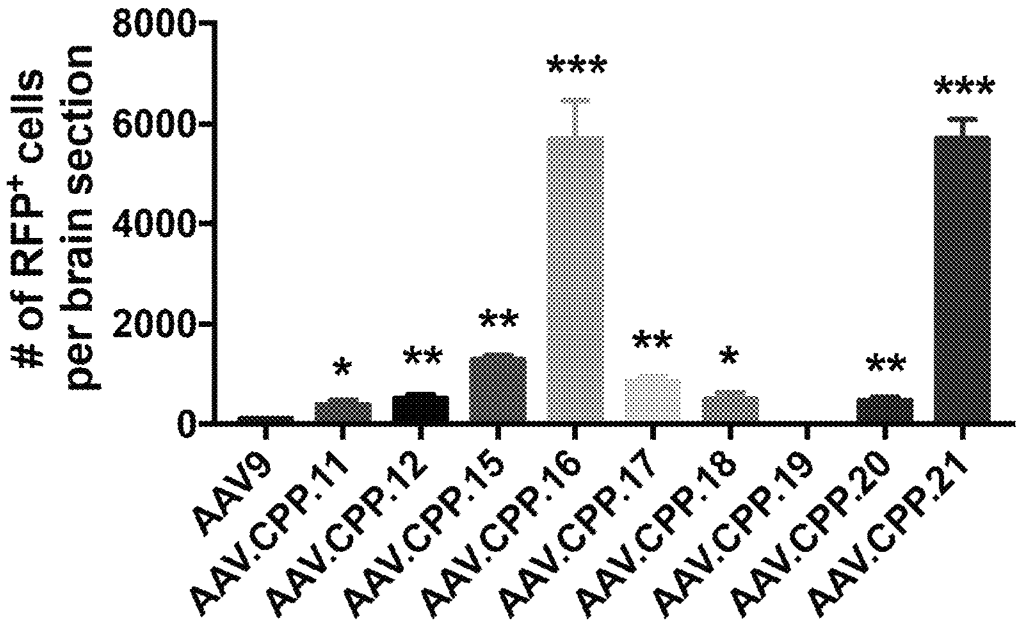

AAV.CPP.11 and AAV.CPP.12 were further engineered by optimizing the BIP targeting sequences. BIP inserts were derived from the protein Ku70 (See FIG. 3A and Material/Methods #1 for full sequence). The BIP sequence VSALK, which is of "synthetic" origin, was chosen as a study focus to minimize potential species specificity of engineered AAV vectors. AAVs were produced and tested separately for brain transduction efficiency as compared with AAV9 (see FIGS.

Figure 3D:
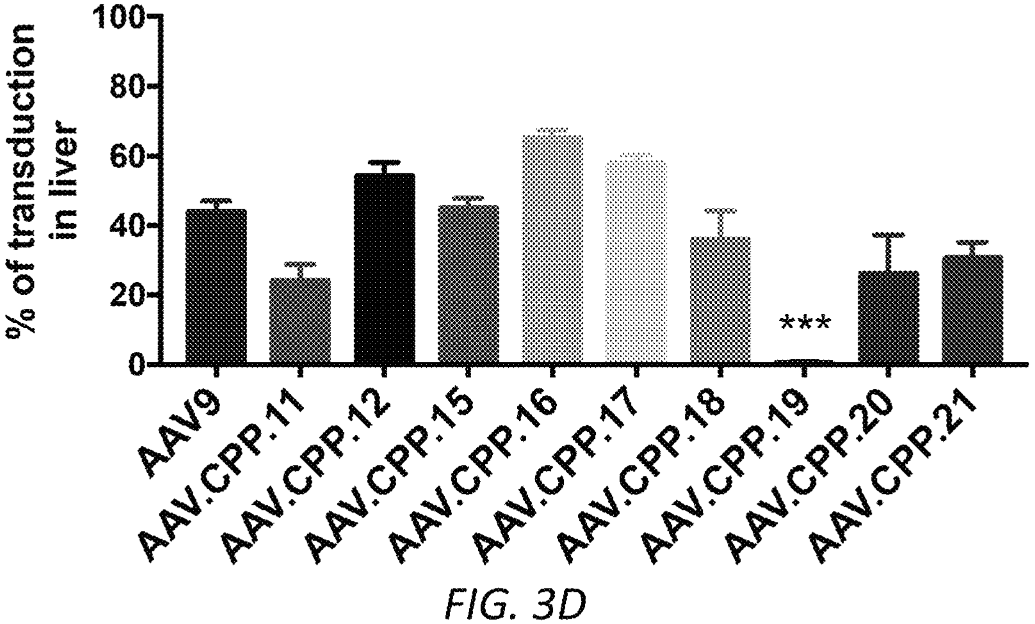
FIG. 3D depicts quantitative analysis of transduction efficiency in the liver after intravenous administration of candidate AAVs. Percentage of transduced liver cells is presented. The dose of AAV is $1\times10^{11}$ vg per animal. ***P<0.001, vs. AAV9, ANOVA.

3B-C). Percentages of cell transduction in the mouse liver 3 weeks after IV injection of some AAV variants delivering the reporter gene RFP are shown in FIG. 3D. See Materials and Methods #1-5 for more details.

Example 4. In Vitro Model—BBB Permeation Screening

Figure 4A:
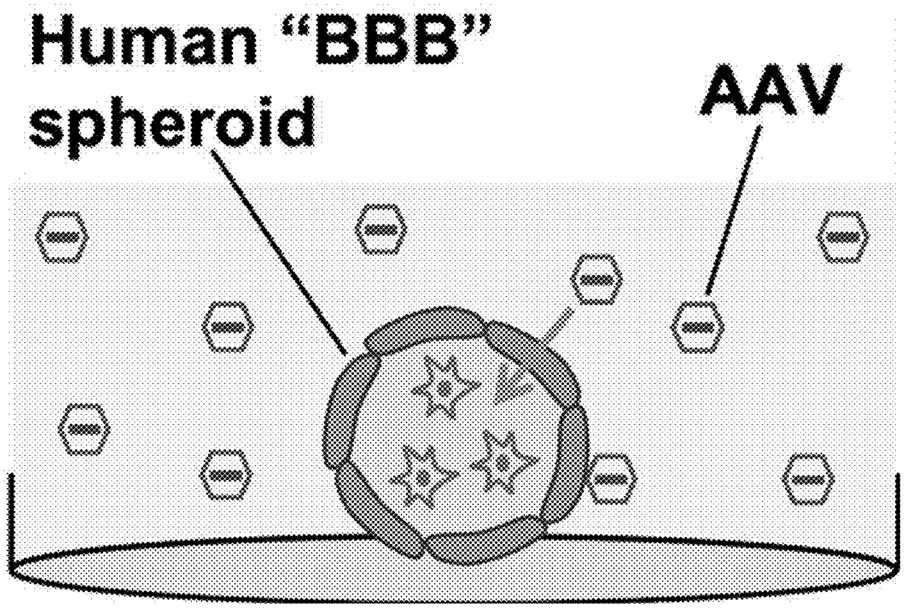
FIGS. 4A-4E depict screening of selected candidate AAVs in an in vitro spheroid model of human blood-brain barrier.
Figure 4B:
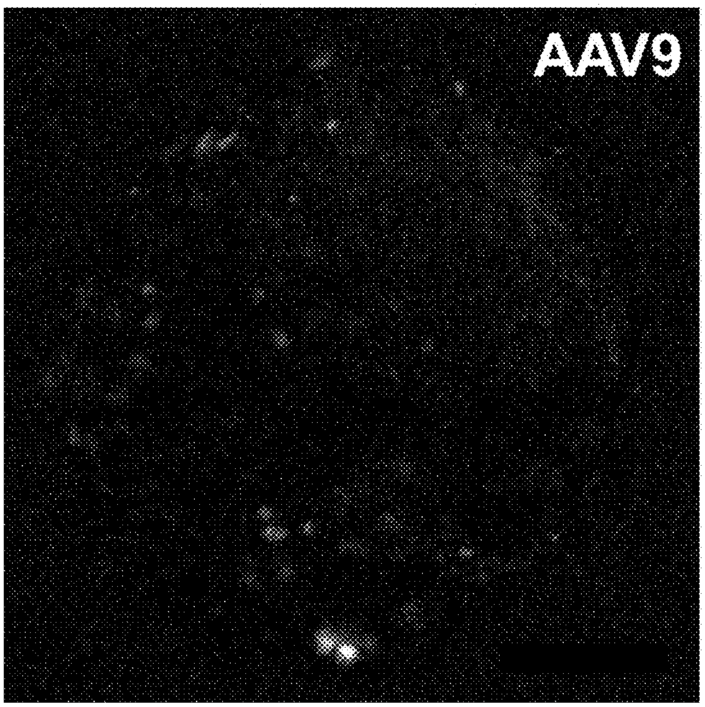
Figure 4C:
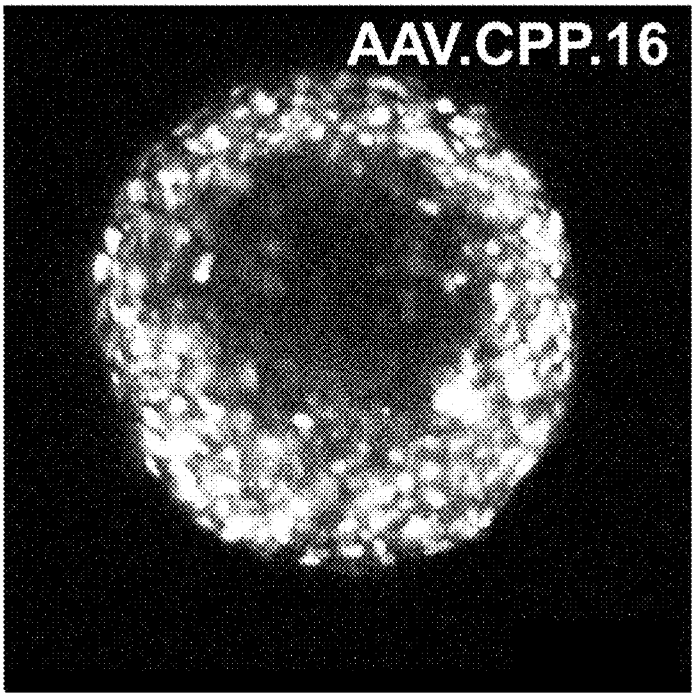
Figure 4D:
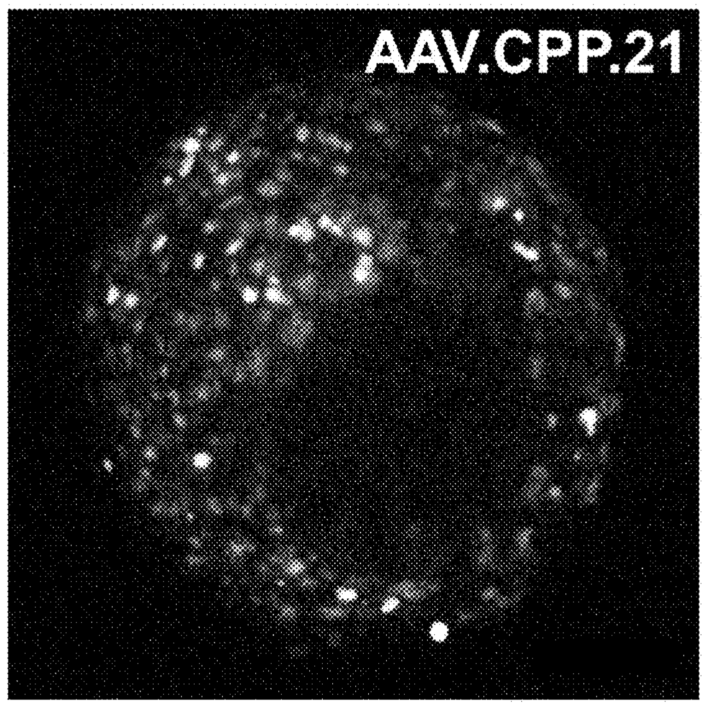
Figure 4E:
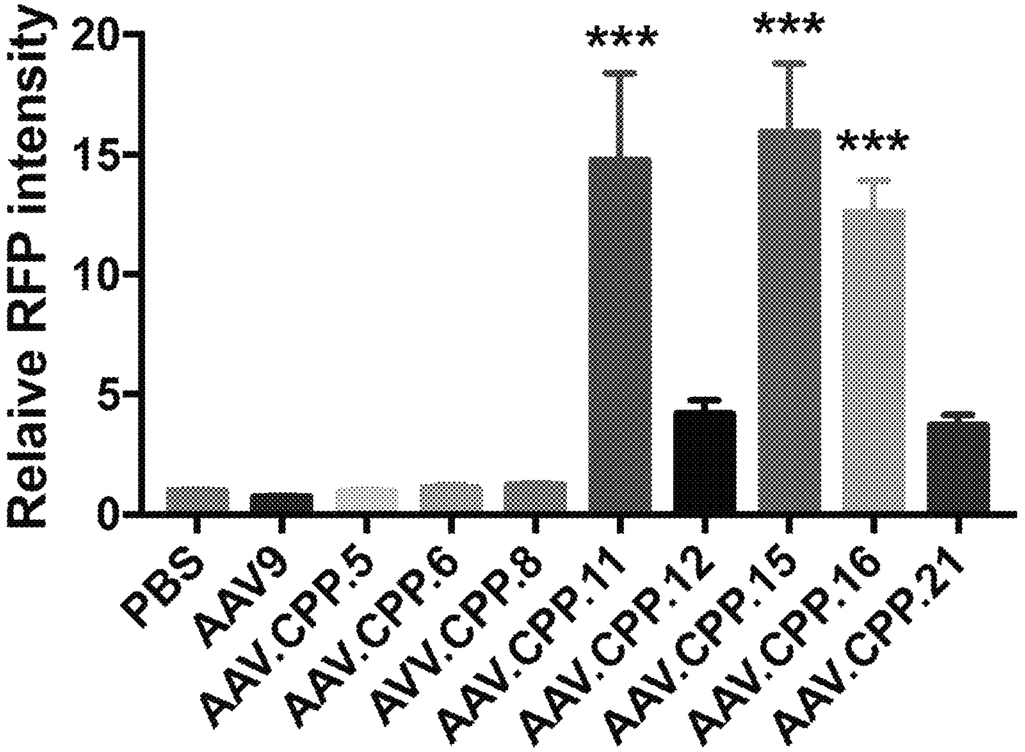

Some of the AAV variants were screened for the ability to cross the human BBB using an in vitro spheroid BBB model. The spheroid contains human microvascular endothelial cells, which form a barrier at the surface, and human pericytes and astrocytes. AAVs carrying nuclear RFP as reporter were assessed for their ability to penetrate from the surrounding medium into the inside of the spheroid and to transduce the cells inside. FIG. 4A shows an experimental schematic. FIGS. 4B-D show results for wt AAV9, AAV.CPP.16, and AAV.CPP.21, respectively, those and other peptides are quantified in FIG. 4E. In this model, peptides 11, 15, 16, and 21 produced the greatest permeation into the spheroids. See Materials and Methods #6 for more details.

Example 5. In Vivo BBB Permeation Screening

Figure 5A:
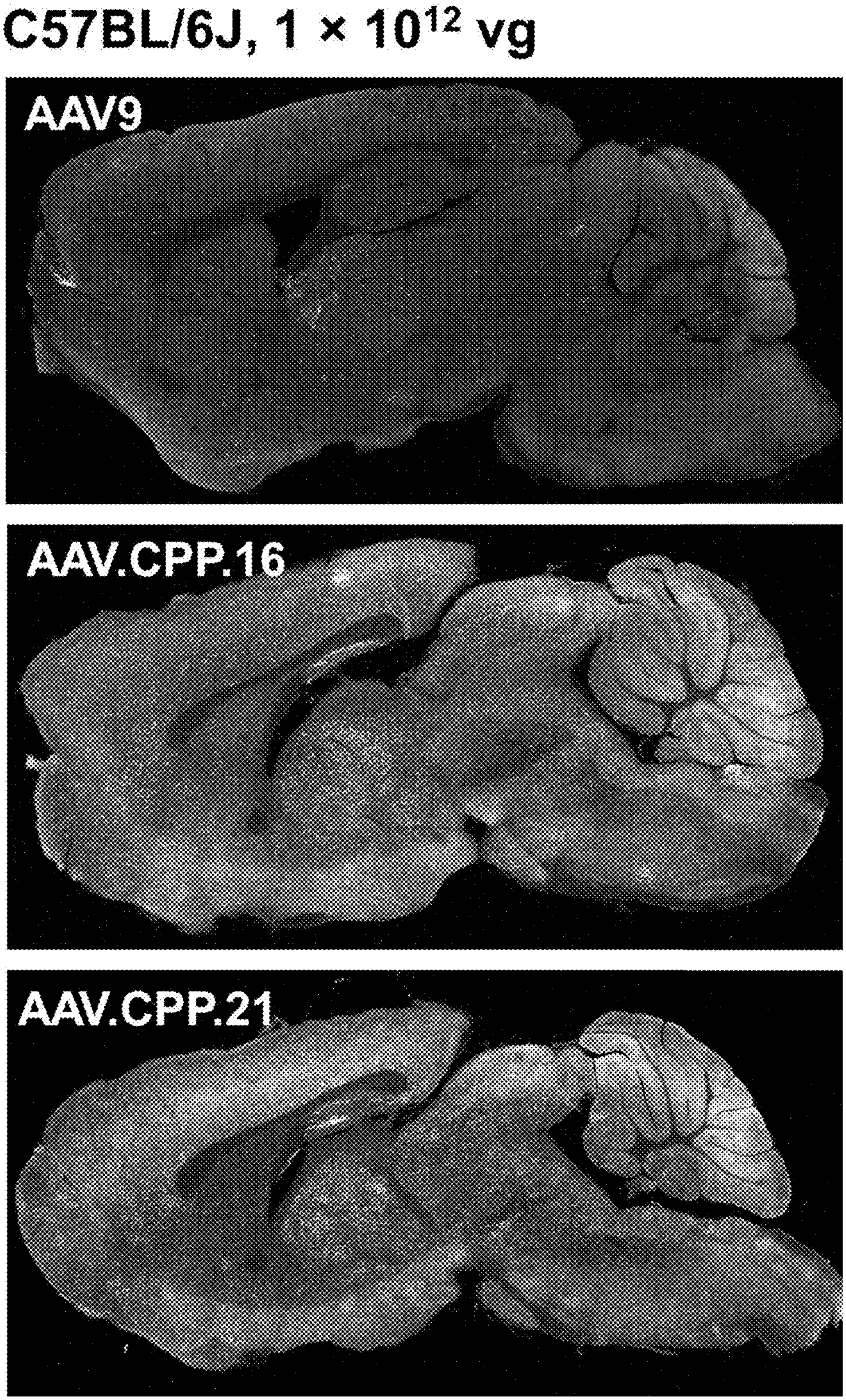
FIGS. 5A-5B depict representative images of brain sections and their quantitative analysis after intravenous administration of AAV9, AAV.CPP.16 and AAV.CPP.21 in C57BL/6J inbred mice. All candidate AAVs express nuclear red fluorescent protein (RFP) as reporter. The dose of AAV is $1\times10^{12}$ vg per animal. Each white dot in FIG. 5A represents a RFP-labeled cell.
Figure 5B:
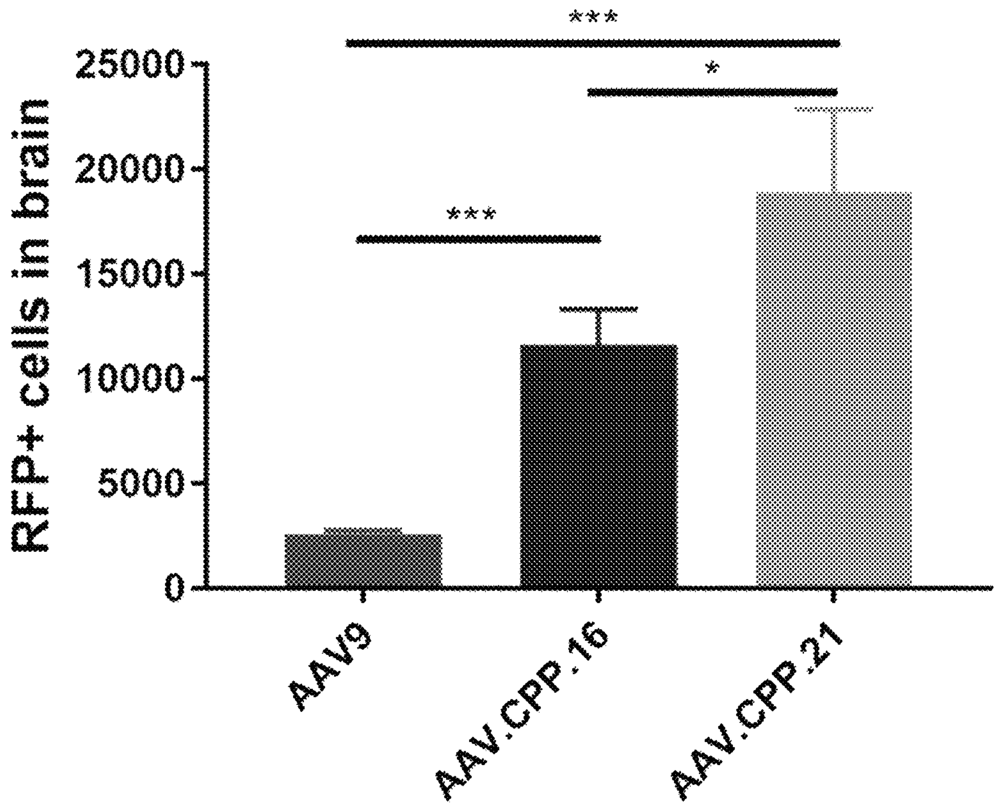
Figure 6A:
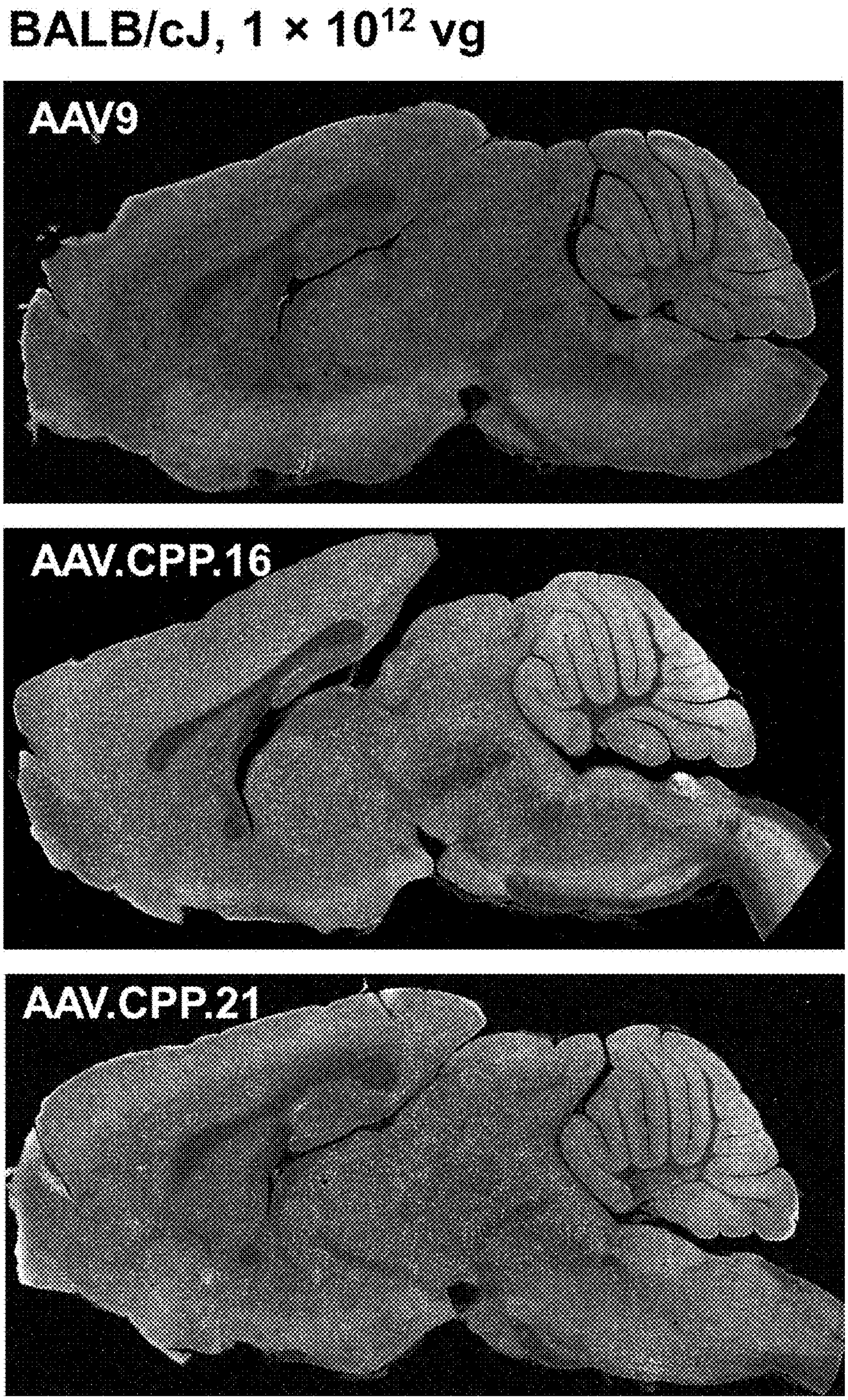
FIGS. 6A-6B depict representative images of brain sections and their quantitative analysis after intravenous administration of AAV9, AAV.CPP.16 and AAV.CPP.21 in BALB/cJ inbred mice. All candidate AAVs express nuclear red fluorescent protein (RFP) as reporter. The dose of AAV is $1\times10^{12}$ vg per animal. Each white dot in FIG. 6A represents a RFP-labeled cell.
Figure 6B:
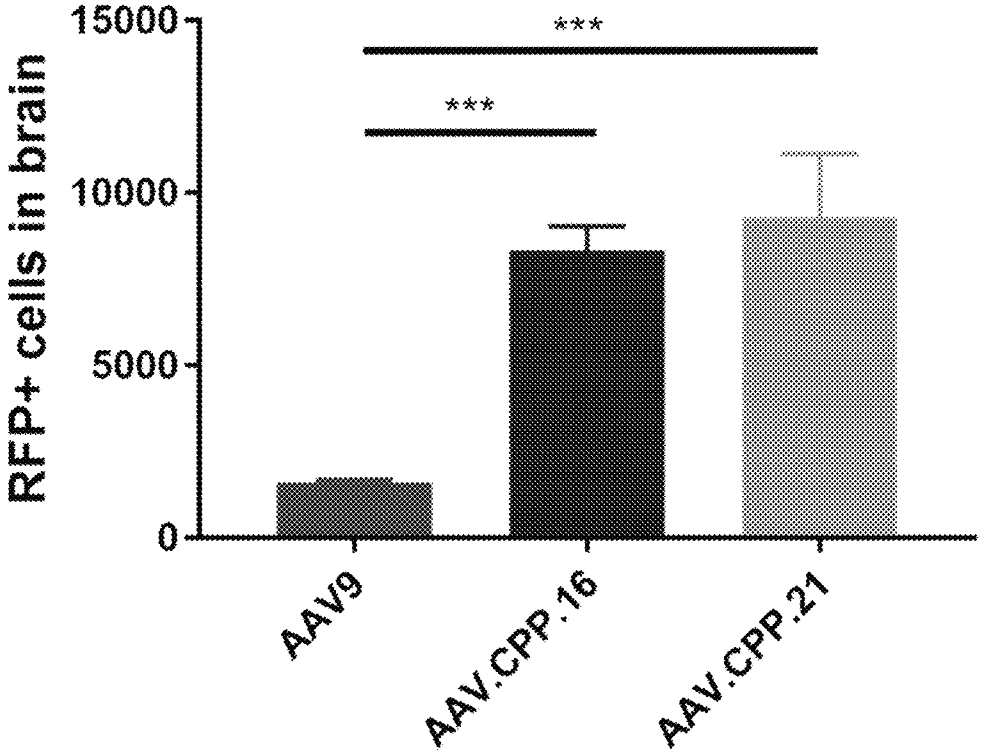

AAV.CPP.16 and AAV.CPP.21 were selected for further evaluation in an in vivo model, in experiments performed as described above for Example 2. All AAVs carried nuclear RFP as reporter. Both showed enhanced ability vs. AAV9 to transduce brain cells after intravenous administration in C57BL/6J adult mice (white dots in brain sections in FIG. 5A, quantified in FIG. 5B) and in BALB/c adult mice (white dots in brain sections in FIG. 6A, quantified in FIG. 6B).

Figure 7A:
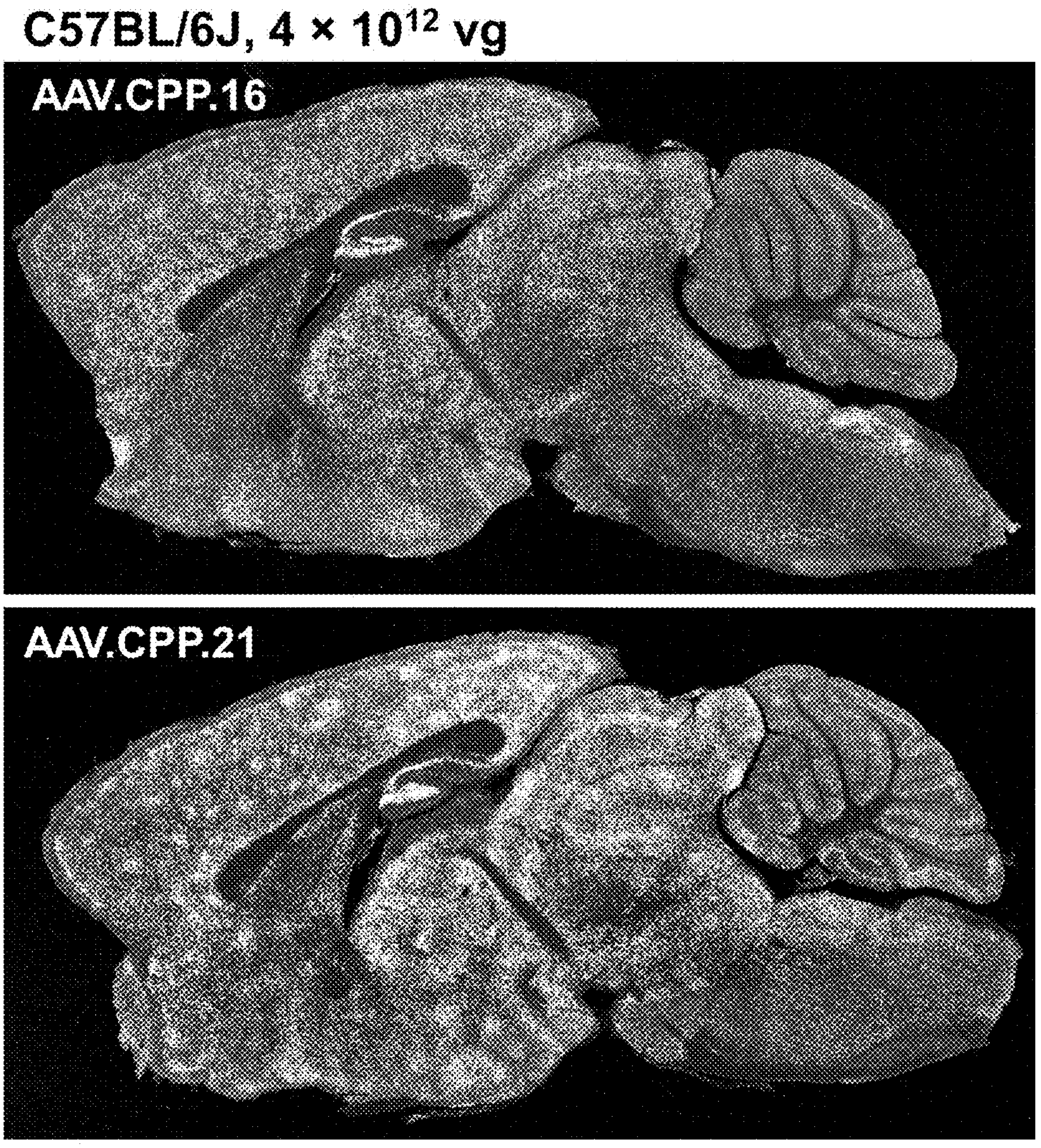
FIGS. 7A-7B depict representative images of brain sections and their quantitative analysis after intravenous administration of high-dose AAV.CPP.16 and AAV.CPP.21 in C57BL/6J inbred mice. Both candidate AAVs express nuclear red fluorescent protein (RFP) as reporter. The dose of AAV is $4\times10^{12}$ vg per animal. Each white dot in FIG. 7A represents a RFP-labeled cell.
Figure 7B:
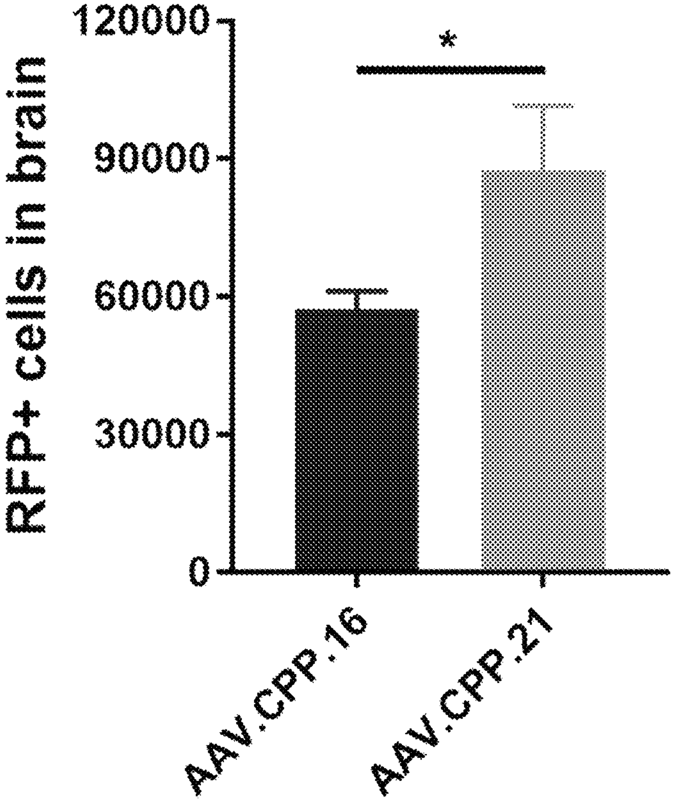

High doses of AAV.CPP.16 and AAV.CPP.21 ($4\times10^{12}$ vg per mouse, administered IV) resulted in widespread brain transduction in mice. Both AAVs carried nuclear RFP as reporter (white dots in brain sections in FIG. 7A, quantified in FIG. 7B).

Example 6. In Vivo Distribution of Modified AAVs

Figure 8A:
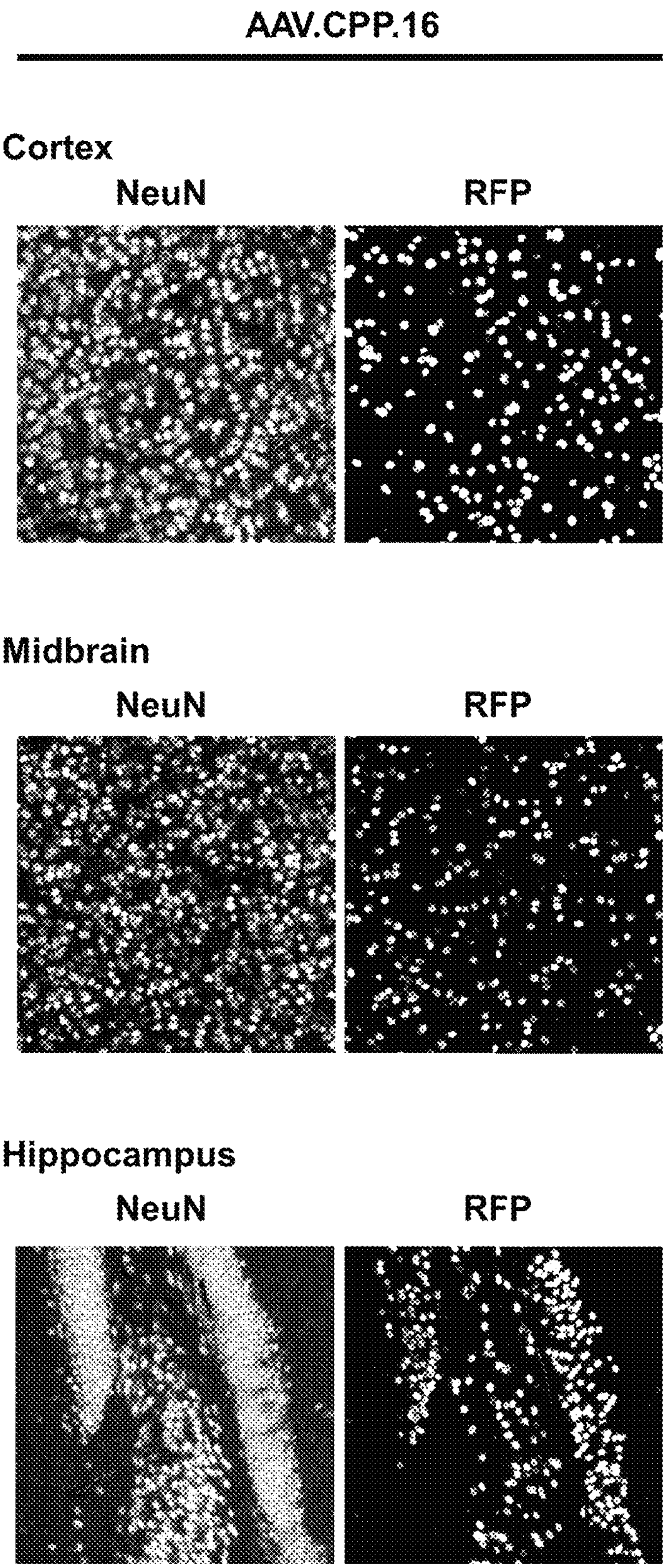
FIG. 8A shows AAV.CPP.16 and AAV.CPP.21 transduce adult neurons (labeled by a NeuN antibody) across multiple brain regions in mice including the cortex, midbrain and hippocampus. Transduced neurons are co-labeled by NeuN antibody and RFP. AAVs of $4\times10^{12}$ vg were administered intravenously in adult C57BL/6J mice (6 weeks old).

As shown in FIG. 8A, AAV.CPP.16 and AAV.CPP.21 preferentially targeted neurons (labeled by a NeuN antibody) across multiple brain regions in mice including the cortex, midbrain and hippocampus. Both AAVs carried nuclear RFP as a reporter.

Figure 8B:
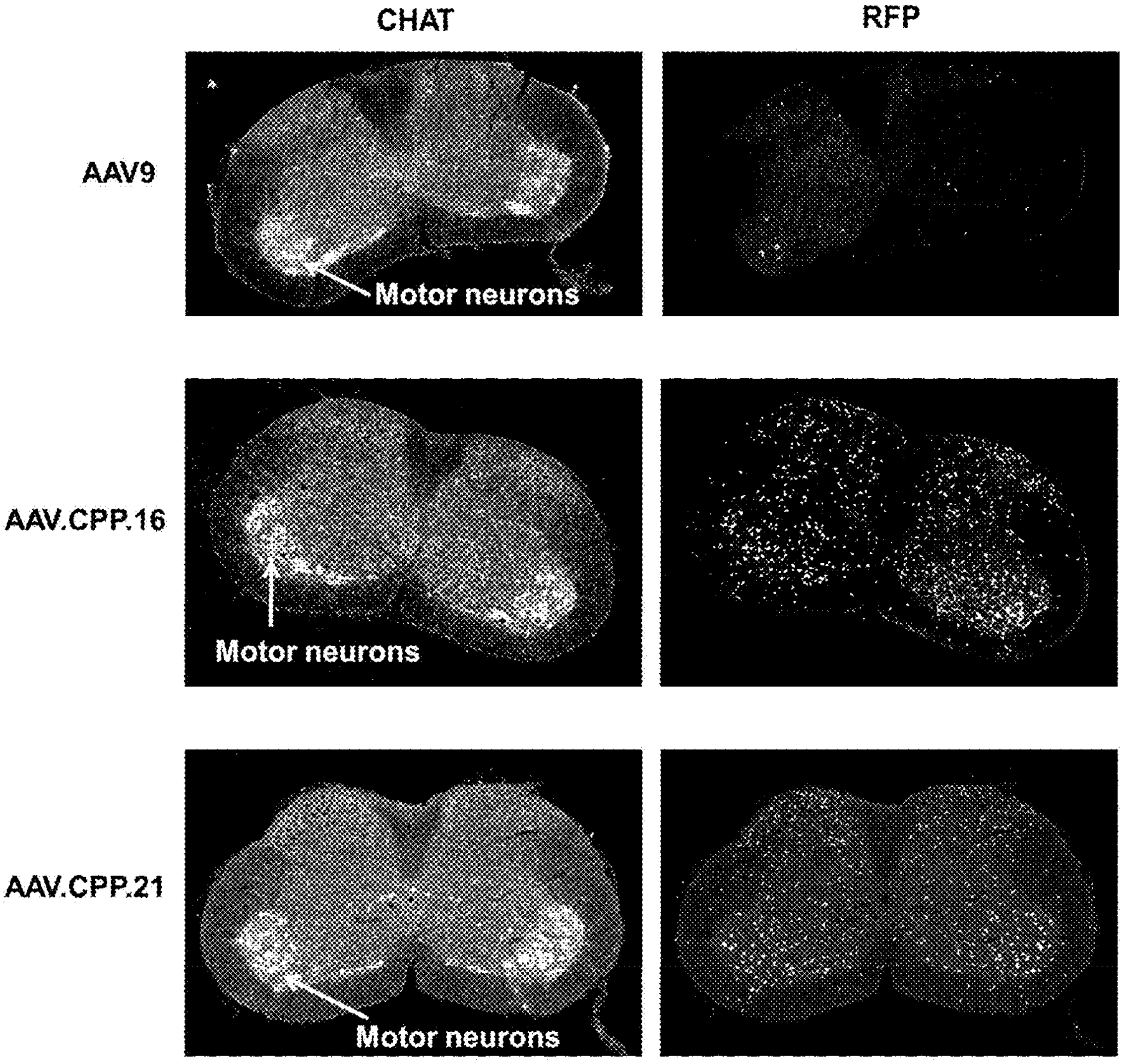
FIG. 8B depicts that AAV.CPP.16 and AAV.CPP.21 show enhanced ability vs. AAV9 in targeting the spinal cord and motor neurons in mice. AAVs of $4\times10^{10}$ vg were administered intravenously into neonate mice (1 day after birth). Motor neurons in the ventral horn of the spinal cord were visualized using CHAT antibody staining. Co-localization of RFP and CHAT signals suggests specific transduction of the motor neurons.

AAV.CPP.16 and AAV.CPP.21 also showed enhanced ability vs. AAV9 in targeting the spinal cord and motor neurons in mice. All AAVs carry nuclear RFP as reporter and were administered intravenously into neonate mice ($4\times10^{10}$ vg). Motor neurons were visualized using CHAT antibody staining. Co-localization of RFP and CHAT signals in FIG. 8B suggested specific transduction of the motor neurons.

The relative abilities of AAV-CAG-H2B-RFP and AAV.CPP.16-CAG-H2B-RFP to transduce various tissues in mice was also evaluated. $1\times10^{11}$ vg was injected intravenously. The number of cells transduced was normalized to the number of total cells labeled by DAPI nuclear staining. The results showed that AAV.CPP.16 was more efficient than AAV9 in targeting heart (FIG. 9A); skeletal muscle (FIG. 9B), and dorsal root ganglion (FIG. 9C) tissue in mice.

Example 7. BBB Permeation in a Non-Human Primate Model $2\times10^{13}$ vg/kg AAVs-CAG-AADC (as reporter gene) were injected intravenously into 3-month-old cynomolgus monkeys. AAV-transduced cells (shown in black) were visualized using antibody staining against AADC. As shown in FIGS. 10A-D, AAV.CPP.16 and AAV.CPP.21 showed enhanced ability vs. AAV9 to transduce brain cells after intravenous administration in non-human primates. AAV.CPP.16 transduced significantly more cells then wt AAV9 in the primary visual cortex (FIG. 10A), parietal cortex (FIG. 10B), thalamus (FIG. 10C), and cerebellum (FIG. 10D). See Materials and Methods #7-8 for more details.

Example 8. AAV.CPP.16 and AAV.CPP.21 do not Bind to LY6A

LY6A serves as a receptor for AAV.PHP.eB and mediates AAV.PHP.eB's robust effect in crossing the BBB in certain mouse strains. Over-expressing mouse LY6A in cultured 293 cells significantly increased binding of AAV.PHP.eB to the cell surface (see FIG. 11A). On the contrary, over-expressing LY6A does not increase viral binding for AAV9, AAV.CPP.16 or AAV.CPP.21 (see FIG. 11B). This suggests AAV.CPP.16 or AAV.CPP.21 does not share LY6A with AAV.PHP.eB as a receptor. See Materials and Methods #9 for more details.

Example 9. Delivering Therapeutic Proteins to the Brain Using AAV.CPP.21

AAV.CPP.21 was used to systemically deliver the "suicide gene" HSV.TK1 in a mouse model of brain tumor. HSV.TK1 turns the otherwise "dormant" ganciclovir into a tumor-killing drug. Intravenously administered AAV.CPP.21-H2BmCherry (FIG. 12A, bottom left and middle right panel) was shown to target tumor mass, especially the tumor expanding frontier. As shown in FIGS. 12B-C, using AAV.CPP.21 to systemically deliver the "suicide gene" HSV.TK1 resulted in shrinkage of brain tumor mass, when combined with the pro-drug ganciclovir. These results show that AAV.CPP.21 can be used to systemically deliver a therapeutic gene into brain tumor. See Materials and Methods #10 for more details.

Example 10. Intracerebral Administration of AAV.CPP.21

In addition to systemic administration (such as in Example 2), an AAV as described herein was administered locally into the mouse brain. Intracerebral injection of AAV9-H2B-RFP and AAV.CPP.21-H2B-RFP (FIG. 13) resulted in more widespread and higher-intensity RFP signal in AAV.CPP.21-treated brain sections vs. AAV9-treated ones. See Materials and Methods #4 for more details.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 104
SEQ ID NO: 1             moltype = AA  length = 5
FEATURE                  Location/Qualifiers
REGION                   1..5
                         note = Description of Artificial Sequence: Syntheticpeptide
source                   1..5
                         mol_type = protein
                         organism = synthetic construct
SEQUENCE: 1
VPALR                                                                5

SEQ ID NO: 2             moltype = AA  length = 5
FEATURE                  Location/Qualifiers
REGION                   1..5
                         note = Description of Artificial Sequence: Syntheticpeptide
source                   1..5
                         mol_type = protein
                         organism = synthetic construct
SEQUENCE: 2
VSALK                                                                5

SEQ ID NO: 3             moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 3
TVPALR                                                               6

SEQ ID NO: 4             moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 4
TVSALK                                                               6

SEQ ID NO: 5             moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 5
FTVSALK                                                              7

SEQ ID NO: 6             moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 6
LTVSALK                                                              7

SEQ ID NO: 7             moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 7
TFVSALK                                                              7

SEQ ID NO: 8             moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
```

-continued

```
SEQUENCE: 8
TVSALFK                                                            7

SEQ ID NO: 9           moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 9
TVPALFR                                                            7

SEQ ID NO: 10          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 10
TVPMLFK                                                            7

SEQ ID NO: 11          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 11
TVPTLFK                                                            7

SEQ ID NO: 12          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 12
TVPMLK                                                             6

SEQ ID NO: 13          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 13
TVPTLK                                                             6

SEQ ID NO: 14          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 14
VPMLK                                                              5

SEQ ID NO: 15          moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 15
VPTLK                                                              5

SEQ ID NO: 16          moltype = AA  length = 6
FEATURE                Location/Qualifiers
REGION                 1..6
                       note = Description of Artificial Sequence: Syntheticpeptide
source                 1..6
                       mol_type = protein
```

```
                        organism = synthetic construct
SEQUENCE: 16
VPMLKE                                                                          6

SEQ ID NO: 17           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 17
VPTLKD                                                                          6

SEQ ID NO: 18           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 18
VPALRD                                                                          6

SEQ ID NO: 19           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 19
VSALKE                                                                          6

SEQ ID NO: 20           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 20
VSALKD                                                                          6

SEQ ID NO: 21           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 21
TAVSLK                                                                          6

SEQ ID NO: 22           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 22
TALVSK                                                                          6

SEQ ID NO: 23           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 23
TVLSAK                                                                          6

SEQ ID NO: 24           moltype = AA  length = 6
FEATURE                 Location/Qualifiers
REGION                  1..6
                        note = Description of Artificial Sequence: Syntheticpeptide
source                  1..6
```

```
                        mol_type = protein
                        organism = synthetic construct
SEQUENCE: 24
TLVSAK                                                                      6

SEQ ID NO: 25           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 25
TMVPLK                                                                      6

SEQ ID NO: 26           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 26
TMLVPK                                                                      6

SEQ ID NO: 27           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 27
TVLPMK                                                                      6

SEQ ID NO: 28           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 28
TLVPMK                                                                      6

SEQ ID NO: 29           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 29
TTVPLK                                                                      6

SEQ ID NO: 30           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 30
TTLVPK                                                                      6

SEQ ID NO: 31           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 31
TVLPTK                                                                      6

SEQ ID NO: 32           moltype = AA  length = 6
FEATURE                 Location/Qualifiers
REGION                  1..6
                        note = Description of Artificial Sequence: Syntheticpeptide
```

```
source                  1..6
                        mol_type = protein
                        organism = synthetic construct
SEQUENCE: 32
TLVPTK                                                                      6

SEQ ID NO: 33           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 33
TAVPLR                                                                      6

SEQ ID NO: 34           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 34
TALVPR                                                                      6

SEQ ID NO: 35           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 35
TVLPAR                                                                      6

SEQ ID NO: 36           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 36
TLVPAR                                                                      6

SEQ ID NO: 37           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 37
TAVSLKE                                                                     7

SEQ ID NO: 38           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 38
TALVSKE                                                                     7

SEQ ID NO: 39           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 39
TVLSAKE                                                                     7

SEQ ID NO: 40           moltype = AA  length = 7
FEATURE                 Location/Qualifiers
REGION                  1..7
```

```
                        note = Description of Artificial Sequence: Syntheticpeptide
source                  1..7
                        mol_type = protein
                        organism = synthetic construct
SEQUENCE: 40
TLVSAKE                                                                      7

SEQ ID NO: 41           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 41
TMVPLKE                                                                      7

SEQ ID NO: 42           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 42
TMLVPKE                                                                      7

SEQ ID NO: 43           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 43
TVLPMKE                                                                      7

SEQ ID NO: 44           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 44
TLVPMKE                                                                      7

SEQ ID NO: 45           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 45
TTVPLKD                                                                      7

SEQ ID NO: 46           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 46
TTLVPKD                                                                      7

SEQ ID NO: 47           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 47
TVLPTKD                                                                      7

SEQ ID NO: 48           moltype = AA  length = 7
FEATURE                 Location/Qualifiers
```

```
REGION                1..7
                      note = Description of Artificial Sequence: Syntheticpeptide
source                1..7
                      mol_type = protein
                      organism = synthetic construct
SEQUENCE: 48
TLVPTKD                                                       7

SEQ ID NO: 49         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 49
TAVPLRD                                                       7

SEQ ID NO: 50         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 50
TALVPRD                                                       7

SEQ ID NO: 51         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 51
TVLPARD                                                       7

SEQ ID NO: 52         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 52
TLVPARD                                                       7

SEQ ID NO: 53         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 53
TAVSLFK                                                       7

SEQ ID NO: 54         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 54
TALVSFK                                                       7

SEQ ID NO: 55         moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 55
TVLSAFK                                                       7

SEQ ID NO: 56         moltype = AA  length = 7
```

```
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 56
TLVSAFK                                                                    7

SEQ ID NO: 57           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 57
TMVPLFK                                                                    7

SEQ ID NO: 58           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 58
TMLVPFK                                                                    7

SEQ ID NO: 59           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 59
TVLPMFK                                                                    7

SEQ ID NO: 60           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 60
TLVPMFK                                                                    7

SEQ ID NO: 61           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 61
TTVPLFK                                                                    7

SEQ ID NO: 62           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 62
TTLVPFK                                                                    7

SEQ ID NO: 63           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 63
TVLPTFK                                                                    7
```

-continued

```
SEQ ID NO: 64          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 64
TLVPTFK                                                       7

SEQ ID NO: 65          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 65
TAVPLFR                                                       7

SEQ ID NO: 66          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 66
TALVPFR                                                       7

SEQ ID NO: 67          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 67
TVLPAFR                                                       7

SEQ ID NO: 68          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 68
TLVPAFR                                                       7

SEQ ID NO: 69          moltype = AA  length = 8
FEATURE                Location/Qualifiers
source                 1..8
                       mol_type = protein
                       organism = Homo sapiens
SEQUENCE: 69
KFTVPMLK                                                      8

SEQ ID NO: 70          moltype = AA  length = 8
FEATURE                Location/Qualifiers
source                 1..8
                       mol_type = protein
                       organism = Mus sp.
SEQUENCE: 70
KLTVPTLK                                                      8

SEQ ID NO: 71          moltype = AA  length = 8
FEATURE                Location/Qualifiers
source                 1..8
                       mol_type = protein
                       organism = Rattus sp.
SEQUENCE: 71
KFTVPALR                                                      8

SEQ ID NO: 72          moltype = AA  length = 8
FEATURE                Location/Qualifiers
REGION                 1..8
                       note = Description of Artificial Sequence: Syntheticpeptide
source                 1..8
```

```
                        mol_type = protein
                        organism = synthetic construct
SEQUENCE: 72
KFTVSALK                                                8

SEQ ID NO: 73           moltype =   length =
SEQUENCE: 73
000

SEQ ID NO: 74           moltype =   length =
SEQUENCE: 74
000

SEQ ID NO: 75           moltype =   length =
SEQUENCE: 75
000

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype = AA  length = 6
FEATURE                 Location/Qualifiers
REGION                  1..6
                        note = Description of Artificial Sequence: Syntheticpeptide
MOD_RES                 3
                        note = S or P
MOD_RES                 4
                        note = A, M, or T
REGION                  1..6
                        note = See specification as filed for detailed description
                         ofsubstitutions and preferred embodiments
source                  1..6
                        mol_type = protein
                        organism = synthetic construct
SEQUENCE: 81
TVXXLK                                                  6

SEQ ID NO: 82           moltype = AA  length = 7
FEATURE                 Location/Qualifiers
REGION                  1..7
                        note = Description of Artificial Sequence: Syntheticpeptide
MOD_RES                 3
                        note = S or P
MOD_RES                 4
                        note = A, M, or T
REGION                  1..7
                        note = See specification as filed for detailed description
                         ofsubstitutions and preferred embodiments
source                  1..7
                        mol_type = protein
                        organism = synthetic construct
SEQUENCE: 82
TVXXLFK                                                 7

SEQ ID NO: 83           moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 83
```

-continued

```
KLASVT                                                          6

SEQ ID NO: 84           moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 84
KFLASVT                                                         7

SEQ ID NO: 85           moltype = AA  length = 736
FEATURE                 Location/Qualifiers
source                  1..736
                        mol_type = protein
                        organism = Adeno-associated virus 9
SEQUENCE: 85
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                               736

SEQ ID NO: 86           moltype = AA  length = 609
FEATURE                 Location/Qualifiers
source                  1..609
                        mol_type = protein
                        organism = Homo sapiens
SEQUENCE: 86
MSGWESYYKT EGDEEAEEEQ EENLEASGDY KYSGRDSLIF LVDASKAMFE SQSEDELTPF  60
DMSIQCIQSV YISKIISSDR DLLAVVFYGT EKDKNSVNFK NIYVLQELDN PGAKRILELD  120
QFKGQQGQKR FQDMMGHGSD YSLSEVLWVC ANLFSDVQFK MSHKRIMLFT NEDNPHGNDS  180
AKASRARTKA GDLRDTGIFL DLMHLKKPGG FDISLFYRDI ISIAEDEDLR VHFEESSKLE  240
DLLRKVRAKE TRKRALSRLK LKLNKDIVIS VGIYNLVQKA LKPPPIKLYR ETNEPVKTKT  300
RTFNTSTGGL LLPSDTKRSQ IYGSRQIILE KEETEELKRF DDPGLMLMGF KPLVLLKKHH  360
YLRPSLFVYP EESLVIGSST LFSALLIKCL EKEVAALCRY TPRRNIPPYF VALVPQEEEL  420
DDQKIQVTPP GFQLVFLPFA DDKRKMPFTE KIMATPEQVG KMKAIVEKLR FTYRSDSFEN  480
PVLQQHFRNL EALALDLMEP EQAVDLTLPK VEAMNKRLGS LVDEFKELVY PPDYNPEGKV  540
TKRKHDNEGS GSKRPKVEYS EEELKTHISK GTLGKFTVPM LKEACRAYGL KSGLKKQELL  600
EALTKHFQD                                                       609

SEQ ID NO: 87           moltype = AA  length = 608
FEATURE                 Location/Qualifiers
source                  1..608
                        mol_type = protein
                        organism = Mus sp.
SEQUENCE: 87
MSEWESYYKT EGEEEEEEEE SPDTGGEYKY SGRDSLIFLV DASRAMFESQ GEDELTPFDM  60
SIQCIQSVYT SKIISSDRDL LAVVFYGTEK DKNSVNFKNI YVLQDLDNPG AKRVLELDQF  120
KGQQGKKHFR DTVGHGSDYS LSEVLWVCAN LFSDVQLKMS HKRIMLFTNE DDPHGRDSAK  180
ASRARTKASD LRDTGIFLDL MHLKKPGGFD VSVFYRDIIT TAEDEDLGVH FEESSKLEDL  240
LRKVRAKETK KRVLSRLKFK LGEDVVLMVG IYNLVQKANK PFPVRLYRET NEPVKTKTRT  300
FNVNTGSLLL PSDTKRSLTY GTRQIVLEKE ETEELKRFDE PGLILMGFKP TVMLKKQHYL  360
RPSLFVYPEE SLVSGSSTLF SALLTKCVEK EVIAVCRYTP RKNVSPYFVA LVPQEEELDD  420
QNIQVTPGGF QLVFLPYADD KRKVPFTEKV TANQEQIDKM KAIVQKLRFT YRSDSFENPV  480
LQQHFRNLEA LALDMMESEQ VVDLTLPKVE AIKKRLGSLA DEFKELVYPP GYNPEGKVAK  540
RKQDDEGSTS KKPKVELSEE ELKAHFRKGT LGKLTVPTLK DICKAHGLKS GPKKQELLDA  600
LIRHLEKN                                                        608

SEQ ID NO: 88           moltype = AA  length = 608
FEATURE                 Location/Qualifiers
source                  1..608
                        mol_type = protein
                        organism = Rattus sp.
SEQUENCE: 88
MSEWESYYKT EGEEEEEEEQ SPDTNGEYKY SGRDSLIFLV DASRAMFESQ GEDELTPFDM  60
SIQCIQSVYT SKIISSDRDL LAVVFYGTEK DKNSVNFKSI YVLQDLDNPG AKRVLELDRF  120
KGQQGKKHFR DTIGHGSDYS LSEVLWVCAN LFSDVQFKMS HKRIMLFTNE DDPHGNDSAK  180
ASRARTKASD LRDTGIFLDL MHLKKRGGFD VSLFYRDIIS IAEDEDLGVH FEESSKLEDL  240
LRKVRAKETK KRVLSRLKFK LGKDVALMVG VYNLVQKANK PFPVRLYRET NEPVKTKTRT  300
```

```
FNVNTGSLLL PSDTKRSLTF GTRQIVLEKE ETEELKRFDE PGLILMGFKP MVMLKNHHYL  360
RPSLFLYPEE SLVNGSSTLF SALLTKCVEK EVIAVCRYTA RKNVSPYFVA LVPQEEELDD  420
QNIQVTPAGF QLVFLPYADD KRKVPFTEKV MANPEQIDKM KAIVQKLRFT YRSDSFENPV  480
LQQHFRNLEA LALDMMESEQ VVDLTLPKVE AIKKRLGSLA DEFKELVYPP GYNPEGKIAK  540
RKADNEGSAS KKPKVELSEE ELKDLFAKGT LGKLTVPALR DICKAYGLKS GPKKQELLEA  600
LSRHLEKN                                                          608

SEQ ID NO: 89          moltype = AA  length = 742
FEATURE                Location/Qualifiers
REGION                 1..742
                       note = Description of Artificial Sequence:
                        Syntheticpolypeptide
source                 1..742
                       mol_type = protein
                       organism = synthetic construct
SEQUENCE: 89
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTV SALKAQAQTG  600
WVQNQGILPG MVWQDRDVYL QGPIWAKIPH TDGNFHPSPL MGGFGMKHPP PQILIKNTPV  660
PADPPTAFNK DKLNSFITQY STGQVSVEIE WELQKENSKR WNPEIQYTSN YYKSNNVEFA  720
VNTEGVYSEP RPIGTRYLTR NL                                          742

SEQ ID NO: 90          moltype = AA  length = 743
FEATURE                Location/Qualifiers
REGION                 1..743
                       note = Description of Artificial Sequence:
                        Syntheticpolypeptide
source                 1..743
                       mol_type = protein
                       organism = synthetic construct
SEQUENCE: 90
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTV SALFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 91          moltype = DNA  length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 91
ggaaccccta gtgatggagt t                                           21

SEQ ID NO: 92          moltype = DNA  length = 16
FEATURE                Location/Qualifiers
misc_feature           1..16
                       note = Description of Artificial Sequence: Syntheticprimer
source                 1..16
                       mol_type = other DNA
                       organism = synthetic construct
SEQUENCE: 92
cggcctcagt gagcga                                                 16

SEQ ID NO: 93          moltype = AA  length = 18
FEATURE                Location/Qualifiers
REGION                 1..18
                       note = Description of Unknown:SynB1 sequence
source                 1..18
                       mol_type = protein
```

```
                         organism = unidentified
SEQUENCE: 93
RGGRLSYSRR RFSTSTGR                                                18

SEQ ID NO: 94            moltype = AA  length = 20
FEATURE                  Location/Qualifiers
REGION                   1..20
                         note = Description of Artificial Sequence: Syntheticpeptide
source                   1..20
                         mol_type = protein
                         organism = synthetic construct
SEQUENCE: 94
HARIKPTFRR LKWKYKGKFW                                              20

SEQ ID NO: 95            moltype = AA  length = 12
FEATURE                  Location/Qualifiers
REGION                   1..12
                         note = Description of Artificial Sequence: Syntheticpeptide
source                   1..12
                         mol_type = protein
                         organism = synthetic construct
SEQUENCE: 95
PLSSIFSRIG DP                                                      12

SEQ ID NO: 96            moltype = AA  length = 21
FEATURE                  Location/Qualifiers
REGION                   1..21
                         note = Description of Artificial Sequence: Syntheticpeptide
source                   1..21
                         mol_type = protein
                         organism = synthetic construct
SEQUENCE: 96
AGYLLGKINL KALAALAKKI L                                            21

SEQ ID NO: 97            moltype = AA  length = 18
FEATURE                  Location/Qualifiers
REGION                   1..18
                         note = Description of Artificial Sequence: Syntheticpeptide
source                   1..18
                         mol_type = protein
                         organism = synthetic construct
SEQUENCE: 97
VRLPPPVRLP PPVRLPPP                                                18

SEQ ID NO: 98            moltype = AA  length = 18
FEATURE                  Location/Qualifiers
REGION                   1..18
                         note = Description of Artificial Sequence: Syntheticpeptide
source                   1..18
                         mol_type = protein
                         organism = synthetic construct
SEQUENCE: 98
VELPPPVELP PPVELPPP                                                18

SEQ ID NO: 99            moltype = AA  length = 16
FEATURE                  Location/Qualifiers
REGION                   1..16
                         note = Description of Artificial Sequence: Syntheticpeptide
source                   1..16
                         mol_type = protein
                         organism = synthetic construct
SEQUENCE: 99
KGTYKKKLMR IPLKGT                                                  16

SEQ ID NO: 100           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 100
PPRPPRPPR                                                          9

SEQ ID NO: 101           moltype = AA  length = 15
FEATURE                  Location/Qualifiers
REGION                   1..15
                         note = Description of Artificial Sequence: Syntheticpeptide
source                   1..15
```

-continued

```
                        mol_type = protein
                        organism = synthetic construct
SEQUENCE: 101
PPRPPRPPRP PRPPR                                                15

SEQ ID NO: 102          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 102
RRRRRRRR                                                        8

SEQ ID NO: 103          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 103
LRRERQSRLR RERQSR                                               16

SEQ ID NO: 104          moltype = AA  length = 9
FEATURE                 Location/Qualifiers
source                  1..9
                        mol_type = protein
                        organism = Human immunodeficiency virus 1
SEQUENCE: 104
RKKRRQRRR                                                       9
```

What is claimed is:

1. A method of delivering a transgene to a subject, the method comprising administering to the subject an adeno-associated virus (AAV) vector comprising (i) a transgene, and (ii) an AAV capsid comprising a peptide insert of up to 21 amino acids, wherein the peptide insert comprises 5-7 contiguous amino acids of TVSALFK (SEQ ID NO: 8).

2. The method of claim 1, wherein the transgene comprises a sequence encoding a therapeutic agent.

3. The method of claim 1, wherein delivery of the transgene to an organ or tissue is enhanced relative to an AAV vector comprising an AAV capsid without the peptide insert and the transgene.

4. The method of claim 1, wherein the transgene is delivered to an organ or tissue comprising permeability barriers.

5. The method of claim 1, wherein the transgene is delivered to an organ or tissue comprising epithelium comprising tight junctions.

6. The method of claim 1, wherein the transgene is delivered to the brain or central nervous system.

7. The method of claim 1, wherein the transgene is delivered to the cortex, cerebellum, hippocampus, substantia nigra, thalamus, or amygdala.

8. The method of claim 1, wherein the transgene is delivered to neurons, astrocytes, glial cells, or cardiomyocytes.

9. The method of claim 1, wherein the subject has a neurodegenerative disease or a cancer.

10. The method of claim 9, wherein the neurodegenerative disease is Parkinson's disease, Alzheimer's disease, Huntington's disease, amyotrophic lateral sclerosis, multiple sclerosis, epilepsy, stroke, spinocerebellar ataxia, or Canavan's disease.

11. The method of claim 9, wherein the cancer is a brain cancer.

12. The method of claim 6, wherein the subject has a neurodegenerative disease or a cancer.

13. A method of delivering a non-coding RNA to a subject, the method comprising administering to the subject an adeno-associated virus (AAV) vector comprising (i) a non-coding RNA, and (ii) an AAV capsid comprising a peptide insert of up to 21 amino acids, wherein the peptide insert comprises 5-7 contiguous amino acids of TVSALFK (SEQ ID NO: 8).

14. The method of claim 13, wherein delivery of the non-coding RNA to an organ or tissue is enhanced relative to an AAV vector comprising an AAV capsid without the peptide insert and the non-coding RNA.

15. The method of claim 13, wherein the non-coding RNA is delivered to an organ or tissue comprising permeability barriers.

16. The method of claim 13, wherein the non-coding RNA is delivered to an organ or tissue comprising epithelium comprising tight junctions.

17. The method of claim 13, wherein the non-coding RNA is delivered to the brain or central nervous system.

18. The method of claim 13, wherein the non-coding RNA is delivered to the cortex, cerebellum, hippocampus, substantia nigra, thalamus, or amygdala.

19. The method of claim 13, wherein the non-coding RNA is delivered to neurons, astrocytes, glial cells, or cardiomyocytes.

20. The method of claim 13, wherein the subject has a neurodegenerative disease or a cancer.

21. The method of claim 20, wherein the neurodegenerative disease is Parkinson's disease, Alzheimer's disease, Huntington's disease, amyotrophic lateral sclerosis, multiple sclerosis, epilepsy, stroke, spinocerebellar ataxia, or Canavan's disease.

22. The method of claim 20, wherein the cancer is a brain cancer.

23. The method of claim 17, wherein the subject has a neurodegenerative disease or a cancer.

24. A method of treating a disorder of the brain or central nervous system in a subject, the method comprising administering to the subject an AAV vector comprising (i) a non-coding RNA or a transgene encoding a therapeutic agent, and (ii) an AAV capsid comprising a peptide insert of up to 21 amino acids, wherein the peptide insert comprises 5-7 contiguous amino acids of TVSALFK (SEQ ID NO: 8), thereby treating the disorder.

25. The method of claim 24, wherein the disorder is a neurodegenerative disease.

26. The method of claim 25, wherein the neurodegenerative disease is Parkinson's disease, Alzheimer's disease, Huntington's disease, amyotrophic lateral sclerosis, multiple sclerosis, epilepsy, stroke, spinocerebellar ataxia, or Canavan's disease.

27. The method of claim 24, wherein the disorder is a cancer.

28. The method of claim 1, wherein the peptide insert comprises 5 contiguous amino acids of TVSALFK (SEQ ID NO: 8).

29. The method of claim 1, wherein the peptide insert comprises 6 contiguous amino acids of TVSALFK (SEQ ID NO: 8).

30. The method of claim 1, wherein the peptide insert comprises 7 contiguous amino acids of TVSALFK (SEQ ID NO: 8).

31. The method of claim 13, wherein the peptide insert comprises 5 contiguous amino acids of TVSALFK (SEQ ID NO: 8).

32. The method of claim 13, wherein the peptide insert comprises 6 contiguous amino acids of TVSALFK (SEQ ID NO: 8).

33. The method of claim 13, wherein the peptide insert comprises 7 contiguous amino acids of TVSALFK (SEQ ID NO: 8).

34. The method of claim 24, wherein the peptide insert comprises 5 contiguous amino acids of TVSALFK (SEQ ID NO: 8).

35. The method of claim 24, wherein the peptide insert comprises 6 contiguous amino acids of TVSALFK (SEQ ID NO: 8).

36. The method of claim 24, wherein the peptide insert comprises 7 contiguous amino acids of TVSALFK (SEQ ID NO: 8).

* * * * *